(12) United States Patent
Nakamoto et al.

(10) Patent No.: US 7,829,585 B2
(45) Date of Patent: Nov. 9, 2010

(54) ANTIFUNGAL AGENT CONTAINING PYRIDINE DERIVATIVE

(75) Inventors: Kazutaka Nakamoto, Tsukuba (JP); Satoshi Inoue, Tsukuba (JP); Keigo Tanaka, Tsukuba (JP); Toru Haneda, Kamisu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 215 days.

(21) Appl. No.: 11/887,249

(22) PCT Filed: Mar. 29, 2006

(86) PCT No.: PCT/JP2006/306422

§ 371 (c)(1),
(2), (4) Date: Sep. 27, 2007

(87) PCT Pub. No.: WO2006/106711

PCT Pub. Date: Oct. 12, 2006

(65) Prior Publication Data

US 2009/0062348 A1 Mar. 5, 2009

(30) Foreign Application Priority Data

Mar. 30, 2005 (JP) ............................. 2005-098255

(51) Int. Cl.
*A61K 31/443* (2006.01)
*C07D 405/12* (2006.01)

(52) U.S. Cl. .................................. 514/337; 546/284.1

(58) Field of Classification Search .............. 546/284.1; 514/337

See application file for complete search history.

(56) References Cited

U.S. PATENT DOCUMENTS

| | | | |
|---|---|---|---|
| 4,576,956 A | 3/1986 | Makisumi et al. |
| 4,720,493 A | 1/1988 | Kawakita et al. |
| 4,785,010 A | 11/1988 | Zoller et al. |
| 5,034,393 A | 7/1991 | Hackler et al. |
| 5,296,484 A | 3/1994 | Coghlan et al. |
| 5,350,749 A | 9/1994 | Hackler et al. |
| 5,371,086 A | 12/1994 | Takemoto et al. |
| 5,691,136 A | 11/1997 | Lupski et al. |
| 5,691,336 A | 11/1997 | Dorn et al. |
| 5,710,171 A | 1/1998 | Dinsmore et al. |
| 5,747,518 A | 5/1998 | Yoshikawa et al. |
| 5,852,042 A | 12/1998 | Jakobi et al. |
| 5,945,431 A | 8/1999 | Jin et al. |
| 6,022,884 A | 2/2000 | Mantlo et al. |
| 6,080,767 A | 6/2000 | Klein et al. |
| 6,140,131 A | 10/2000 | Sunakawa et al. |
| 6,235,728 B1 | 5/2001 | Golik et al. |
| 6,313,127 B1 | 11/2001 | Waterson et al. |
| 6,380,218 B1 | 4/2002 | Marfat et al. |
| 6,414,013 B1 | 7/2002 | Fancelli et al. |
| 6,596,718 B1 | 7/2003 | Flohr et al. |
| 6,630,495 B1 | 10/2003 | Cooke et al. |
| 7,179,804 B2 | 2/2007 | Amegadzie et al. |
| 7,179,822 B2 | 2/2007 | Bunker et al. |
| 2002/0011495 A1 | 1/2002 | Clemmons |
| 2002/0111495 A1 | 8/2002 | Magee et al. |
| 2003/0045554 A1 | 3/2003 | Sankaranarayanan |
| 2003/0114491 A1 | 6/2003 | Kim et al. |
| 2003/0191158 A1 | 10/2003 | Magee |
| 2004/0038239 A1 | 2/2004 | Tsukahara et al. |
| 2004/0044040 A1 | 3/2004 | Neubert et al. |
| 2004/0152730 A1 | 8/2004 | Farina et al. |
| 2004/0198773 A1 | 10/2004 | Hart et al. |
| 2005/0119229 A1 | 6/2005 | Ammermann et al. |
| 2006/0264419 A1 | 11/2006 | Schiemann et al. |
| 2007/0105904 A1 | 5/2007 | Tanaka et al. |
| 2007/0105943 A1 | 5/2007 | Nakamoto et al. |
| 2007/0167493 A1 | 7/2007 | Sankaranarayanan |
| 2009/0084621 A1 | 4/2009 | Giovannini et al. |

FOREIGN PATENT DOCUMENTS

| | | |
|---|---|---|
| DE | 19727117 A1 | 1/1999 |
| EP | 0124067 A1 | 11/1984 |
| EP | 0124154 A2 | 11/1984 |

(Continued)

OTHER PUBLICATIONS

Vippagunta et al., Crystalline Solids, Advanced Drug Reviews, 48 (2001), 3-26.*

(Continued)

*Primary Examiner*—Patricia L Morris
(74) *Attorney, Agent, or Firm*—Birch, Stewart, Kolasch & Birch, LLP

(57) ABSTRACT

The present invention provides an antifungal agent that has superior antifungal action and is also superior in terms of physical properties, safety and metabolic stability. The present invention discloses a compound represented by the formula (I):

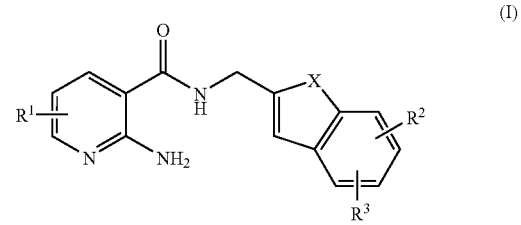

(I)

(wherein X represents an oxygen atom, a sulfur atom or —NH—, $R^1$ represents a hydrogen atom, a halogen atom, a cyano group, an amino group or a substituent, and $R^2$ and $R^3$ independently represent a hydrogen atom, a halogen atom, a hydroxyl group or a substituent, except for a case in which $R^2$ and $R^3$ are both hydrogen atoms), and an antifungal agent containing the above compound.

11 Claims, No Drawings

FOREIGN PATENT DOCUMENTS

| | | |
|---|---|---|
| EP | 0274867 A2 | 7/1988 |
| EP | 0 326 328 A2 | 8/1989 |
| EP | 0414386 A1 | 2/1991 |
| EP | 0533130 A1 | 3/1993 |
| EP | 0976744 A1 | 2/2000 |
| EP | 1 216 980 A1 | 6/2002 |
| EP | 1217000 A1 | 6/2002 |
| EP | 1229034 A1 | 8/2002 |
| EP | 1275301 A1 | 1/2003 |
| EP | 1275653 A1 | 1/2003 |
| EP | 1 369 420 A1 | 12/2003 |
| EP | 1 669 348 A1 | 6/2006 |
| EP | 1 782 811 A1 | 5/2007 |
| JP | 54-2325 A | 1/1979 |
| JP | 59-73575 A | 4/1984 |
| JP | 59-206353 A | 11/1984 |
| JP | 61-148178 A | 7/1986 |
| JP | 64-3162 A | 1/1989 |
| JP | 1-246264 A | 10/1989 |
| JP | 3-66689 A | 3/1991 |
| JP | 3-161470 A | 7/1991 |
| JP | 5-294935 A | 11/1993 |
| JP | 7-25853 A | 1/1995 |
| JP | 8-175933 A | 7/1996 |
| JP | 8-175993 A | 7/1996 |
| JP | 10-505600 A | 6/1998 |
| JP | 2000-504336 A | 4/2000 |
| JP | 2000-178243 A | 6/2000 |
| JP | 2001-522834 A | 11/2001 |
| JP | 2001-527083 A | 12/2001 |
| JP | 2002-275159 A | 9/2002 |
| JP | 2002-284766 A | 10/2002 |
| JP | 2003-506466 A | 2/2003 |
| JP | 2004-529154 A | 9/2004 |
| JP | 2005-033079 A | 2/2005 |
| JP | 2005-526751 A | 9/2005 |
| JP | 2006-519247 A | 8/2006 |
| WO | WO-86/03203 A1 | 6/1986 |
| WO | WO-93/12084 A1 | 6/1993 |
| WO | WO-96/09294 A1 | 3/1996 |
| WO | WO-97/27852 A1 | 8/1997 |
| WO | WO-97/28128 A1 | 8/1997 |
| WO | WO-98/25883 A1 | 6/1998 |
| WO | WO-98/50029 A1 | 11/1998 |
| WO | WO-99/24404 A1 | 5/1999 |
| WO | WO-99/48492 A1 | 9/1999 |
| WO | WO-99/50247 A1 | 10/1999 |
| WO | WO-00/07991 A1 | 2/2000 |
| WO | WO-00/51998 A1 | 9/2000 |
| WO | WO-00/62778 A1 | 10/2000 |
| WO | WO-00/73283 A1 | 12/2000 |
| WO | WO-01/11966 A1 | 2/2001 |
| WO | WO-01/21584 A1 | 3/2001 |
| WO | WO-01/25181 A1 | 4/2001 |
| WO | WO 01/26651 A1 | 4/2001 |
| WO | WO-01/27096 A1 | 4/2001 |
| WO | WO-01/51456 A2 | 7/2001 |
| WO | WO-01/53274 A1 | 7/2001 |
| WO | WO-01/74779 A1 | 10/2001 |
| WO | WO-02/00651 A2 | 1/2002 |
| WO | WO-02/04626 A1 | 1/2002 |
| WO | WO-02/06275 A1 | 1/2002 |
| WO | WO-02/22583 A2 | 3/2002 |
| WO | WO-02/060875 A1 | 8/2002 |
| WO | WO-02/060896 A1 | 8/2002 |
| WO | WO-02/060898 A1 | 8/2002 |
| WO | WO-02/083645 A1 | 10/2002 |
| WO | WO-02/085697 A1 | 10/2002 |
| WO | WO-02/085897 A1 | 10/2002 |
| WO | WO 03/006628 A2 | 1/2003 |
| WO | WO-03/027095 A1 | 4/2003 |
| WO | WO-03/031435 A1 | 4/2003 |
| WO | 03/045920 A1 | 6/2003 |
| WO | WO-03/045385 A1 | 6/2003 |
| WO | WO-03/059903 A2 | 7/2003 |
| WO | 03/068747 A1 | 8/2003 |
| WO | WO-03/068232 A1 | 8/2003 |
| WO | WO-03/068235 A1 | 8/2003 |
| WO | WO 03/091226 A1 | 11/2003 |
| WO | WO 03/091227 A1 | 11/2003 |
| WO | WO-2004/000813 A1 | 12/2003 |
| WO | WO 2004/014366 A1 | 2/2004 |
| WO | WO-2004/014370 | 2/2004 |
| WO | WO-2004/029027 A1 | 4/2004 |
| WO | WO-2004/033432 A1 | 4/2004 |
| WO | WO-2004/048567 A2 | 6/2004 |
| WO | WO-2004/052280 A2 | 6/2004 |
| WO | WO-2004/089931 A1 | 10/2004 |
| WO | WO-2005/033079 A1 | 4/2005 |
| WO | WO-2006/016548 | 2/2006 |
| WO | WO-2006/106711 | 10/2006 |
| WO | WO-2007/052615 A1 | 5/2007 |
| WO | WO 2009/081970 A1 | 7/2009 |
| WO | WO 2009/084621 A | 7/2009 |
| WO | WO 2009/084621 A1 | 7/2009 |

OTHER PUBLICATIONS

Guillory, "Generation of Polymorphs, etc.," in Brittain ed., Polymorphim in Pharmaceutical Solids, 95, Marcel Dekker, NY, 1999, 1-2, 183-226.*
Co-pending Office Action for U.S. Appl. No. 10/573,890 dated Jul. 29, 2009.
Accession No. 2020895193, CHEMCATS (Jul. 9, 2007).
Accession No. 2036647688, CHEMCATS (Jun. 1, 2007).
Accession No. 2021278791, CHEMCATS (Feb. 7, 2006).
Accession No. 2025887145, CHEMCATS (Jan. 1, 2007).
Ikizler et al., Indian J. Pharm. Sci., vol. 61, No. 5, pp. 271-274 (1999).
Satyanarayana et al., Bollettino Chimico Farmaceutico., vol. 140, No. 4, pp. 228-232 (2001).
Okawa et al., Synthesis, No. 10, pp. 1467-1475 (1998).
Shinkai et al., J. Med. Chem., vol. 31, pp. 2092-2097, (1988).
Ohshima et al., J. Med. Chem., vol. 35, pp. 3402-3413, (1992).
Gardner et al., Nature, vol. 419, pp. 498-511, (2002).
Naik et al., J. of Biological Chemistry, vol. 278, No. 3, pp. 2036-2042, (2003).
Chan, L., et al., Database Crossfire Beilstein: Beilstein Institute Zur Foerderung Der Chemischen Wissenschaften; XP-002512523; Database accession No. 8422493 (1999).
Okawa T., et al., "Pyrido [2, 3-d] pyrimidine derivatives. Synthesis via intermolecular aza-Wittig reaction/heterocyclization and the crystal structure", Database CA [Online] Chemical Abstract Service; XP002512524; Database accession No. 677971 (1998).
Kajino M., et al., "Preparation and formulation of quinazoline derivatives as allergy inhibitors", Database CA [Online], Chemical Abstract Service; XP002512525 Database accession No. 216905 (1999).
Piechaczek J., et al., "Monoamine oxidase inhibitors. VII. Derivatives of quinolinecarboxylic acids", Database CA [Online], Chemical Abstract Service; XP002512526 Database accession No. 75701 (1966).
Modena T., et al., "Plant growth regulating activities of 2-[2-(arylamino)-2-oxoethyl] benzoic acids", Database CA [Online], Chemical Abstract Service; XP002512527 Database accession No. 597690 (1993).
Chang et al., "Synthesis and Structure-Activity Relationship of Quaternary Ammonium Cephalosporins with 3-Pyrazolylpyridinium Derivatives," Bioorganic & Medicinal Chemistry Letters, vol. 10, 2000, pp. 1211-1214.
Connors et al., "Prodrugs in medicine," Biologicals & Immunologicals, Exp. Opin. Ther. Patents, 1995, vol. 5, No. 9, pp. 873-885.
International Search Report dated May 20, 2008 for corresponding International Application No. PCT/JP2008/057851.

Ishikawa et al., "TAK-599, a Novel N-Phosphono Type Prodrug of Anti-MRSA Cephalosporin T-91825: Synthesis, Physicochemical and Pharmacological Properties," Bioorganic & Medicinal Chemistry, vol. 11, 2003, pp. 2427-2437.

Lukevics et al., "Synthesis and cytotoxicity of silyl- and carbonyl-substituted isoxazoles," Chemistry of Heterocyclic Compounds (2000) vol. 36, No. 10, pp. 1226-1231.

Plate et al., "Synthesis and Muscarinic Activities of 3-(Pyrazolyl)-1,2,5,6-tetrahydropyridine Derivatives," Bioorganic & Medicinal Chemistry Letters (1996) vol. 4, No. 2, pp. 227-237.

Supplementary Partial European Search Report dated Feb. 2, 2009 for European Application No. 04788159.4.

US Office Action of copending U.S. Appl. No. 11/589,128 dated May 7, 2009.

Vrzheshch et al., "Supercooperativity in platelet aggregation: Substituted pyridyl isoxazoles, a new class of supercooperative platelet aggregation inhibitors," FEBS Letters (1994) vol. 351, No. 2, pp. 168-170.

Chandran et al., "Synthesis of 8-Aminoquinolines: Part II—8-Guidance Derivatives," Journal of Scientific & Industrial Reserarch (1952), 11B, pp. 129-132.

Hata, "New Approaches to Antifungal Drugs for the Treatment of Fungal and Protozoal Infections, Ravuconazole and Beyond: New Targets and Pre-clinical Strategies," The SMi's 12th Annual Conference, Superbugs and Superdrugs, Mar. 18, 2010, Crowne Plaza London—St. James, 44 pages.

Lo et al., "Development of highly selective and sensitive probes for hydrogen peroxide," Communication, Chem Comm, The Royal Society of Chemistry, 2003, pp. 2728-2729.

U.S. Office Action issued May 4, 2010 for copending U.S. Appl. No. 11/658,901.

Chang et al., "Synthesis and Structure-Activity Relationship of Quaternary Ammonium Cephalosporins with 3-Pyrazolylpyridinium Derivatives," Bioorganic & Medicinal Chemistry Letters, vol. 10, 2000, pp. 1211-1214.

Connors et al., "Prodrugs in medicine," Biologicals & Immunologicals, Exp. Opin. Ther. Patents, 1995, vol. 5, No. 9, pp. 873-885.

International Search Report dated May 20, 2008 for corresponding International Application No. PCT/JP2008/057851.

Ishikawa et al., "TAK-599, a Novel N-Phosphono Type Prodrug of Anti-MRSA Cephalosporin T-91825: Synthesis, Physicochemical and Pharmacological Properties," Bioorganic & Medicinal Chemistry, vol. 11, 2003, pp. 2427-2437.

Lukevics et al., "Synthesis and cytotoxicity of silyl- and carbonyl-substituted isoxazoles," Chemistry of Heterocyclic Compounds (2000) vol. 36, No. 10, pp. 1226-1231.

Plate et al., "Synthesis and Muscarinic Activities of 3-(Pyrazolyl)-1,2,5,6-tetrahydropyridine Derivatives," Bioorganic & Medicinal Chemistry Letters (1996) vol. 4, No. 2, pp. 227-237.

Supplementary Partial European Search Report dated Feb. 2, 2009 for European Application No. 04788159.4.

Tanaka et al., "An Effictive Lewis Acid-Mediated 1,3-Dipolar Cycloaddition of Nitrile Oxide Using Acetylene: Synthesis of a (2-Aminopyridin-3-yl) isoxazole Derivative and Its Application to Novel Antifungal Agents," pp. 1-8.

US Office Action of copending U.S. Appl. No. 11/589,128 dated May 7, 2009.

Vrzheshch et al., "Supercooperativity in platelet aggregation: Substituted pyridyl isoxazoles, a new class of supercooperative platelet aggregation inhibitors," FEBS Letters (1994) vol. 351, No. 2, pp. 168-170.

European Search Report issued Jul. 19, 2010, in corresponding European Patent Application No. 06730370.1.

Pernak, J. et al., "Synthesis and antimicrobial activities of new pyridinium and benzimidazolium chlorides," Eur. J. Med. Chem., vol. 36 (2001) pp. 313-320.

Pregnolato, M. et al., "3H-[1,2]Dithiolo[3,4-b]pyridine-3-thione and its derivatives Synthesis and antimicrobial activity," IL Farmaco, vol. 55, (2000) pp. 669-679.

European Search Report issued Jul. 29, 2010, in corresponding European Patent Application No. 05768893.9.

* cited by examiner

ANTIFUNGAL AGENT CONTAINING PYRIDINE DERIVATIVE

TECHNICAL FIELD

The present invention relates to novel antifungal agents containing pyridine derivatives.

BACKGROUND ART

Countermeasures against opportunistic infections are becoming increasingly important due to the increase in patients and elderly persons having depressed immune function due to the use of chemotherapy and other advanced treatment methods in recent years. As is indicated by the fact that opportunistic infections caused by different low virulent organisms are occurring with increasing frequency, the problem of infections will continue to be present as long as there are underlying diseases causing decreases in patients' resistance. Thus, in a society consisting of a large proportion of elderly persons that is certain to appear in the near future, new measures against infectious diseases, including the problem of resistant organisms, are expected to become an important issue.

In the field of antifungal agents, polyene-based amphotericin B or azole-based fluconazole, itraconazole or voriconazole and the like were developed in the past for the treatment of, for example, deep mycoses. Since existing drugs already available on the market frequently have a similar mechanism, the appearance of azole-resistant organisms is currently becoming a problem.

Although naturally-occurring cyclic hexapeptides in the form of caspofungin and micafungin and the like have recently been developed as 1,3-β-glucan synthase inhibitors employing a new mechanism, since these drugs are only available in the form of injections, they are still not adequate as antifungal agents.

In view of the present circumstances in which existing antifungal agents cannot be said to be adequate, there is a strong desire for the development of a highly safe drug based on a new mechanism.

Patent document 1 discloses an example of the prior art relating to an antifungal agent based on such a new mechanism. Patent document 1 describes pyridine derivatives that demonstrate effects against the onset, progression and prolongation of infections by preventing a pathogen from demonstrating pathogenicity by inhibiting the expression of cell wall surface layer protein by inhibiting the transport process of GPI (glycosyl phosphatidyl inositol) anchored protein into the cell wall, and inhibiting the cell wall assembly together with inhibiting the adherence of fungi to cells. However, the group of compounds disclosed in Patent document 1 has 2-benzylpyridine as a common structure thereof, which is clearly structurally different from the compounds according to the present invention. Moreover, although the group of compounds disclosed in Patent document 1 demonstrates activity in vitro, they have problems in vivo such as being easily metabolized.

However, patent documents 2 to 8 disclose examples of the prior art that the most structurally similar to the pyridine derivative (I) as claimed in the present invention. Patent document 2 describes N-(4-pyridyl)carboxamide derivatives having effects as an agricultural chemical, and particularly as an insecticide, miticide or nematocide. Patent documents 3 to 6 describe 2-aryloxynicotinamide derivatives having inhibitory action on phosphodiesterase 4 (PDE4), while patent document 7 describes 6-(arylamino)nicotinamide derivatives having cannabinoid receptor regulatory action, and patent document 8 describes 6-(aryloxy)nicotinamide derivatives having $Na^+/Ca^{2+}$ exchanger inhibitory action. However, compounds according to the present invention are not described in any of Patent documents 2 to 8, and antifungal action against ordinary fungal species such as *Candida*, *Aspergillus* or *Cryptococcus* species and the like are not disclosed at all in the compounds disclosed in Patent documents 2 to 8.

Patent document 1: the pamphlet of International Publication WO 02/04626

Patent document 2: the specification of U.S. Pat. No. 5,852,042

Patent document 3: the specification of European Patent Publication No. 1229034

Patent document 4: the pamphlet of International Publications WO 02/060875

Patent document 5: the pamphlet of International Publication WO 02/060896

Patent document 6: the pamphlet of International Publication WO 03/068232

Patent document 7 the pamphlet of International Publication WO 2004/029027

Patent document 8 the pamphlet of International Publication WO 2004/000813

DISCLOSURE OF INVENTION

Problems to be Solved by the Invention

An object of the present invention is to provide an antifungal agent having superior antifungal action not found in conventional antifungal agents that is also superior in terms of physical properties, safety and metabolic stability.

Means for Solving the Problems

As a result of conducting extensive studies with the foregoing in view, the inventors of the present invention succeeded in synthesizing novel pyridine derivatives represented by the following formula (I):

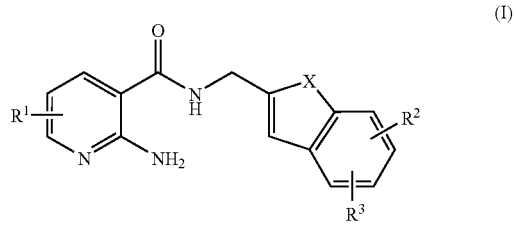

having a structure in which a 2-aminopyridine ring and a heterobicyclic group are bonded using amidomethylene as a linker, and found that these compounds have superior antifungal action, thereby leading to completion of the present invention.

Namely, the present invention provides:

[1]: a compound represented by the following formula (I), or a salt or hydrate thereof;

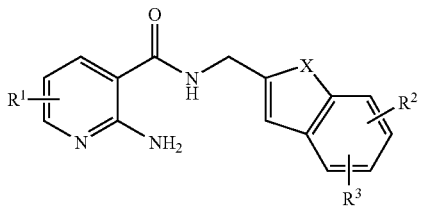
(I)

[wherein X represents an oxygen atom, sulfur atom or —NH—, $R^1$ represents a hydrogen atom, a halogen atom, a cyano group, an amino group or an arbitrary group selected from substituent group a; and $R^2$ and $R^3$ independently represent a hydrogen atom, a halogen atom, a hydroxyl group or an arbitrary group selected from substituent group c, except for a case in which $R^2$ and $R^3$ are both hydrogen atoms:

(substituent group a)

a $C_{1-6}$ alkyl group, a $C_{2-6}$ alkenyl group, a $C_{2-6}$ alkynyl group, a $C_{3-8}$ cycloalkyl group, a $C_{3-8}$ cycloalkyl $C_{1-6}$ alkyl group, a $C_{1-6}$ alkoxy group, a $C_{2-6}$ alkenyloxy group, a $C_{2-6}$ alkynyloxy group, a $C_{3-8}$ cycloalkoxy group, a $C_{3-8}$ cycloalkyl $C_{1-6}$ alkoxy group, a $C_{1-6}$ alkylthio group, a $C_{3-8}$ cycloalkyl $C_{1-6}$ alkylthio group, a mono-$C_{1-6}$ alkylamino group, a mono-$C_{2-6}$ alkenylamino group, a mono-$C_{2-6}$ alkynylamino group, a mono-$C_{3-8}$ cycloalkylamino group, a mono-$C_{3-8}$ cycloalkyl $C_{1-6}$ alkylamino group, a di-$C_{1-6}$ alkylamino group, a $C_{1-6}$ alkylcarbonyl group and a $C_{1-6}$ alkoxy $C_{1-6}$ alkyl group, and each group described in substituent group a may have 1 to 3 arbitrary groups selected from the following substituent group b:

(substituent group b)

a halogen atom, a hydroxyl group, a mercapto group, a cyano group, a $C_{1-6}$ alkyl group, a $C_{6-10}$ aryl group, a 5- to 10-membered heterocyclic group, a $C_{1-6}$ alkoxy group and an aminosulfonyl group, (substituent group c)

a $C_{1-6}$ alkyl group, a $C_{2-6}$ alkenyl group, a $C_{2-6}$ alkynyl group, a $C_{3-8}$ cycloalkyl $C_{1-6}$ alkyl group, a $C_{6-10}$ aryl $C_{1-6}$ alkyl group, a 5- to 10-membered heterocyclic $C_{1-6}$ alkyl group, a $C_{1-6}$ alkoxy group, a $C_{2-6}$ alkenyloxy group, a $C_{2-6}$ alkynyloxy group, a $C_{5-10}$ aryloxy group, a $C_{3-8}$ cycloalkyl $C_{1-6}$ alkoxy group, a $C_{6-10}$ aryl $C_{1-6}$ alkoxy group, a $C_{6-10}$ aryloxy $C_{1-6}$ alkoxy group, a 5- to 10-membered heterocyclic $C_{1-6}$ alkoxy group, a $C_{1-6}$ alkoxy $C_{1-6}$ alkoxy group, a mono-$C_{6-10}$ arylamino group, a mono-$C_{6-10}$ aryl $C_{1-6}$ alkylamino group, a $C_{6-10}$ aryloxy $C_{1-6}$ alkyl group, a $C_{1-6}$ alkoxy $C_{1-6}$ alkyl group and a 5- to 10-membered heterocycloxy $C_{1-6}$ alkyl group, and each group described in substituent group c may have 1 to 3 groups selected from the group consisting of a halogen atom, a $C_{1-6}$ alkyl group and a $C_{1-6}$ alkoxy group]

[2]: the compound, or the salt or the hydrate thereof according to item [1], wherein $R^1$ represents a hydrogen atom, an amino group or a $C_{1-6}$ alkoxy $C_{1-6}$ alkyl group;

[3]: the compound, or the salt or the hydrate thereof according to item [1], wherein $R^1$ represents a hydrogen atom, an amino group or a methoxymethyl group;

[4]: the compound, or the salt or the hydrate thereof according to any one of items [1] to [3], wherein $R^2$ and $R^3$ independently represents a hydrogen atom, a halogen atom or an arbitrary group selected from substituent group c-1;

[(substituent group c-1)

a $C_{1-6}$ alkyl group, a $C_{6-10}$ aryl $C_{1-6}$ alkyl group, a $C_{1-6}$ alkoxy group, a $C_{2-6}$ alkenyloxy group, a $C_{2-6}$ alkynyloxy group, a $C_{6-10}$ aryloxy group, a $C_{3-8}$ cycloalkyl $C_{1-6}$ alkoxy group, a $C_{6-10}$ aryl $C_{1-6}$ alkoxy group, a $C_{6-10}$ aryloxy $C_{1-6}$ alkoxy group, a 5- to 10-membered heterocyclic $C_{1-6}$ alkoxy group, a $C_{1-6}$ alkoxy $C_{1-6}$ alkoxy group and a $C_{1-6}$ alkoxy $C_{1-6}$ alkyl group, and each group described in substituent group c-1 may have 1 to 3 groups selected from the group consisting of a halogen atom, a $C_{1-6}$ alkyl group and a $C_{1-6}$ alkoxy group]

[5]: the compound, or the salt or the hydrate thereof according to any one of items [1] to [3], wherein $R^2$ and $R^3$ independently represents a hydrogen atom, a halogen atom or an arbitrary group selected from substituent group c-2;

[(substituent group c-2)

a butyl group, a benzyl group, a methoxy group, an ethoxy group, a propoxy group, a butoxy group, a pentyloxy group, an isobutoxy group, a 4-methylbutoxy group, a 2-methylbutoxy group, a 2,2-dimethylpropoxy group, an allyloxy group, a 3-methyl-but-2-enyloxy group, a but-2-enyloxy group, a prop-2-ynyloxy group, a but-2-ynyloxy group, a phenoxy group, a cyclopropylmethoxy group, a phenoxyethoxy group, a benzyloxy group, a 2-fluoro-benzyloxy group, a 3-fluoro-benzyloxy group, a 4-fluoro-benzyloxy group, a 2-chloro-benzyloxy group, a tetrahydropyran-2-ylmethoxy group, a 2-pyridylmethoxy group, a 3-pyridylmethoxy group, a 4-pyridylmethoxy group, a methoxyethoxy group, an ethoxyethoxy group, a methoxymethyl group and an ethoxymethyl group]

[6]: the compound, or the salt or the hydrate thereof according to item [4] or [5], wherein only one of $R^2$ and $R^3$ is a hydrogen atom;

[7]: the compound, or the salt or the hydrate thereof according to any one of items [1] to [6], wherein a bonding position of $R^1$ is a position represented by the partial structure of the following formula (II);

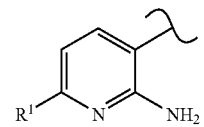
(II)

[8]: the compound, or the salt or the hydrate thereof according to any one of items [1] to [7], wherein bonding positions of $R^2$ and $R^3$ are the positions represented by the partial structure of the following formula (III);

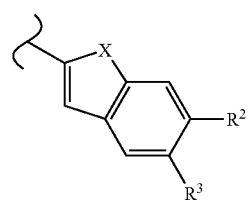
(III)

[9]: the compound, or the salt or the hydrate thereof according to any one of items [1] to [8], wherein X represents an oxygen atom;

[10]: a compound selected from the group consisting of the following compounds, or a salt or a hydrate thereof:

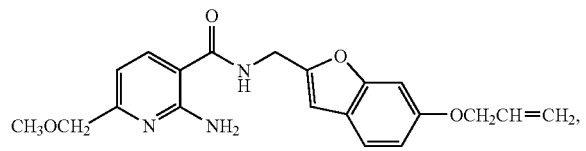

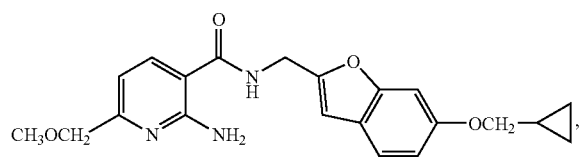

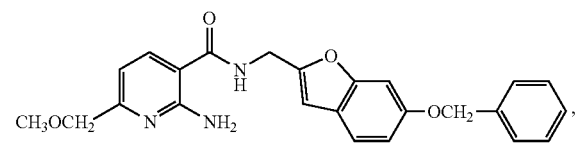

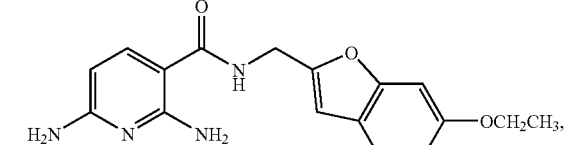

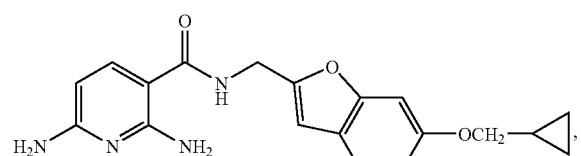

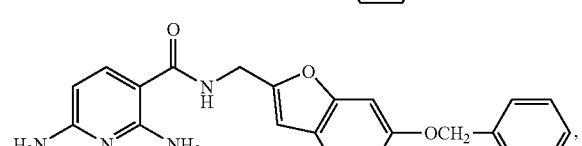

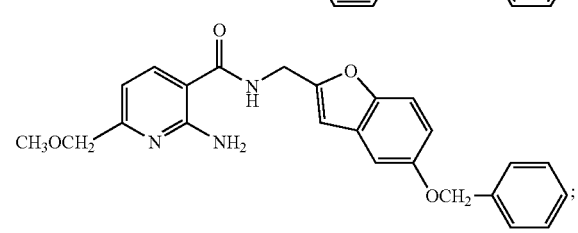

[11]: a pharmaceutical composition comprising the compound, or the salt or the hydrate thereof according to any one of items [1] to [10];

[12]: a medicament comprising the compound, or the salt or the hydrate thereof according to any one of items [1] to [10];

[13]: an antifungal agent comprising, as an active ingredient, the compound, or the salt or the hydrate thereof according to any one of items [1] to [10];

[14]: a method for preventing and/or treating a fungal infection by administering a pharmacologically effective amount of the compound, or the salt or the hydrate thereof according to any one of items [1] to [10];

[15]: a use of the compound, or the salt or the hydrate thereof according to any one of items [1] to [10], for manufacturing an antifungal agent.

ADVANTAGEOUS EFFECTS OF THE INVENTION

Pyridine derivatives (I) according to the present invention, or salts or hydrates thereof, 1) demonstrate effects against the onset, progression and prolongation of infections by preventing the pathogens from demonstrating pathogenicity by inhibiting the expression of cell wall surface layer protein and inhibiting the cell wall assembly together with inhibiting the adherence of fungi to cells, and 2) is superior in terms of physical properties, safety and metabolic stability, and extremely useful as a preventive or therapeutic agent for fungal infections.

BEST MODE FOR CARRYING OUT THE INVENTION

The following defines the symbols, terms and the like described in the present specification, and provides a detailed explanation of the present invention by showing embodiments thereof.

In the present specification, although the structural formulas of compounds may represent a certain isomer for the sake of convenience, all isomers such as geometrical isomers, optical isomers based on asymmetric carbons, stereoisomers, rotamers and tautomers capable of structurally occurring for a compound as well as isomeric mixtures are included in the present invention, are not limited to the descriptions of formulas provided for the sake of convenience, and may be a single isomer or a mixture thereof. Thus, although optical isomers and racemates may be present in the compounds according to the present invention as a result of having asymmetric carbons in a molecule thereof, these are not limited in the present invention, and all such optical isomers and racemates are included therein. In addition, although crystal polymorphism may also be present, this is similarly not limited, and crystals may have a single crystal form or a mixture composed of two or more crystal forms. Solvates such as anhydrides and hydrates are included in the compounds according to the present invention.

In addition, compound formed as a result of the compounds according to the present invention being subjected to metabolism in the body such as oxidation, reduction, hydrolysis or conjugation (so-called metabolites) and compounds that form the compounds according to the present invention as a result of being subjected to metabolism in the body such as oxidation, reduction, hydrolysis or conjugation (so-called prodrugs) are also included within the scope of the present invention.

The term "$C_{1-6}$ alkyl group" used in the present specification refers to a monovalent, linear or branched alkyl group having 1 to 6 carbon atoms derived by removing a single arbitrary hydrogen atom from an aliphatic hydrocarbon having 1 to 6 carbon atoms; specific examples of which include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a neopentyl group, a 1-methylbutyl group, a 2-methylbutyl group, a 1,1-dimethylpropyl group, a 1,2-dimethylpropyl group, a n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group or the like. Preferable examples include a methyl group, an ethyl group, a n-propyl group, an isopropyl group, a n-butyl group, an isobutyl group, a sec-butyl group, a tert-butyl group or the like.

The term "$C_{2-6}$ alkenyl group" used in the present specification refers to a linear or branched alkenyl group having 2 to 6 carbons that may contain 1 to 2 double bonds; specific examples of which include an ethenyl group, a 1-propenyl group, a 2-propenyl group, a 1-butenyl group, a 2-butenyl group, a 3-butenyl group, a 2-methyl-1-propenyl group, a pentenyl group, a 3-methyl-2-butenyl group, a hexenyl group, a hexanedienyl group or the like. Preferable examples include an ethenyl group, a 1-propenyl group, a 2-propenyl group, a 1-butenyl group, a 2-butenyl group, a 3-butenyl group, a 2-methyl-1-propenyl group, a 3-methyl-2-butenyl group or the like.

The term "$C_{2-6}$ alkynyl group" used in the present specification refers to a linear or branched alkynyl group having 2 to 6 carbon atoms that may contain 1 to 2 triple bonds; specific examples of which include an ethynyl group, a 1-propynyl group, a 2-propynyl group, a 1-butynyl group, a 2-butynyl group, a 3-butynyl group, a pentynyl group, a hexynyl group, a hexanediynyl group or the like. Preferable examples include an ethynyl group, a 1-propynyl group, a 2-propynyl group, a 1-butynyl group, a 2-butynyl group, a 3-butynyl group or the like.

The term "$C_{3-8}$ cycloalkyl group" used in the present specification refers to a cyclic aliphatic hydrocarbon group having 3 to 8 carbon atoms; specific examples of which include a cyclopropyl group, a cyclobutyl group, a cyclopentyl group, a cyclohexyl group, a cycloheptyl group, a cyclooctyl group or the like. Preferable examples include a cyclopropyl group, a cyclobutyl group, a cyclopentyl group, a cyclohexyl group or the like.

The term "$C_{1-6}$ alkoxy group" used in the present specification refers to a group in which an oxygen atom is bonded to the end of the previously defined "$C_{1-6}$ alkyl group"; specific examples of which include a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a neopentyloxy group, a 1-methylbutoxy group, a 2-methylbutoxy group, a 1,1-dimethylpropoxy group, a 1,2-dimethylpropoxy group, a n-hexyloxy group, an isohexyloxy group, a 1-methylpentyloxy group, a 2-methylpentyloxy group, a 3-methylpentyloxy group, a 1,1-dimethylbutoxy group, a 1,2-dimethylbutoxy group, a 2,2-dimethylbutoxy group, a 1,3-dimethylbutoxy group, a 2,3-dimethylbutoxy group, a 3,3-dimethylbutoxy group, a 1-ethylbutoxy group, a 2-ethylbutoxy group, a 1,1,2-trimethylpropoxy group, a 1,2,2-trimethylpropoxy group, a 1-ethyl-1-methylpropoxy group, a 1-ethyl-2-methylpropoxy group or the like. Preferable examples include a methoxy group, an ethoxy group, a n-propoxy group, an isopropoxy group, a n-butoxy group, an isobutoxy group, a sec-butoxy group, a tert-butoxy group or the like.

The term "$C_{1-6}$ alkylthio group" used in the present specification refers to a group in which a sulfur atom is bonded to the end of the previously defined "$C_{1-6}$ alkyl group"; specific examples of which include a methylthio group, an ethylthio group, a n-propylthio group, an isopropylthio group, a n-butylthio group, an isobutylthio group, a sec-butylthio group, a tert-butylthio group, a n-pentylthio group, an isopentylthio group, a sec-pentylthio group, a neopentylthio group, a 1-methylbutylthio group, a 2-methylbutylthio group, a 1,1-dimethylpropylthio group, a 1,2-dimethylpropylthio group, a n-hexylthio group, an isohexylthio group, a 1-methylpentylthio group, a 2-methylpentylthio group, a 3-methylpentylthio group, a 1,1-dimethylbutylthio group, a 1,2-dimethylbutylthio group, a 2,2-dimethylbutylthio group, a 1,3-dimethylbutylthio group, a 2,3-dimethylbutylthio group, a 3,3-dimethylbutylthio group, a 1-ethylbutylthio group, a 2-ethylbutylthio group, a 1,1,2-trimethylpropylthio group, a 1,2,2-trimethylpropylthio group, a 1-ethyl-1-methylpropylthio group, a 1-ethyl-2-methylpropylthio group or the like. Preferable examples include a methylthio group, an ethylthio group, a n-propylthio group, an isopropylthio group, a n-butylthio group, an isobutylthio group, a sec-butylthio group, a tert-butylthio group or the like.

The term "$C_{1-6}$ alkylcarbonyl group" used in the present specification refers to a group in which a carbonyl group is bonded to the end of the previously defined "$C_{1-6}$ alkyl group"; specific examples of which include a methylcarbonyl group, an ethylcarbonyl group, a n-propylcarbonyl group, an isopropylcarbonyl group or the like.

The term "$C_{2-6}$ alkenyloxy group" used in the present specification refers to a group in which an oxygen atom is bonded to the end of the previously defined "$C_{2-6}$ alkenyl group"; specific examples of which include an ethenyloxy group, a 1-propenyloxy group, a 2-propenyloxy group, a 1-butenyloxy group, a 2-butenyloxy group, a 3-butenyloxy group, a 2-methyl-1-propenyloxy group, a pentenyloxy group, a 3-methyl-2-butenyloxy group, a hexenyloxy group, a hexanedienyloxy group or the like. Preferable examples include an ethenyloxy group, a 1-propenyloxy group, a 2-propenyloxy group, a 1-butenyloxy group, a 2-butenyloxy group, a 3-butenyloxy group, a 2-methyl-1-propenyloxy group, a 3-methyl-2-butenyloxy group or the like.

The term "$C_{2-6}$ alkynyloxy group" used in the present specification refers to a group in which an oxygen atom is bonded to the end of the previously defined "$C_{2-6}$ alkynyl group"; specific examples of which include an ethynyloxy group, a 1-propynyloxy group, a 2-propynyloxy group, a 1-butynyloxy group, a 2-butynyloxy group, a 3-butynyloxy group, a pentynyloxy group, a hexynyloxy group, a hexanediynyl group or the like. Preferable examples include an ethynyloxy group, a 1-propynyloxy group, a 2-propynyloxy group, a 1-butynyloxy group, a 2-butynyloxy group, a 3-butynyloxy group or the like.

The term "$C_{3-8}$ cycloalkoxy group" used in the present specification refers to a group in which an oxygen atom is bonded to the end of the previously defined "$C_{3-8}$ cycloalkyl group"; specific examples of which include a cyclopropoxy group, a cyclobutoxy group, a cyclopentyloxy group, a cyclohexyloxy group, a cycloheptyloxy group, a cyclooctyloxy group or the like. Preferable examples include a cyclopropoxy group, a cyclobutoxy group, a cyclopentyloxy group, a cyclohexyloxy group or the like.

The term "$C_{3-8}$ cycloalkyl $C_{1-6}$ alkyl group" used in the present specification refers to a group in which an arbitrary hydrogen atom of the previously defined "$C_{1-6}$ alkyl group" is replaced with the previously defined "$C_{3-8}$ cycloalkyl group"; specific examples of which include a cyclopropylmethyl group, a cyclobutylmethyl group, a cyclopentylmethyl group, a cyclohexylmethyl group, a cyclopropylethyl group, a cyclobutylethyl group, a cyclopentylethyl group, a cyclohexylethyl group or the like.

The term "$C_{3-8}$ cycloalkyl $C_{1-6}$ alkoxy group" used in the present specification refers to a group in which an arbitrary hydrogen atom of the previously defined "$C_{1-6}$ alkoxy group"

is replaced with the previously defined "$C_{3-8}$ cycloalkyl group"; specific examples of which include a cyclopropylmethoxy group, a cyclobutylmethoxy group, a cyclopentylmethoxy group, a cyclohexylmethoxy group, a cyclopropylethoxy group, a cyclobutylethoxy group, a cyclopentylethoxy group, a cyclohexylethoxy group or the like.

The term "$C_{3-8}$ cycloalkyl $C_{1-6}$ alkylthio group" used in the present specification refers to a group in which an arbitrary hydrogen atom of the previously defined "$C_{1-6}$ alkylthio group" is replaced with the previously defined "$C_{3-8}$ cycloalkyl group"; specific examples of which include a cyclopropylmethylthio group, a cyclobutylmethylthio group, a cyclopentylmethylthio group, a cyclohexylmethylthio group, a cyclopropylethylthio group, a cyclobutylethylthio group, a cyclopentylethylthio group, a cyclohexylethylthio group or the like.

The term "$C_{6-10}$ aryl group" used in the present specification refers to an aromatic hydrocarbon cyclic group having 6 to 10 carbon atoms; specific examples of which include a phenyl group, a 1-naphthyl group, a 2-naphthyl group, an indenyl group, an azulenyl group, a heptalenyl group or the like. Preferable examples include a phenyl group, a 1-naphthyl group, a 2-naphthyl group or the like.

The term "$C_{6-10}$ aryloxy group" used in the present specification refers to a group in which an oxygen atom is bonded to the end of the previously defined "$C_{6-10}$ aryl group"; specific examples of which include a phenoxy group, a 1-naphthyloxy group, a 2-naphthyloxy group, an indenyloxy group, an azulenyloxy group, a heptalenyloxy group or the like. Preferable examples include a phenoxy group, a 1-naphthyloxy group, a 2-naphthyloxy group or the like.

The "$C_{6-10}$ aryl $C_{1-6}$ alkyl group" used in the present specification refers to a group in which an arbitrary hydrogen atom of the previously defined "$C_{1-6}$ alkyl group" is replaced with the previously defined "$C_{6-10}$ aryl group"; specific examples of which include a benzyl group, a 1-naphthylmethyl group, a 2-naphthylmethyl group, a phenethyl group, a 1-naphthylethyl group, a 2-naphthylethyl group, a 3-phenyl-1-propyl group or the like.

The "$C_{6-10}$ aryloxy $C_{1-6}$ alkyl group" used in the present specification refers to a group in which an arbitrary hydrogen atom of the previously defined "$C_{1-6}$ alkyl group" is replaced with the previously defined "$C_{6-10}$ aryloxy group"; specific examples of which include a phenoxymethyl group, a 1-napthyloxymethyl group, a 2-naphthyloxymethyl group, an indenyloxymethyl group, an azulenyloxymethyl group, a heptalenyloxymethyl group or the like. Preferable examples include a phenoxymethyl group, a 1-naphthyloxymethyl group, a 2-naphthyloxymethyl group or the like.

The term "$C_{1-6}$ alkoxy $C_{1-6}$ alkyl group" used in the present specification refers to a group in which an arbitrary hydrogen atom of the previously defined "$C_{1-6}$ alkyl group" is replaced with the previously defined "$C_{1-6}$ alkoxy group"; specific examples of which include a methoxymethyl group, an ethoxymethyl group, a n-propoxymethyl group, a methoxyethyl group, an ethoxyethyl group or the like.

The term "$C_{1-6}$ alkoxy $C_{1-6}$ alkoxy group" used in the present specification refers to a group in which an arbitrary hydrogen atom of the previously defined "$C_{1-6}$ alkoxy group" is replaced with the previously defined "$C_{1-6}$ alkoxy group"; specific examples of which include a methoxymethoxy group, an ethoxymethoxy group, a n-propoxymethoxy group, a methoxyethoxy group, an ethoxyethoxy group, a methoxypropoxy group or the like.

The term "$C_{6-10}$ aryl $C_{1-6}$ alkoxy group" used in the present specification refers to a group in which an arbitrary hydrogen atom of the previously defined "$C_{1-6}$ alkoxy group" is replaced with the previously defined "$C_{6-10}$ aryl group"; specific examples of which include a benzyloxy group, a 1-naphthylmethoxy group, a 2-naphthylmethoxy group, a phenethyloxy group, a 1-naphthylethoxy group, a 2-naphthylethoxy group, a 3-phenyl-1-propoxy group or the like.

The term "$C_{6-10}$ aryloxy $C_{1-6}$ alkoxy group" used in the present specification refers to a group in which an arbitrary hydrogen atom of the previously defined "$C_{1-6}$ alkoxy group" is replaced with the previously defined "$C_{6-10}$ aryloxy group"; specific examples of which include a phenoxymethoxy group, a 1-naphthyloxymethoxy group, a 2-naphthyloxymethoxy group, a phenoxyethoxy group, a 1-naphthyloxyethoxy group, a 2-naphthyloxyethoxy group, a 3-phenoxy-1-propoxy group or the like.

The term "mono-$C_{1-6}$ alkylamino group" used in the present specification refers to a group in which one hydrogen atom in an amino group is replaced with the previously defined "$C_{1-6}$ alkyl group"; specific examples of which include a methylamino group, an ethylamino group, a n-propylamino group, an isopropylamino group, a n-butylamino group, an isobutylamino group, a sec-butylamino group, a tert-butylamino group, a n-pentylamino group, an isopentylamino group, a sec-pentylamino group, a neopentylamino group, a 1-methylbutylamino group, a 2-methylbutylamino group, a 1,1-dimethylpropylamino group, a 1,2-dimethylpropylamino group, a n-hexylamino group, an isohexylamino group, a 1-methylpentylamino group, a 2-methylpentylamino group, a 3-methylpentylamino group, a 1,1-dimethylbutylamino group, a 1,2-dimethylbutylamino group, a 2,2-dimethylbutylamino group, a 1,3-dimethylbutylamino group, a 2,3-dimethylbutylamino group, a 3,3-dimethylbutylamino group, a 1-ethylbutylamino group, a 2-ethylbutylamino group, a 1,1,2-trimethylpropylamino group, a 1,2,2-trimethylpropylamino group, a 1-ethyl-1-methylpropylamino group, a 1-ethyl-2-methylpropylamino group or the like. Preferable examples include a methylamino group, an ethylamino group, a n-propylamino group, an isopropylamino group, a n-butylamino group, an isobutylamino group, a sec-butylamino group, a tert-butylamino group or the like.

The term "mono-$C_{2-6}$ alkenylamino group" used in the present specification refers to a group in which one hydrogen atom in an amino group is replaced with the previously defined "$C_{2-6}$ alkenyl group"; specific examples of which include an ethenylamino group, a 1-propenylamino group, a 2-propenylamino group, a 1-butenylamino group, a 2-butenylamino group, a 3-butenylamino group, a 2-methyl-1-propenylamino group, a pentenylamino group, a 3-methyl-2-butenylamino group, a hexenylamino group, a hexanedienylamino group or the like. Preferable examples include an ethenylamino group, a 1-propenylamino group, a 2-propenylamino group, a 1-butenylamino group, a 2-butenylamino group, a 3-butenylamino group, a 2-methyl-1-propenylamino group, a 3-methyl-2-heptenylamino group or the like.

The term "mono-$C_{2-6}$ alkynylamino group" used in the present specification refers to a group in which one hydrogen atom in an amino group is replaced with the previously defined "$C_{2-6}$ alkynyl group"; specific examples of which include an ethynylamino group, a 1-propynylamino group, a 2-propynylamino group, a 1-butynylamino group, a 2-butynylamino group, a 3-butynylamino group, a pentynylamino group, a hexynylamino group, a hexanediynyl group or the like. Preferable examples include an ethynylamino group, a 1-propynylamino group, a 2-propynylamino group, a 1-butynylamino group, a 2-butynylamino group, a 3-butynylamino group or the like.

The "mono-$C_{3-8}$ cycloalkylamino group" used in the present specification refers to a group in which one hydrogen atom in an amino group is replaced with the previously defined "$C_{3-8}$ cycloalkyl group"; specific examples of which include a cyclopropylamino group, a cyclobutylamino group, a cyclopentylamino group, a cyclohexylamino group, a cycloheptylamino group, a cyclooctylamino group or the like. Preferable examples include a cyclopropylamino group, a cyclobutylamino group, a cyclopentylamino group, a cyclohexylamino group or the like.

The term "mono-$C_{6-10}$ arylamino group" used in the present specification refers to a group in which one hydrogen atom in an amino group is replaced with the previously defined "$C_{6-10}$ aryl group"; specific examples of which include a phenylamino group, a 1-naphthylamino group, a 2-naphthylamino group, an indenylamino group, an azulenylamino group, a heptalenylamino group or the like. Preferable examples include a phenylamino group, a 1-naphthylamino group, a 2-naphthylamino group or the like.

The "mono-$C_{3-8}$ cycloalkyl $C_{1-6}$ alkylamino group" used in the present specification refers to a group in which one hydrogen atom in amino group is replaced with the previously defined "$C_{3-8}$ cycloalkyl $C_{1-6}$ alkyl group"; specific examples of which include a cyclopropylmethylamino group, a cyclobutylmethylamino group, a cyclopentylmethylamino group, a cyclohexylmethylamino group, a cyclopropylethylamino group, a cyclobutylethylamino group, a cyclopentylethylamino group, a cyclohexylethylamino group or the like.

The term "mono-$C_{6-10}$ aryl $C_{1-6}$ alkylamino group" used in the present specification refers to a group in which one hydrogen atom in an amino group is replaced with the previously defined "$C_{6-10}$ aryl $C_{1-6}$ alkyl group"; specific examples of which include a benzylamino group, a 1-naphthylmethylamino group, a 2-naphthylmethylamino group, a phenethylamino group, a 1-naphthylethylamino group, a 2-naphthylethylamino group or the like.

The "di-$C_{1-6}$ alkylamino group" used in the present specification refers to a group in which two hydrogen atoms in an amino group are respectively replaced with the same or different previously defined "$C_{1-6}$ alkyl group"; specific examples of which include a N,N-dimethylamino group, a N,N-diethylamino group, a N,N-di-n-propylamino group, a N,N-di-isopropylamino group, a N,N-di-n-butylamino group, a N,N-di-isobutylamino group, a N,N-di-sec-butylamino group, a N,N-di-tert-butylamino group, a N-ethyl-N-methylamino group, a N-n-propyl-N-methylamino group, a N-isopropyl-N-methylamino group, a N-n-butyl-N-methylamino group, a N-isobutyl-N-methylamino group, a N-sec-butyl-N-methylamino group, a N-tert-butyl-N-methylamino group or the like. Preferable examples include a N,N-dimethylamino group, a N,N-diethylamino group, a N-ethyl-N-methylamino group or the like.

The term "halogen atom" used in the present specification refers to a fluorine atom, a chlorine atom, a bromine atom or an iodine atom, preferably a fluorine atom, a chlorine atom or a bromine atom.

The term "heteroatom" used in the present specification refers to a nitrogen atom, sulfur atom or oxygen atom.

The term "5- to 10-membered heterocyclic group" used in the present specification refers to a monovalent group having 5 to 10 atoms that compose an aromatic or non-aromatic ring derived by removing a hydrogen atom from the ring that contains one to a plurality of heteroatoms among the atoms that compose the ring. Specific examples of aromatic "5- to 10-membered heterocyclic groups" include furyl groups (such as a 2-furyl or 3-furyl group), thienyl groups (such as a 2-thienyl or 3-thienyl group), pyrrolyl groups (such as a 1-pyrrolyl, 2-pyrrolyl or 3-pyrrolyl group), pyridyl groups (such as a 2-pyridyl, 3-pyridyl or 4-pyridyl group), a pyradinyl group and pyradazinyl groups (such as a 3-pyradazinyl or 4-pyradazinyl group), pyrmidinyl groups (such as a 2-pyrimidinyl, 4-pyrimidinyl or 5-pyrimidinyl group), triazolyl groups (such as a 1,2,3-triazolyl or 1,2,4-triazolyl group), tetrazolyl groups (such as a 1H-tetrazolyl or 2H-tetrazolyl group), thiazolyl groups (such as a 2-thiazolyl, 4-thiazolyl or 5-thiazolyl group), pyrazolyl groups (such as a 3-pyrazolyl or 4-pyrazolyl group), oxazolyl groups (such as a 2-oxazolyl, 4-oxazolyl or 5-oxazolyl group), isoxazolyl groups (such as a 3-isoxazolyl, 4-isoxazolyl or 5-isoxazolyl group), isothiazolyl groups (such as a 3-isothiazolyl, 4-isothiazolyl or 5-isothiazolyl group), quinolyl groups (such as a 5-quinolyl, 6-quinolyl, 7-quinolyl or 8-quinolyl group), isoquinolyl groups (such as a 5-isoquinolyl, 6-isoquinolyl, 7-isoquinolyl or 8-isoquinolyl group), naphthylidinyl groups (such as a [1,5]naphthylidin-2-yl, [1,5]naphthylidin-3-yl, [1,8]naphthylidin-2-yl or [1,8]naphthylidin-3-yl group), quinoxalinyl groups (such as a 5-quinoxalinyl, 6-quinoxalinyl, 7-quinoxalinyl or 8-quinoxalinyl group), cinnolinyl groups (such as a 5-cinnolinyl, 6-cinnolinyl, 7-cinnolinyl or 8-cinnolinyl group), quinazolinyl groups (such as a 4-quinazolinyl, 5-quinazolinyl, 6-quinazolinyl, 7-quinazolinyl or 8-quinazolinyl group), imidazopyridyl groups (such as an imidazo[1,2-a]pyridin-6-yl group), benzothiazolyl groups (such as a benzothiazol-4-yl, benzothiazol-5-yl, benzothiazol-6-yl or benzothiazol-7-yl group), benzoxazolyl groups (such as a benzoxazoly-4-yl, benzoxazol-5-yl, benzoxazol-6-yl or benzoxazol-7-yl group), benzoimidazolyl groups (such as a benzoimidazol-4-yl, benzoimidazol-5-yl, benzoimidazol-6-yl or benzoimidazol-7-yl group), indolyl groups (such as an indol-4-yl, indol-5-yl, indol-6-yl or indol-7-yl group), pyrrolopyridyl groups (such as a 1H-pyrrolo[2,3-b]pyridin-5-yl group or pyrrolo[3,2-b]pyridin-1-yl group), thienopyridyl groups (such as a thieno[2,3-b]pyridin-5-yl or thieno[3,2-b]pyridin-6-yl group), furopyridyl groups (such as a furu[2,3-b]pyridin-5-yl or furu[3,2-b]pyridin-6-yl group), 2,3-dihydro-1H-pyrrolo[2,3-b]pyridin-5-yl group, benzothiadiazolyl groups (such as a benzo[1,2,5]thiadiazol-5-yl group), benzoxadiazolyl groups (such as a benzo[1,2,5]oxadiazol-5-yl group), pyridopyrimidinyl groups (such as a pyrido[2,3-d]pyrimidin-4-yl group), benzofuryl groups (such as a benzofuran-4-yl, benzofuran-5-yl, benzofuran-6-yl or benzofuran-7-yl group), benzothienyl groups (such as a benzothiophen-4-yl, benzothiophen-5-yl, benzothiophen-6-yl or benzothiophen-7-yl group), benzo[1,3]dioxazole groups (such as a benzo[1,3]dioxol-5-yl group) or the like. Specific examples of the non-aromatic "5- to 10-membered heterocyclic groups" include a pyrrolidinyl group, a piperidinyl group, a homopiperidinyl group, a piperazinyl group, a homopiperazinyl group, a morpholinyl group, a thiomorpholinyl group, a tetrahydrofuryl group, a tetrahydropyranyl group or the like.

The term "5- to 10-membered heterocyclic $C_{1-6}$ alkyl group" used in the present specification refers to a group in which an arbitrary hydrogen atom in the previously defined "$C_{1-6}$ alkyl group" is replaced with the previously defined "5- to 10-membered heterocyclic group"; specific examples of which include a furylmethyl group, a thienylmethyl group, a pyrrolylmethyl group, a pyridylmethyl group, a triazolylmethyl group, a tetrazolylmethyl group, a thiazolylmethyl group, a pyrazolylmethyl group, an oxazolylmethyl group, a benzo[1,3]dioxolmethyl group, a tetrahydrofurylmethyl group, a furylethyl group, a thienylethyl group, a pyrrolylethyl group, a pyridylethyl group, a triazolylethyl group, a tetrazolylethyl group, a thiazolylethyl group, a pyrazolylethyl group, an oxazolylethyl group, a benzo[1,3]dioxolethyl group, a tetrahydrofurylethyl group or the like.

The term "5- to 10-membered heterocycloxy group" used in the present specification refers to a group in which an oxygen atom is bonded to the end of the previously defined "5- to 10-membered heterocyclic group"; specific examples of which include a furyloxy group, a thienyloxy group, a pyrrolyloxy group, a pyridyloxy group, a triazolyloxy group, a tetrazolyloxy group, a thiazolyloxy group, a pyrazolyloxy group, an oxazolyloxy group, a benzo[1,3]dioxoloxy group, a tetrahydrofuryloxy group or the like.

The "5- to 10-membered heterocyclic $C_{1-6}$ alkoxy group" used in the present specification refers to a group in which an arbitrary hydrogen atom in the previously defined "$C_{1-6}$ alkoxy group" is replaced with the previously defined "5- to 10-membered heterocyclic group"; specific examples of which include a furylmethoxy group, a thienylmethoxy group, a pyrrolylmethoxy group, a pyridylmethoxy group, a triazolylmethoxy group, a tetrazolylmethoxy group, a thiazolylmethoxy group, a pyrazolylmethoxy group, an oxazolylmethoxy group, a benzo[1,3]dioxolmethoxy group, a tetrahydrofurylmethoxy group, a furylethoxy group, a thienylethoxy group, a pyrrolylethoxy group, a pyridylethoxy group, a triazolylethoxy group, a tetrazolylethoxy group, a thiazolylethoxy group, a pyrazolylethoxy group, an oxazolylethoxy group, a benzo[1,3]dioxolethoxy group, a tetrahydrofurylethoxy group or the like.

The term "5- to 10-membered heterocycloxy $C_{1-6}$ alkyl group" used in the present specification refers to a group in which an arbitrary hydrogen atom in the previously defined "$C_{1-6}$ alkyl group" is replaced with the previously defined "5- to 10-membered heterocycloxy group", specific examples of which include a furyloxymethyl group, a thienyloxymethyl group, a pyrrolyloxymethyl group, a pyridyloxymethyl group, a triazolyloxymethyl group, a tetrazolyloxymethyl group, a thiazolyloxymethyl group, a pyrazolyloxymethyl group, an oxazolyloxymethyl group, a benzo[1,3]dioxoloxymethyl group, a tetrahydrofuryloxymethyl group, a furyloxyethyl group, a thienyloxyethyl group, a pyrrolyloxyethyl group, a pyridyloxyethyl group, a triazolyloxyethyl group, a tetrazolyloxyethyl group, a thiazolyloxyethyl group, a pyrazolyloxyethyl group, an oxazolyloxyethyl group, a benzo[1,3]dioxoloxyethyl group, a tetrahydrofuryloxyethyl group or the like.

The term "may have a substituent" used in the present specification refers to optionally having one or a plurality of substituents arbitrarily combined at a substitutable site.

The term "has a substituent" used in the present specification refers to having one or a plurality of substituents arbitrarily combined at a substitutable site.

X represents an oxygen atom, a sulfur atom or —NH—, and represents particularly preferable an oxygen atom.

$R^1$ preferably represents a hydrogen atom, a halogen atom, a cyano group, an amino group or an arbitrary group selected from the substituent group a, represents particularly preferably a hydrogen atom, an amino group or a $C_{1-6}$ alkoxy $C_{1-6}$ alkyl group, and said $C_{1-6}$ alkoxy $C_{1-6}$ alkyl group preferably represents a methoxymethyl group.

In addition, the bonding site of $R^1$ is preferably a position represented by the partial structure of the following formula (II):

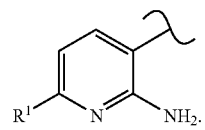

(II)

$R^2$ and $R^3$ independently represent a hydrogen atom, a halogen atom, a hydroxyl group or an arbitrary group selected from the substituent group c, preferably represent a hydrogen atom, a halogen atom, or an arbitrary group selected from the substituent group c-1, and an arbitrary group selected from the substituent group c-1 is preferably a group selected from the substituent group c-2.

In addition, one of $R^2$ and $R^3$ is preferably a hydrogen atom.

Moreover, the bonding positions of $R^2$ and $R^3$ to the benzene ring are preferably positions represented by the partial structure of the following formula:

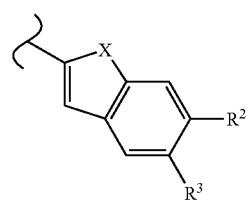

(III)

Specific examples showing the preferable bonding positions include the partial structures represented by the following formulas:

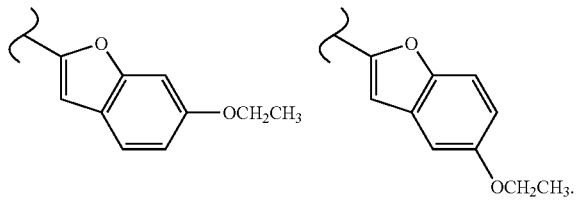

Although preferable specific examples of the compounds according to the present invention include the group of compounds represented by the following formulas, the present invention is not limited to this group of compounds:

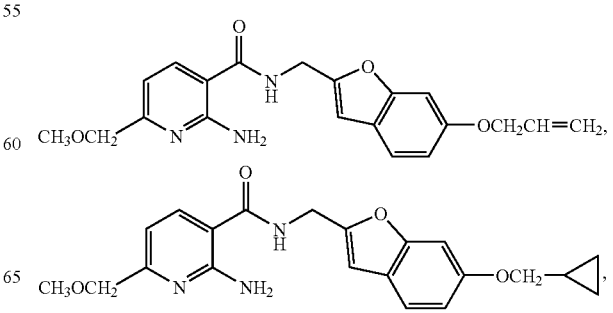

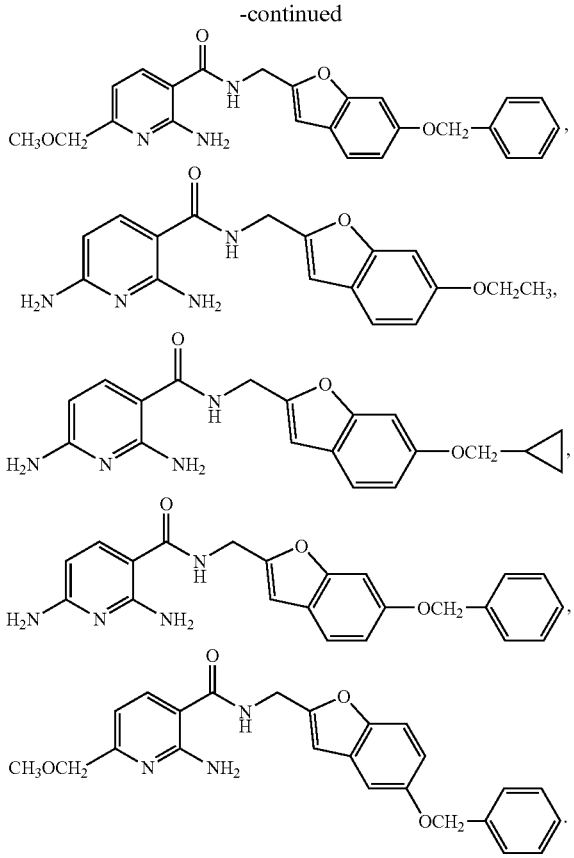

Examples of a "salt" used in the present specification include salts of inorganic acids, salts of organic acids, salts of inorganic bases, salts of organic bases and salts of acidic or basic amino acids, and pharmaceutically acceptable salts are particularly preferable.

Preferable examples of the salts of the inorganic acids include salts of hydrochloric acid, hydrobromic acid, sulfuric acid, nitric acid, phosphoric acid or the like. Preferable examples of salts of the organic acids include salts of acetic acid, succinic acid, fumaric acid, maleic acid, tartaric acid, citric acid, lactic acid, stearic acid, benzoic acid, methanesulfonic acid, ethanesulfonic acid, p-toluenesulfonic acid or the like.

Preferable examples of the salts of the inorganic bases include alkaline metal salts such as sodium salts or potassium salts; alkaline earth metal salts such as calcium salts or magnesium salts; aluminum salts, ammonium salts or the like. Preferable examples of the salts or the organic bases include salts of diethylamine, diethanolamine, meglumine, N,N-dibenzylethyldiamine or the like.

Preferable examples of the salts of the acidic amino acids include salts of aspartic acid or glutamic acid. Preferable examples of the salts of the basic amino acids include salts of arginine, lysine, ornithine or the like.

The term "antifungal agent" used in the present specification refers to a preventive agent and/or therapeutic agent of the fungal infections.

Compounds according to the present invention or salts, or hydrates thereof, can be formulated as, for example, tablets, powders, grains, granules, coated tablets, capsules, syrups, lozenges, inhalants, suppositories, injections, ointments, ophthalmic ointments, tapes, eye drops, nose drops, ear drops, poultices or lotions according to the conventional methods. Commonly used excipients, binders, lubricants, colorants, correctives and, as necessary, stabilizers, emulsifiers, absorption promoters, surfactants, pH adjusters, preservatives, antioxidants and the like can be used for formulation, and are formulated according to the conventional methods by blending components typically used as raw materials of the pharmaceutical preparations. For example, when manufacturing an oral preparation, the compound according to the present invention, or a pharmaceutically acceptable salt thereof, an excipient, and as necessary, a binder, a disintegration agent, a lubricant, a colorant, corrective and the like are added followed by forming into a powder, grains, granules, tablet, coated tablet or capsule and the like in accordance with the conventional methods. Examples of these components include animal and vegetable oils such as soybean oil, beef tallow or synthetic glycerides; hydrocarbons such as liquid paraffin, squalane or solid paraffin; ester oils such as octyldodecyl myristate or isopropyl myristate; higher alcohols such as cetostearyl alcohol or behenyl alcohol; silicon resin; silicon oil; surfactants such as polyoxyethylene fatty acid ester, sorbitan fatty acid ester, glycerin fatty acid ester, polyoxyethylene sorbitan fatty acid ester, polyoxyethylene hydrogenated castor oil or polyoxyethylene polyoxypropylene block copolymer; water-soluble polymers such as hydroxyethyl cellulose, polyacrylic acid, carboxyvinyl polymer, polyethylene glycol, polyvinyl pyrrolidone or methyl cellulose; lower alcohols such as ethanol or isopropanol; polyvalent alcohols such as glycerin, propylene glycol, dipropylene glycol or sorbitol; sugars such as glucose or sucrose; inorganic powders such as silicic anhydride, magnesium aluminum silicate or aluminum silicate; and purified water. Examples of the excipients include lactose, cornstarch, saccharose, glucose, mannitol, sorbitol, crystalline cellulose, silicon dioxide or the like. Examples of the binders include polyvinyl alcohol, polyvinyl ether, methyl cellulose, ethyl cellulose, gum Arabic, tragacanth, gelatin, shellac, hydroxypropyl methyl cellulose, hydroxypropyl cellulose, polyvinyl pyrrolidone, polypropylene glycol-polyoxyethylene glycol block polymer, meglumine or the like. Examples of the disintegration agents include starch, agar, gelatin powder, crystalline cellulose, calcium carbonate, sodium bicarbonate, calcium citrate, dextrin, pectin, calcium carboxymethyl cellulose or the like. Examples of the lubricants include magnesium stearate, talc, polyethylene glycol, silica, hydrogenated vegetable oil or the like. Examples of colorants include those for which addition to pharmaceuticals is allowed, and examples of correctives include cocoa powder, peppermint, aromatic powder, peppermint oil, camphor, cinnamon powder or the like. These tablets and granules may naturally be suitably coated with a sugar coating or other coatings as necessary. In addition, when manufacturing a liquid preparation such as syrup or injection, a pH adjuster, a dissolution agent, an isotonic agent or the like, and as necessary, a dissolution assistant or a stabilizer or the like are added to the compound according to the present invention, or pharmaceutically acceptable salt thereof, followed by formulating in accordance with the conventional methods. There are no limitations on methods used to produce preparations for external use, and these can be produced in accordance with the conventional methods. Namely, examples of base raw materials that can be used during formulation include various raw materials commonly used in pharmaceuticals, over-the-counter medicines, cosmetics and the like. Specific examples of base raw materials used include animal and vegetable oils, mineral oils, ester oils, waxes, polyvalent alcohols, water-soluble polymers, clay minerals and purified water, and although pH adjusters, antioxidants, chelating agents, preservatives, antimold agents, colorants, fragrances and the like can also be added as necessary, the base raw materials of the preparations for external use of the present invention are not limited thereto. In addition, components such as components having differentiation-inducing action, circulation promoters, disinfectants, antiphlogistics, cell activators, vitamins, amino acids, moisturizers or keratin dissolution agents or the like can also be blended as necessary. Furthermore, the amounts of the base raw materials added are those amounts that yield the ordinary set concentrations for production of preparations for external use.

In the case of administering the compound according to the present invention or the salt, or the hydrate thereof, there are no particular limitations on the form thereof, and said compound may be administered by oral administration or parenteral administration in accordance with ordinarily used methods. For example, the compound may be administered after formulating in the form of the tablet, the powder, the granules, the capsule, the syrup, the lozenge, the inhalant, the suppository, the injection, the ointment, the ophthalmic ointment, the tape, the eye drops, the nose drops, the ear drops, the poultice or the lotion.

The dose of the medicament according to the present invention can be suitably selected according to the degree of symptoms, age, gender, body weight, administration form, type of salt, specific type of disease or the like.

Although the dose differs considerably depending on the type of disease, degree of symptoms, patient age and gender, drug sensitivity or the like, in the case of the oral preparation, the normal adult dose is from 1 to 10000 mg per day, preferably from 10 to 2000 mg/day administered in a single dose or divided among several doses. In the case of the injection, the normal adult dose is generally from 0.1 to 10000 mg per day, preferably from 1 to 2000 mg per day.

The following provides the description of the production process for compounds represented by formula (I) (referred to as compound (I) hereinbelow) according to the present invention. Although compounds according to the present invention can be synthesized using the conventional organic synthesis means, they can be produced according to, for example, the typical synthesis method described below.

[Typical Synthesis Method]

[Production Process 1] Typical Production Process of Compound (1a)

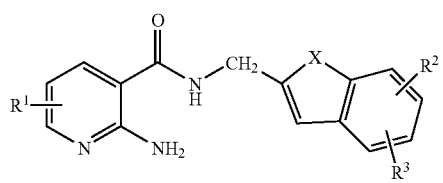

(1a)

[wherein each reference symbol is defined as above.]

[Production Process 1-1] Amidation

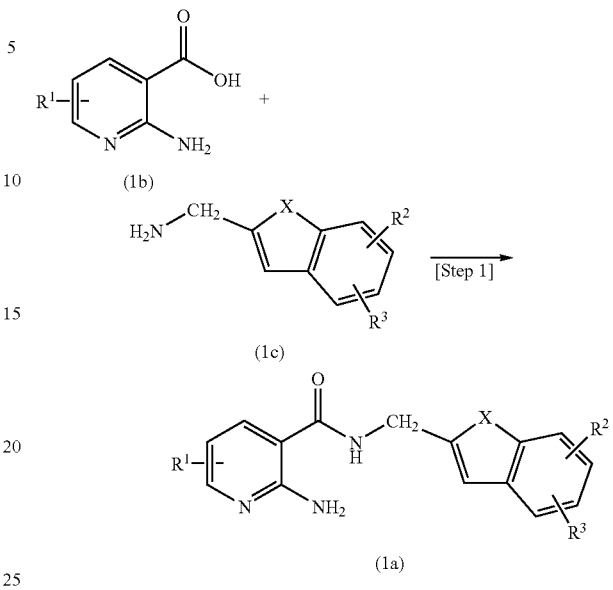

[wherein each reference symbol is defined as above.]

A commercially available product can be used as is for compound (1b) or compound (1b) can be produced from a commercially available product using the known method. Moreover, compound (1b) can also be produced using the method described in the production examples of the examples or [Production Process 1-2-1] and the like.

A commercially available product can be used as is for compound (1c) or compound (1c) can be produced from a commercially available product using the known method. Moreover, compound (1c) can also be produced using a method described in the production examples of the examples or [Production Process 1-3-1] and the like.

[Step 1]

This step is a step for obtaining compound (1a) by condensing compound (1b) and compound (1c) using a condensation agent in a solvent. There are no particular limitations on the solvent used, and examples of solvents used include halogenated hydrocarbons such as dichloromethane or chloroform; sulfoxides such as dimethylsulfoxide; esters such as ethyl acetate; ethers such as tetrahydrofuran or 1,4-dioxane; amides such as N,N-dimethylformamide, N,N-dimethylacetoamide or the like. Examples of the condensation agents include Bop (benzotriazole-1-yl oxytris(dimethylamino) phosphonium hexafluorophosphate), WSC (1-ethyl-3-(3,3-dimethylaminopropyl)carbodiimide hydrochloride), DOC (N,N'-dicyclohexylcarbodiimide), CDI (carbonyldiimidazole), diethyl phosphoryl cyanide or the like. 1 to 1.5 equivalents of compound (1c) are used with respect to compound (1b). 1 to 1.5 equivalents of condensation agent are used with respect to compound (1b). In addition, 1 equivalent to an excess of organic base such as triethylamine may be added as necessary. The reaction temperature is from room temperature to 80° C. and the reaction time is from 10 minutes to 30 hours.

In addition, compound (1a) can also be produced from compound (1b) and compound (1c) using alternative methods described in (1), (2) or (3).

Alternative Method (1): After converting compound (1b) to acid chloride, compound (1a) can be obtained by reacting acid chloride with compound (1c). The step for obtaining the acid chloride is carried out by reacting 1 equivalent to an excess of acid chloride synthesis reagent with compound (1b) in the absence of a solvent or in the presence of a solvent such as dichloromethane, benzene or toluene. A catalytic amount of N,N-dimethylformamide may also be added to the reaction system. Examples of acid chloride synthesis reagents include thionyl chloride, oxalyl chloride, phosphorous trichloride, phosphorous pentachloride or the like. The reaction temperature is from cooling with ice to the reflux temperature, and the reaction time is from 10 minutes to 24 hours.

The step for condensing acid chloride and compound (1c) is carried out by reacting acid chloride with compound (1c) in a solvent such as dichloromethane, tetrahydrofuran or N,N-dimethylformamide and in the presence of 1 to 3 equivalents of base with respect to the acid chloride, examples of which include organic bases such as triethylamine or pyridine and inorganic bases such as potassium carbonate or cesium carbonate. 1 to 1.5 equivalents of compound (1c) are used with respect to acid chloride. The reaction time is 10 minutes to 24 hours and the reaction temperature is 0° C. to the reflux temperature.

Alternative Method (2): After converting compound (1b) to a mixed acid anhydride, compound (1a) can be obtained by reacting the mixed acid anhydride with compound (1c). The step for obtaining the mixed acid anhydride is carried out by reacting compound (1b) with a chloroformic acid ester such as ethyl chloroformate in the presence of a base such as triethylamine. 1 to 2 equivalents of the chloroformic acid ester and base are used with respect to compound (1b). The reaction time is from 10 minutes to 5 hours and the reaction temperature is from 0° C. to room temperature.

The step for condensing the mixed acid anhydride and compound (1c) is carried out by reacting the mixed acid anhydride and compound (1c) in a solvent such as dichloromethane, tetrahydrofuran, N,N-dimethylformamide or the like. 1 to 1.5 equivalents of compound (1c) are used with respect to the mixed acid anhydride. The reaction time is from 10 minutes to 24 hours and the reaction temperature is from 0 to 50° C.

Alternative Method (3): After converting compound (1b) to an active ester, compound (1a) can be obtained by reacting the active ester with compound (1c). The step for obtaining the active ester is carried out by reacting compound (1b) with an active ester synthesis reagent in a solvent such as 1,4-dioxane, tetrahydrofuran or the like and in the presence of a condensation agent such as DCC. Examples of active ester synthesis reagents include N-hydroxysuccinimide or the like. 1 to 1.5 equivalents of the active ester synthesis reagent and the condensation agent are used with respect to compound (1b). The reaction temperature is from 0° C. to room temperature and the reaction time is from 2 to 24 hours.

The step for condensing the active ester and compound (1c) is carried out by reacting the active ester with compound (1c) in a solvent such as dichloromethane, tetrahydrofuran, N,N-dimethylformamide or the like. 1 to 1.5 equivalents of compound (1c) are used with respect to the active ester. The reaction temperature is from 0 to 50° C. and the reaction time is from 10 minutes to 24 hours.

Furthermore, the substituents on the pyridine ring and the heterobicyclic rings of compound (1a) can be converted using the known method following Step 1, substituents on the pyridine ring of compound (1a) can be converted using the method described in Production Process 2-1, Production Process 2-2, Production Process 2-3 or Production Process 2-4, and substituents on the heterobicyclic rings of compound (1a) can be converted using the method described in Production Process 2-5, Production Process 2-6 or Production Process 2-7.

[Production Process 1-2-1] Production Process of Compound (1b)

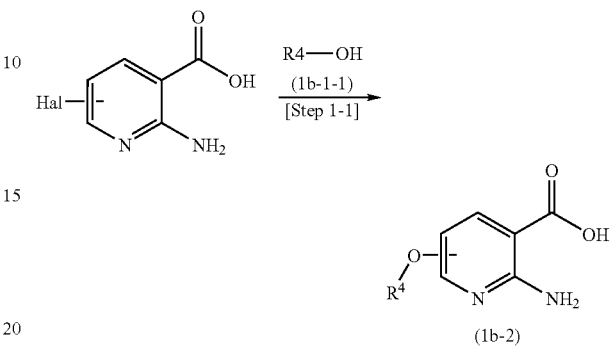

[wherein Hal represents a halogen atom, and $R^4$ represents a $C_{1-6}$ alkyl group, a $C_{2-6}$ alkenyl group, a $C_{2-6}$ alkynyl group, a $C_{3-8}$ cycloalkyl group or a $C_{3-8}$ cycloalkyl $C_{1-6}$ alkyl group.]

Commercially available products can be used as is for each of the compounds in the flow chart above, and each of the compounds can be produced from commercially available products by the known method. In addition, each of the compounds can also be produced using the methods described in the examples.

[Step 1-1]

This step is a step for obtaining compound (1b-2) by reacting compound (1b-1) and compound (1b-1-1). Compound (1b-2) can be obtained by reacting compound (1b-1) and compound (1b-1-1) in a solvent such as tetrahydrofuran, toluene or the like and in the presence of a catalyst such as copper (I) chloride, copper (I) iodide or the like and a base such as potassium carbonate, cesium carbonate, potassium phosphate, pyridine, 1,8-diazabicyclo[5.4.0]undec-7-ene or the like. 1 to 3 equivalents of compound (1b-1-1) are used with respect to compound (1b-1). 0.5 to 3 equivalents of catalyst are used with respect to compound (1b-1). 2 to 10 equivalents of base are used with respect to compound (1b-1). The reaction temperature is from 50° C. to the reflux temperature and the reaction time is from 1 to 48 hours.

[Production Process 1-2-2] Alternative Production Method of Compound (1b)

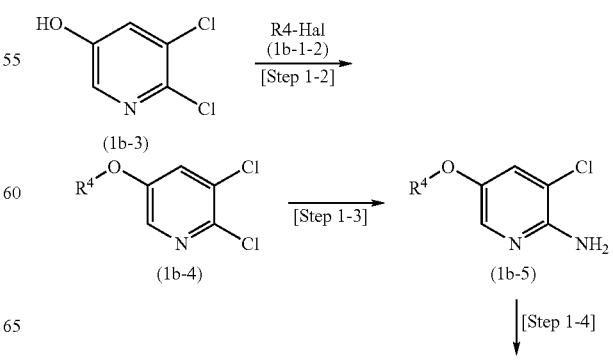

-continued

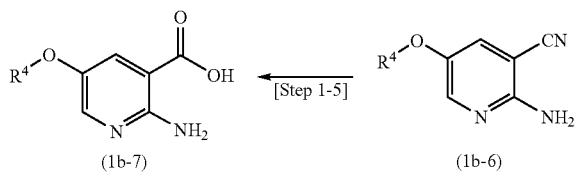

[wherein Hal and $R^4$ are the same as previously defined.]

Commercially available products can be used as is for each of the compounds in the flow chart above, and each of the compounds can be produced from commercially available products by the known method. In addition, each of the compounds can also be produced using the methods described in the examples.

[Step 1-2]

This step is a step for obtaining compound (1b-4) by reacting compound (1b-3) and compound (1b-1-2). Compound (1b-4) can be obtained by reacting compound (1b-3) and compound (1b-1-2) in a solvent such as N-N-dimethylformamide, N-methylpyrrolidinone or the like and in the presence of a base such as potassium carbonate, tert-butoxy potassium or the like. 1 equivalent to an excess of base are used with respect to compound (1b-3). The reaction temperature is from room temperature to 130° C. and the reaction time is from 10 minutes to 24 hours.

[Step 1-3]

This step is a step for obtaining compound (1b-5) by aminating compound (1b-4). Compound (1b-5) can be obtained by reacting compound (1b-4) in a sealed tube in the presence of a base such as concentrated aqueous ammonia or the like. 1.5 equivalents to an excess of base are used with respect to compound (1b-4). The reaction temperature is from 130 to 190° C. and the reaction time is from 1 to 48 hours.

[Step 1-4]

This step is a step for obtaining compound (1b-6) by cyanating compound (1b-5). Compound (1b-6) can be obtained by reacting compound (1b-5) and zinc cyanide in a nitrogen atmosphere in a solvent such as N,N-dimethylformamide, N-methylpyrrolidinone or the like and in the presence of a catalyst. Examples of catalysts that can be used include tetrakis(triphenylphosphine)palladium (0) or the like. 1 to 2 equivalents of zinc cyanide are used with respect to compound (1b-5). 0.01 to 0.1 equivalents of catalyst are used with respect to compound (1b-5). The reaction temperature is from 50° C. to the reflux temperature and the reaction time is from 5 minutes to 24 hours.

Alternative Method: Compound (1b-6) can be obtained by reacting compound (1b-5) and copper cyanide under nitrogen atmosphere in a solvent such as N,N-dimethylformamide, N-methylpyrrolidinone or the like. 1 equivalent to an excess of copper cyanide are used with respect to compound (1b-5). The reaction temperature is from 50° C. to the reflux temperature and the reaction time is from 10 minutes to 72 hours.

[Step 1-5]

This step is a step for obtaining compound (1b-7) by hydrolyzing compound (1b-6). Compound (1b-7) can be obtained by hydrolyzing compound (1b-6) in an aqueous solution of an acid such as hydrochloric acid, sulfuric acid or the like, or in an aqueous solution of a base such as sodium hydroxide, potassium hydroxide or the like. The reaction temperature is from room temperature to the reflux temperature and the reaction time is from 10 minutes to 10 hours.

[Production Process 1-2-3] Production Process of Compound (1b)

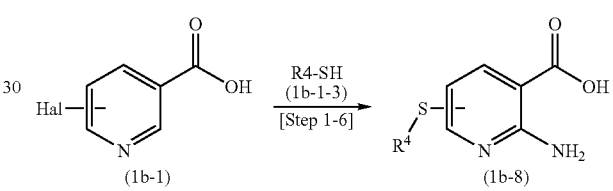

[wherein Hal and $R^4$ are the same as previously defined.]

Commercially available products can be used as is for each of the compounds in the flow chart above, and each of the compounds can be produced from commercially available products by a known method. In addition, each of the compounds can also be produced using the methods described in the examples.

[Step 1-6]

This step is a step for obtaining compound (1b-8) by reacting compound (1b-1) and compound (1b-1-3). Compound (1b-8) can be produced using the same method as that in Step 1-1.

[Production Process 1-3-1] Production Process of Compound (1c)

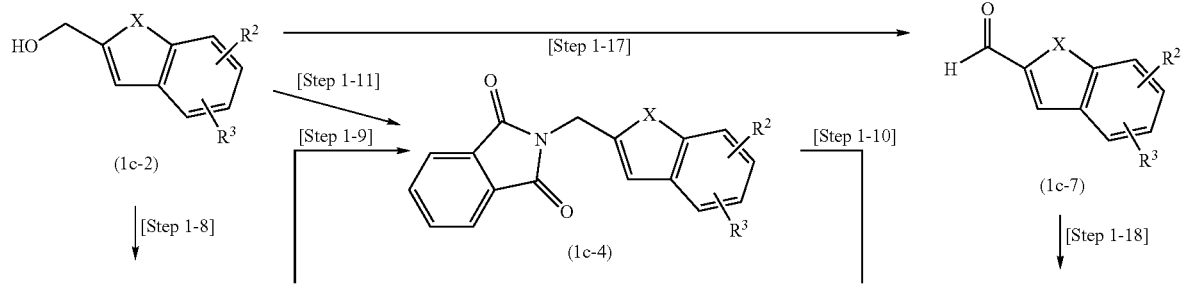

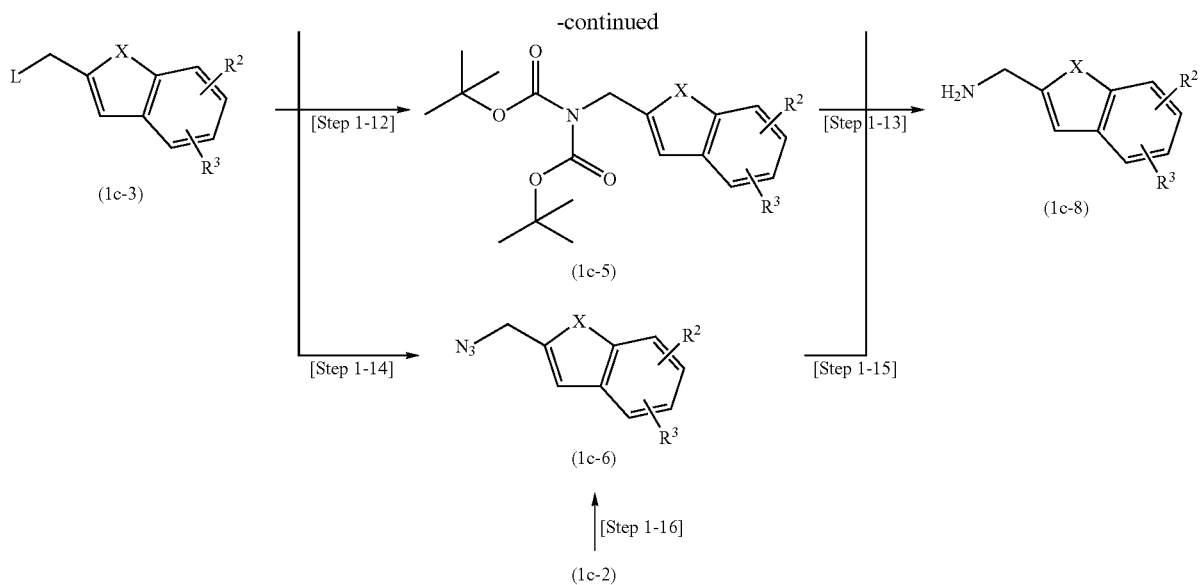

[wherein $R^2$, $R^3$ and X are the same as previously defined, $R^{41}$ represents a $C_{1-6}$ alkyl group, and L represents a halogen atom or a leaving group such as a methanesulfonyloxy group, p-toluenesulfonyloxy group or the like.]

A commercially available product can be used as is for each of the compounds in the above flow chart and each of the compounds can be produced from commercially available products by the known method. In addition, each of the compounds can also be produced using the method described in the production examples of the examples or [Production Process 1-3-2] to [Production Process 1-3-5]. Moreover, each of the compounds in the above flow chart can also be produced by converting substituents on the heterobicyclic ring using the method described in [Production Process 2-5] to [Production Process 2-7] or the like.

[Step 1-7]

This step is a step for obtaining compound (1c-2) by reducing compound (1c-1). Lithium aluminum hydride, for example, can be used for the reducing agent, and ether such as tetrahydrofuran, diethyl ether or the like can be used as solvent. 1 to 10 equivalents of reducing agent are used with respect to compound (1c-1). The reaction temperature is from 0° C. to the reflux temperature and the reaction time is from 5 minutes to 24 hours.

[Step 1-8]

This step is a step for obtaining compound (1c-3) by converting a hydroxyl group of compound (1c-2) to a leaving group.

In the case L is a methanesulfonyloxy group or p-toluenesulfonyloxy group, compound (1c-3) can be obtained by reacting compound (1c-2) with methanesulfonyl chloride or p-toluenesulfonyl chloride in a solvent such as dichloromethane and in the presence of an organic base such as triethylamine or the like. 1 equivalent to an excess of organic base is used with respect to compound (1c-2). 1 to 3 equivalents of methanesulfonyl chloride or p-toluenesulfonyl chloride are used with respect to compound (1c-2). The reaction temperature is from 0° C. to room temperature and the reaction time is from 10 minutes to 24 hours.

In the case L is a chlorine atom, compound (1c-3) can be obtained by allowing a chlorination reagent such as thionyl chloride, oxalyl chloride or the like to act on compound (1c-2). 1 equivalent to an excess of the chlorination reagent are used with respect to compound (1c-2). The reaction temperature is from 0° C. to room temperature and the reaction time is from 10 minutes to 24 hours.

[Step 1-9]

This step is a step for obtaining compound (1c-4) by reacting compound (1c-3) and potassium phthalimide. Compound (1c-4) can be obtained by reacting compound (1c-3) with potassium phthalimide in a solvent such as N,N-dimethylformamide or the like. 1 to 2 equivalents of potassium phthalimide are used with respect to compound (1c-3). The reaction temperature is from room temperature to 160° C. and the reaction time is from 10 minutes to 48 hours.

[Step 1-10]

This step is a step for obtaining compound (1c-8) from compound (1c-4). Compound (1c-8) can be obtained by adding 1 equivalent to an excess of hydrazine hydrate to compound (1c-4) in a solvent such as ethanol or the like. The reaction temperature is from 80° C. to the reflux temperature and the reaction time is from 10 minutes to 24 hours.

[Step 1-11]

This step is a step for obtaining compound (1c-4) by reacting compound (1c-2) with phthalimide. Compound (1c-4) can be obtained by reacting compound (1c-2) with phthalimide, triphenylphosphine and diethyl azodicarboxylate or diisopropyl azodicarboxylate in a solvent such as dichloromethane, tetrahydrofuran or the like. 1 to 2 equivalents of phthalimide, triphenylphosphine and diethyl azodicarboxylate or diisopropyl azodicarboxylate are used with respect to compound (1c-2). The reaction temperature is from −20 to 80° C. and the reaction time is from 5 minutes to 48 hours.

[Step 1-12]

This step is a step for obtaining compound (1c-5) by reacting compound (1c-3) with an amine protected with a tert-butoxycarbonyl group. Compound (1c-5) can be obtained by reacting compound (1c-3) with an amine protected with a tert-butoxycarbonyl group in a solvent such as N,N-dimethylformamide or the like and in the presence of a base such as sodium hydride or the like. 1 to 2 equivalents of base are used with respect to compound (1c-3). 1 to 2 equivalents of the amine protected with the tert-butoxycarbonyl group are used with respect to compound (1c-3). The reaction temperature is from room temperature to 80° C. and the reaction time is from 1 to 24 hours.

[Step 1-13]

This step is a step for obtaining compound (1c-8) by deprotecting the tert-butoxycarbonyl group of compound (1c-5). Compound (1c-8) can be obtained by deprotecting the tert-butoxycarbonyl group of compound (1c-5) in a solvent such as dichloromethane or the like and in the presence of 2 equivalents to an excess of acid such as trifluoroacetic acid or the like with respect to compound (1c-5). The reaction temperature is from 0 to 60° C. and the reaction time is from 10 minutes to 24 hours.

[Step 1-14]

This step is a step for obtaining compound (1c-6) by converting the leaving group of compound (1c-3) to an azide group. Compound (1c-6) can be obtained by reacting compound (1c-3) with an azidation reagent such as sodium azide, potassium azide or the like in a solvent such as N,N-dimethylformamide or the like. 1 to 5 equivalents of the azidation reagent are used with respect to compound (1c-3). The reaction temperature is from room temperature to 80° C. and the reaction time is from 10 minutes to 48 hours.

[Step 1-15]

This step is a step for obtaining compound (1c-8) by reducing the azide group of compound (1c-6). Compound (1c-8) can be obtained by carrying out catalytic hydrogenation using Lindlar's catalyst in a solvent such as ethanol or the like. A catalytic amount to an excess of Lindlar's catalyst is used with respect to compound (1c-6). The reaction temperature is from room temperature to 80° C., the reaction time is from 30 minutes to 36 hours, and the reaction pressure is from 1 to 4 atmospheres.

As an alternative method, compound (1c-8) can be obtained by allowing triphenylphosphine to act in a solvent such as dichloromethane, tetrahydrofuran or the like. 1.0 to 2.0 equivalents of triphenylphosphine are used with respect to compound (1c-6).

[Step 1-16]

This step is a step for obtaining compound (1c-6) by converting the hydroxyl group of compound (1c-2) to an azide group. Compound (1c-6) can be obtained by reacting compound (1c-2) with diphenylphosphorylazide in a solvent such as benzene, toluene or the like and in the presence of an organic base such as 1,8-diazabicyclo[5,4,0]undec-7-ene or the like. 1 to 1.5 equivalents of organic base are used with respect to compound (1c-2). 1 to 1.5 equivalents of diphenylphosphorylazide are used with respect to compound (1c-2). The reaction temperature is from room temperature to 80° C. and the reaction time is from 10 minutes to 48 hours.

[Step 1-17]

This step is a step for obtaining compound (1c-7) by oxidizing the hydroxymethyl group of compound (1c-2). Compound (1c-7) can be obtained by oxidizing compound (1c-2) using an oxidizing agent such as manganese dioxide or the like in a solvent such as chloroform, dichloromethane or the like. 1 equivalent to an excess of oxidizing agent are used with respect to compound (1c-2). The reaction temperature is from room temperature to the reflux temperature and the reaction time is from 30 minutes to 24 hours.

[Step 1-18]

This step is a step for obtaining compound (1c-8) by converting the formyl group of compound (1c-7) to an aminomethyl group. Compound (1c-8) can be obtained by carrying out catalytic hydrogenation using a Raney nickel catalyst in a solvent such as ammonia-containing methanol, ammonia-containing ethanol or the like. A catalytic amount to an excess of Raney nickel catalyst is used with respect to compound (1c-7). The reaction temperature is from 0° C. to room temperature, the reaction time is from 30 minutes to 36 hours and the reaction pressure is 1 to 4 atmospheres.

[Production Process 1-3-2] Production Process of Compound (1c-1) in the Form of Compound (1c-11)

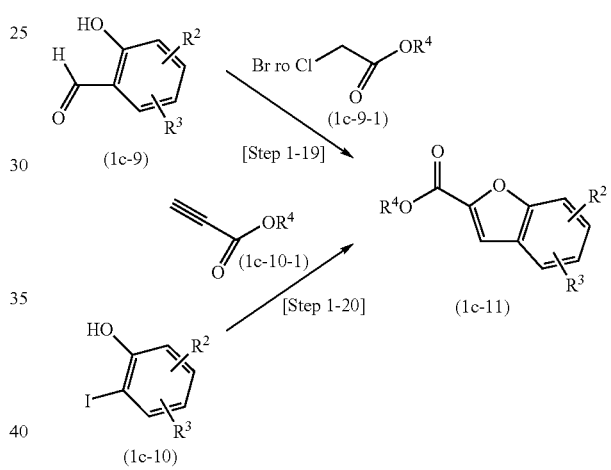

[wherein $R^2$, $R^3$ and $R^4$ are the same as previously defined.]

Commercially available products can be used as is for compound (1c-9) and compound (1c-10). Commercially available products can also be used as is for compound (1c-9-1) and compound (1c-10-1), or they can be produced from commercially available products using known methods.

[Step 1-19]

This step is a step for obtaining compound (1c-11) by reacting compound (1c-9) and compound (1c-9-1). Compound (1c-11) can be obtained by reacting compound (1c-9) and compound (1c-9-1) in a solvent such as N,N-dimethylformamide, dimethylsulfoxide or the like and in the presence of a base such as sodium hydroxide, potassium carbonate, cesium carbonate or the like. 1 to 2 equivalents of compound (1c-9-1) are used with respect to compound (1c-9). 2 equivalents to an excess of base are used with respect to compound (1c-9). The reaction temperature is from room temperature to the reflux temperature and the reaction time is from 5 minutes to 24 hours.

[Step 1-20]

This step is a step for obtaining compound (1c-11) by reacting compound (1c-10) and compound (1c-10-1). Compound (1c-11) can be obtained by reacting compound (1c-10) and compound (1c-10-1) in a solvent such as N,N-dimethylformamide, N-methylpyrrolidinone or the like and in the presence of a catalyst such as diacetobis(triphenylphosphine) palladium (II)/copper iodide or the like and a base such as sodium acetate or the like. 1 to 1.5 equivalents of compound (1c-10-1) are used with respect to compound (1c-10). 0.05 to 0.5 equivalents of catalyst are used with respect to compound (1c-10). 2 equivalents to an excess of base are used with respect to compound (1c-10). The reaction temperature is from room temperature to 80° C. and the reaction time is from 30 minutes to 24 hours.

[Production Process 1-3-3] Production Process of Compound (1c-1) in the Form of Compound (1c-13)

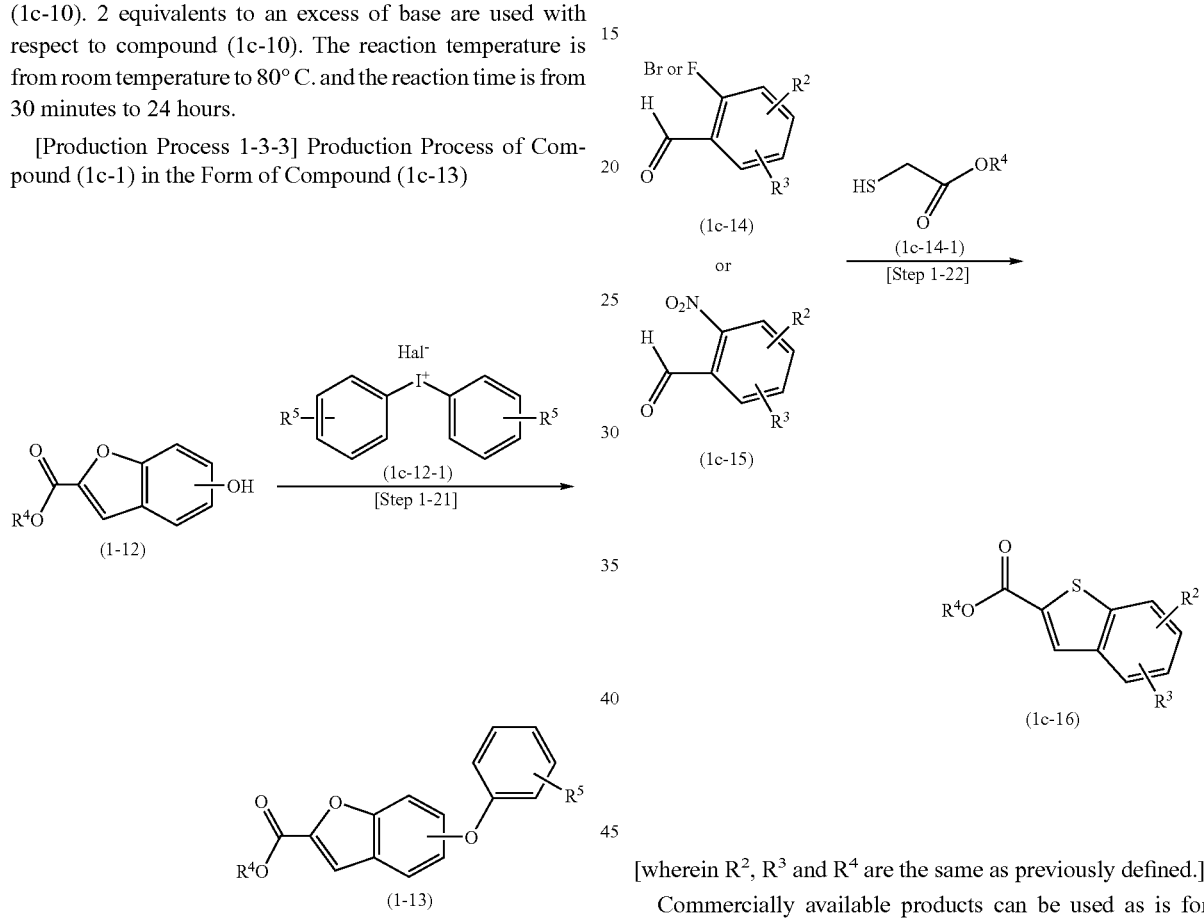

[wherein Hal and $R^4$ are the same as previously defined, and $R^5$ represents a hydrogen atom, halogen, a $C_{1-6}$ alkyl group or a $C_{1-6}$ alkoxy group.]

Commercially available products can be used as is for compound (1-12) and compound (1c-12-1), or they can be produced from commercially available products using the known methods.

[Step 1-21]

This step is a step for obtaining compound (1-13) by reacting compound (1-12) and compound (1c-12-1). Compound (1-13) can be obtained by reacting compound (1-12) and compound (1c-12-1) in a solvent such as tetrahydrofuran, N,N-dimethylformamide, dimethylsulfoxide or the like and in the presence of a base such as potassium tert-butoxide or the like. 1 to 1.5 equivalents of compound (1c-12-1) are used with respect to compound (1-12). 1 to 1.5 equivalents of base are used with respect to compound (1-12). The reaction temperature is from room temperature to the reflux temperature and the reaction time is from 30 minutes to 24 hours.

[Production Process 1-3-4] Production Process of Compound (1c-1) in the Form of Compound (1c-16)

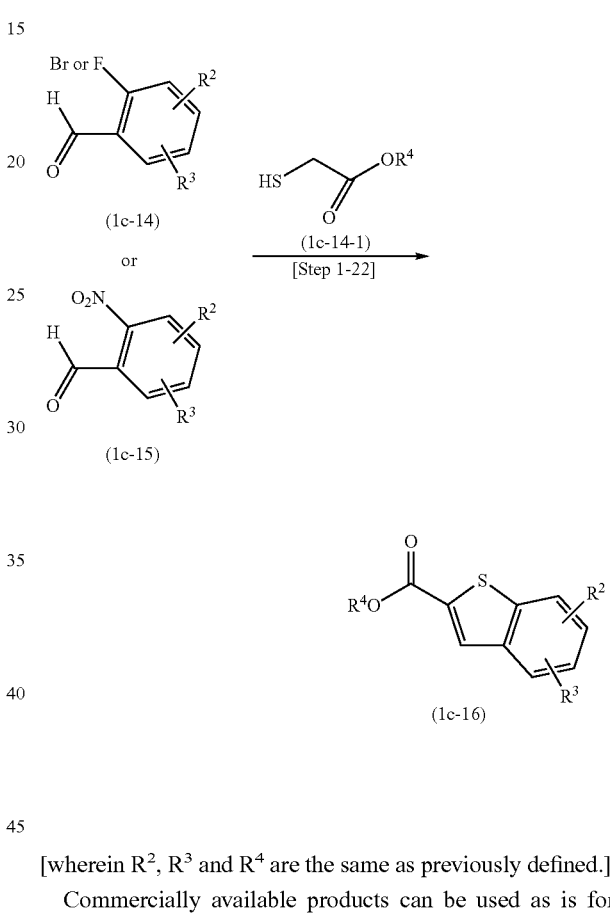

[wherein $R^2$, $R^3$ and $R^4$ are the same as previously defined.]

Commercially available products can be used as is for compound (1c-14), compound (1c-15) and compound (1c-14-1), or they can be produced from commercially available products using the known methods.

[Step 1-22]

This step is a step for obtaining compound (1c-16) by reacting compound (1c-14) or compound (1c-15) and compound (1c-14-1). Compound (1c-16) can be obtained by reacting compound (1c-14) or compound (1c-15) with compound (1c-14-1) in a solvent such as N,N-dimethylformamide, dimethylsulfoxide or the like and in the presence of a base such as potassium carbonate, sodium hydroxide or the like. 1 to 1.5 equivalents of compound (1c-14-1) are used with respect to compound (1c-14) or compound (1c-15). 2 to 5 equivalents of base are used with respect to compound (1c-14) or compound (1c-15). The reaction temperature is from room temperature to the reflux temperature and the reaction time is from 5 minutes to 24 hours.

[Production Process 1-3-5] Production Process of Compound (1c-1) in the Form of Compound (1c-19)

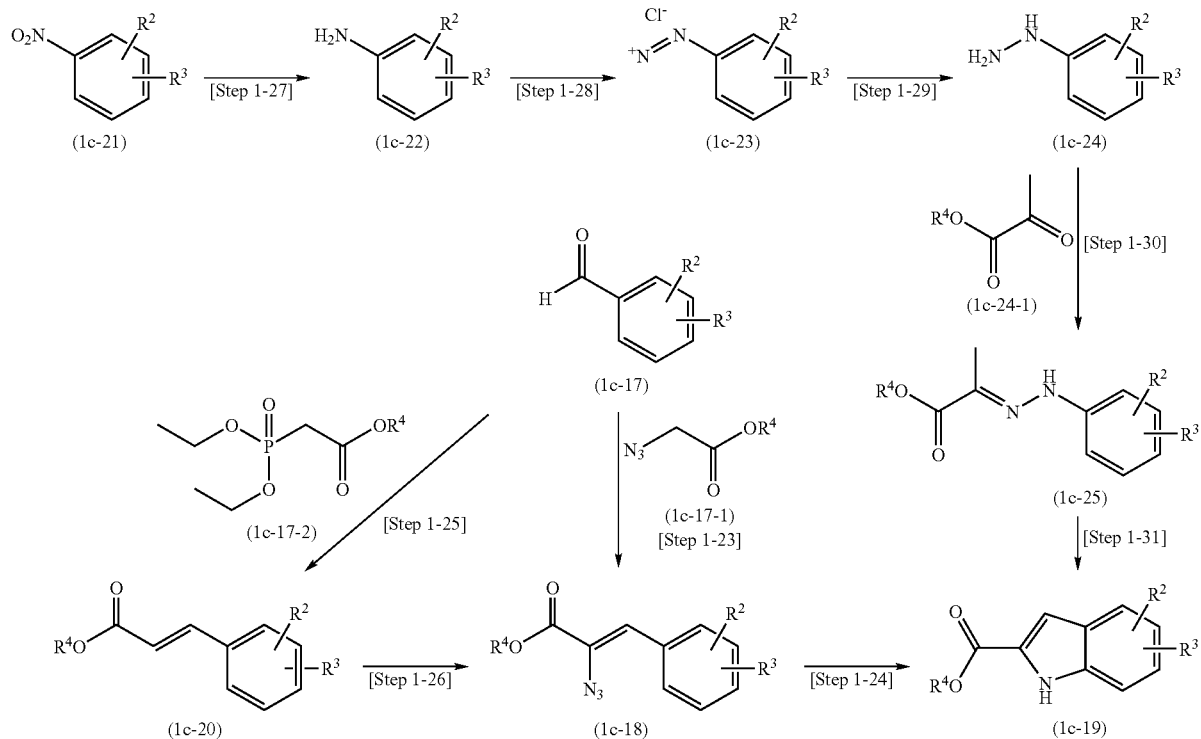

[wherein R², R³ and R⁴ are the same as previously defined.]

Commercially available products can be used as is for compound (1c-17), compound (1c-21), compound (1c-17-1), compound (1c-17-2) and compound (1c-24-1), or they can be produced from commercially available products using the known methods.

[Step 1-23]

This step is a step for obtaining compound (1c-18) by reacting compound (1c-17) and compound (1c-17-1). Compound (1c-18) can be obtained by reacting compound (1c-17) and compound (1c-17-1) in a solvent such as methanol, ethanol or the like and in the presence of a base such as sodium methoxide, sodium ethoxide or the like. 1 to 2 equivalents of compound (1c-17-1) are used with respect to compound (1c-17). 1 to 3 equivalents of base are used with respect to compound (1c-17). The reaction temperature is from room temperature to the reflux temperature and the reaction time is from 30 minutes to 48 hours.

[Step 1-24]

This step is a step for obtaining compound (1c-19) by ring closure of compound (1c-18). Compound (1c-19) can be obtained by heating compound (1c-18) in the presence of a solvent such as toluene, xylene, mesitylene or the like. The reaction temperature is the reflux temperature and the reaction time is from 30 minutes to 48 hours.

[Step 1-25]

This step is a step for obtaining compound (1c-20) by reacting compound (1c-17) and compound (1c-17-2). Compound (1c-20) can be obtained by reacting compound (1c-17) and compound (1c-17-2) in a solvent such as N,N-dimethylformamide, tetrahydrofuran or the like and in the presence of a base such as sodium hydride, cesium carbonate, barium hydroxide or the like. 1 to 2 equivalents of compound (1c-17-2) are used with respect to compound (1c-17). 1 to 2 equivalents of base are used with respect to compound (1c-17). The reaction temperature is from room temperature to the reflux temperature and the reaction time is from 30 minutes to 24 hours.

Alternative Method-1 for [Step 1-25]

This step is a step for obtaining compound (1c-20) by reacting compound (1c-17) using (carbetoxymethylene)triphenylphosphorane instead of compound (1c-17-2). Compound (1c-20) can be obtained by reacting compound (1c-17) with (carbetoxymethylene)triphenylphosphorane in a solvent such as benzene, toluene or the like. 1 to 1.5 equivalents of (carbetoxymethylene)triphenylphosphorane are used with respect to compound (1c-17). The reaction temperature is the reflux temperature and the reaction time is from 30 minutes to 24 hours.

[Step 1-26]

This step is a step for obtaining compound (1c-18) by azidating the olefin site of an unsaturated carboxylic acid ester of compound (1c-20). Compound (1c-18) can be obtained by reacting an azidation agent such as sodium azide, potassium azide or the like in a solvent such as acetonitrile, acetone or the like and in the presence of a ammonium cerium (IV) nitrate followed by further treating with a base such as sodium acetate or the like in a solvent such as acetonitrile, acetone or the like. 1 to 2 equivalents of the azidation agent are used with respect to compound (1c-20). 1.5 to 2 equivalents of ammonium cerium (IV) nitrate are used with respect to the azidation agent. The temperature of the reaction with the azidation agent is from 0° C. to room temperature and the temperature during treatment with a base such as sodium acetate or the like is from room temperature to the reflux temperature. The reaction time is from 1 to 24 hours.

[Step 1-27]

This step is a step for obtaining compound (1c-22) by reducing the nitro group of compound (1c-21). Compound (1c-22) can be obtained by carrying out catalytic hydrogenation using a catalyst such as platinum dioxide or the like in a solvent such as methanol, ethanol or the like. A catalytic amount to an excess of catalyst is used with respect to compound (1c-21). The reaction temperature is from room temperature to 80° C. and the reaction time is from 30 minutes to 24 hours.

Alternative Method for [Step 1-27]

This step is a step for obtaining compound (1c-22) by reducing the nitro group of compound (1c-21). Compound (1c-22) can be obtained by reacting compound (1c-21) with a reducing agent such as iron (powder) in a solvent such as ethanol or the like and in the presence of an excess amount of acetic acid. 2 to 5 equivalents of the reducing agent are used with respect to compound (1c-21). The reaction temperature is the reflux temperature and the reaction time is from 30 minutes to 24 hours.

[Step 1-28]

This step is a step for obtaining compound (1c-23) by diazotizing the amino group of compound (1c-22). Compound (1c-23) can be obtained by diazidating compound (1c-22) in a solvent such as hydrochloric acid or the like and in the presence of a diazotization agent such as sodium nitrite or the like. 1 to 1.5 equivalents of the diazotization agent are used with respect to compound (1c-22). The reaction temperature is from 0 to 5° C. and the reaction time is from 5 minutes to 12 hours.

[Step 1-29]

This step is a step for obtaining compound (1c-24) by reducing the diazo group of compound (1c-23). Compound (1c-24) can be obtained by reacting compound (1c-23) in a solvent such as hydrochloric acid or the like in the presence of a reducing agent such as tin (II) chloride or the like. 1 to 3 equivalents of the reducing agent are used with respect to compound (1c-23). The reaction temperature is from 0 to 5° C. and the reaction time is from 30 minutes to 24 hours.

[Step 1-30]

This step is a step for obtaining compound (1c-25) by reacting compound (1c-24) and compound (1c-24-1). Compound (1c-25) can be obtained by reacting compound (1c-24) and compound (1c-24-1) in a solvent such as water-containing ethanol or the like and in the presence of a base such as potassium hydroxide, sodium acetate or the like. 1 equivalent to an excess of base are used with respect to compound (1c-24). The reaction temperature is from room temperature to the reflux temperature and the reaction time is from 30 minutes to 24 hours.

[Step 1-31]

This step is a step for obtaining compound (1c-19) by ring closure of compound (1c-25). Compound (1c-19) can be obtained by reacting compound (1c-25) in a solvent such as toluene, benzene or the like, for example, in the presence of an acid such as polyphosphoric acid, hydrochloric acid, sulfuric acid, para-toluenesulfonic acid or the like. 1 equivalent to an excess of acid are used with respect to compound (1c-25). The reaction temperature is from 80 to 200° C. and the reaction time is from 30 minutes to 24 hours.

[Production Process 2-1] Conversion of Substituent on Pyridine Ring in Compound (1a)-1

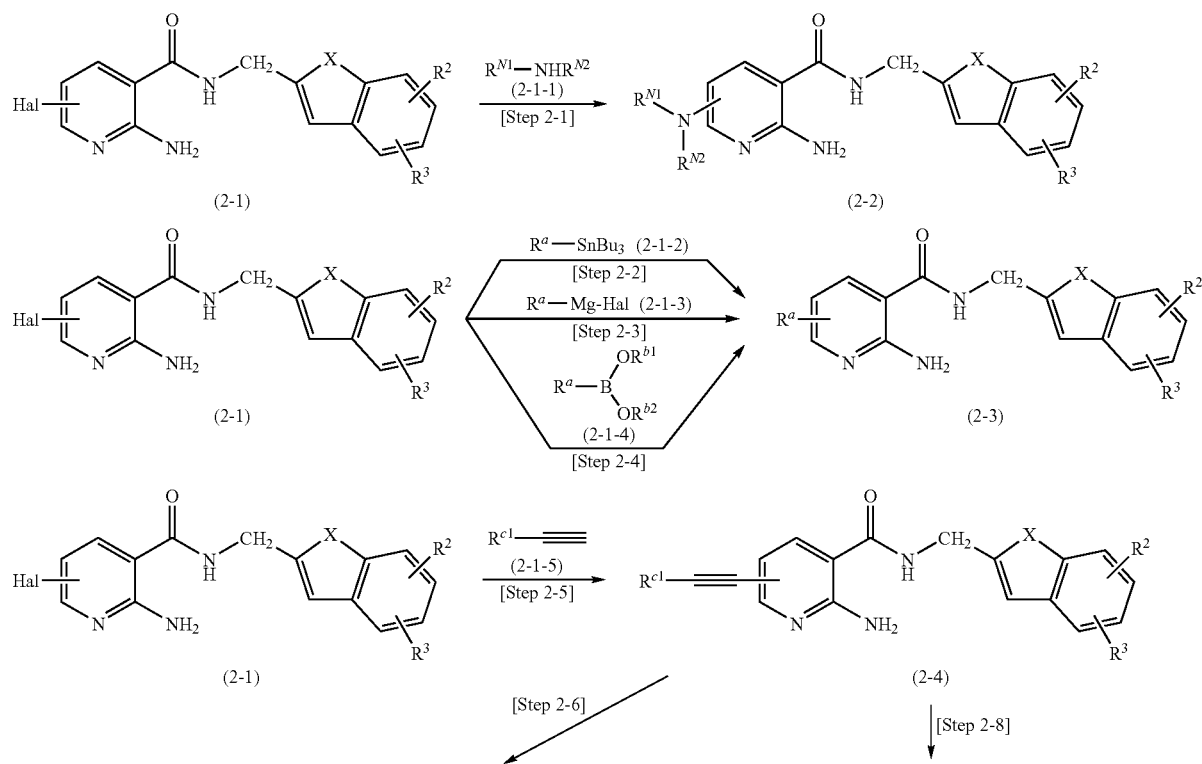

-continued

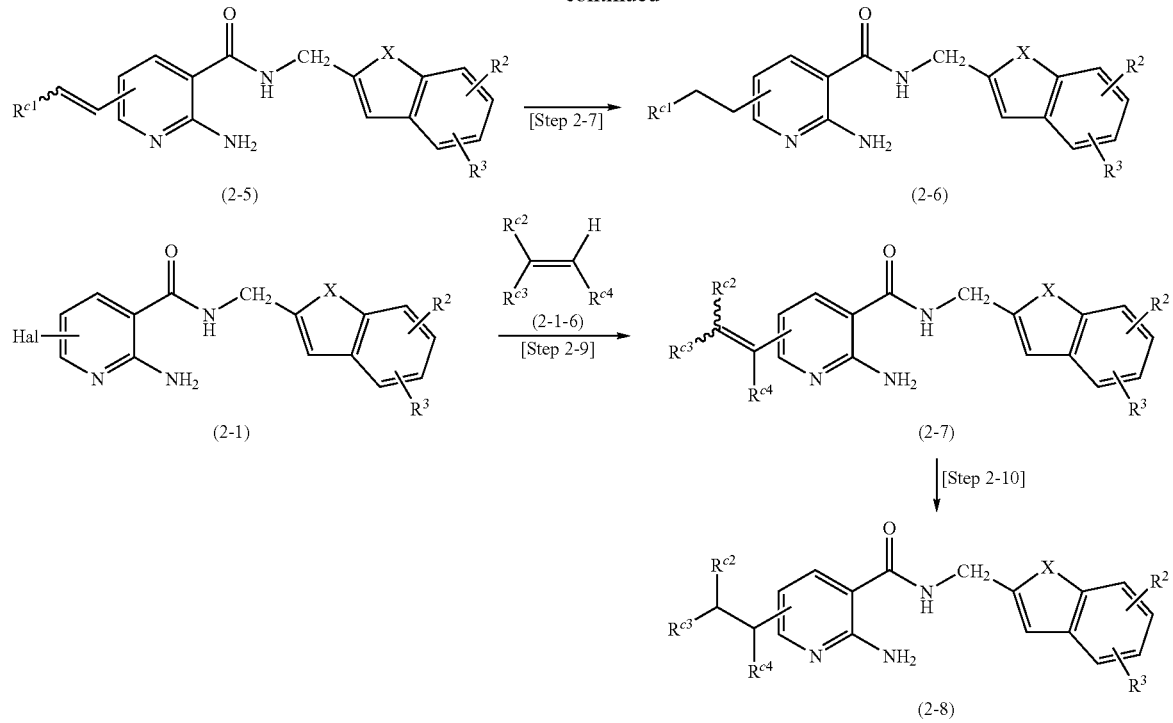

[wherein Hal, $R^2$, $R^3$ and X are the same as previously defined, $R^{N1}$ represents a $C_{1-6}$ alkyl group, a $C_{2-6}$ alkenyl group, a $C_{2-6}$ alkynyl group, a $C_{3-8}$ cycloalkyl group or a $C_{3-8}$ cycloalkyl $C_{1-6}$-alkyl group, $R^{N2}$ represents a hydrogen atom or a $C_{1-6}$ alkyl group, $R^a$ represents a $C_{2-6}$ alkenyl group, $R^{b1}$ and $R^{b2}$ are the same as or different from each other and represent a hydrogen atom or a $C_{1-6}$ alkyl group or together form a cyclic boric acid ester, $R^{c1}$, $R^{c2}$, $R^{c3}$ and $R^{c4}$ are the same as or different from each other and represent a hydrogen atom, a $C_{1-6}$ alkyl group, a $C_{2-6}$ alkenyl group, a $C_{2-6}$ alkynyl group, a $C_{3-8}$ cycloalkyl group, a $C_{6-10}$ aryl group or 5- to 10-membered heterocyclic group.]

Commercially available products can be used as is for compound (2-1-1), compound (2-1-2), compound (2-1-3), compound (2-1-4), compound (2-1-5) and compound (2-1-6), or they can be produced from commercially available products using the known methods.

[Step 2-1]

This step is a step for obtaining compound (2-2) by reacting compound (2-1) and compound (2-1-1). A solvent such as dimethylsulfoxide, tetrahydrofuran, toluene, acetonitrile, N,N-dimethylformamide or the like can be used for the solvent. In addition, the reaction can also be carried out in the absence of a solvent. The reaction is preferably carried out in a sealed tube, the reaction time is from 1 to 60 hours, and the reaction temperature is from 50 to 200° C. Furthermore, 2 equivalents to an excess of an organic base such as N,N'-diisopropyl ethylamine, triethylamine, pyridine, 1,8-diazabicyclo[5,4,0]undec-7-ene or the like, or an inorganic base such as potassium carbonate, sodium carbonate or the like may be added with respect to compound (2-1).

[Step 2-2]

This step is a step for obtaining compound (2-3) by reacting compound (2-1) and compound (2-1-2). Compound (2-3) can be obtained by reacting compound (2-1) and compound (2-1-2) in the presence of a catalyst. A catalyst such as tetrakis (triphenylphosphine)palladium (0), dichlorobis(triphenylphosphine) palladium (II) or the like can be used for the catalyst. A solvent such as toluene, 1,4-dioxane, xylene or the like can be used for the solvent. 2 to 3 equivalents of compound (2-1-2) are used with respect to compound (2-1). 0.05 to 0.3 equivalents of the catalyst are used with respect to compound (2-1). The reaction temperature is from 100 to 140° C. and the reaction time is from 1 to 24 hours.

[Step 2-3]

This step is a step for obtaining compound (2-3) by reacting compound (2-1) and compound (2-1-3). Compound (2-3) can be obtained by reacting compound (2-1) and compound (2-1-3) in the presence of a catalyst. A catalyst such as dichloro(1,1'-bis(diphenylphosphino)propane)nickel (II), dichloro(1,1'-bis(diphenylphosphino)ferrocene)nickel (II), tetrakis (triphenylphosphine)palladium (0) or the like can be used for the catalyst. A solvent such as tetrahydrofuran, 1,4-dioxane or the like can be used for the solvent. 3 equivalents to an excess of compound (2-1-3) can be used with respect to compound (2-1). 0.05 to 0.3 equivalents of the catalyst can be used with respect to compound (2-1). The reaction temperature is from 0° C. to the reflux temperature and the reaction time is from 5 minutes to 24 hours.

[Step 2-4]

This step is a step for obtaining compound (2-3) by reacting compound (2-1) and compound (2-1-4). Compound (2-3) can be obtained by reacting compound (2-1) and compound (2-1-4) in the presence of a catalyst and base. A catalyst such as palladium (II) acetate, tetrakis(triphenylphosphine)palladium (0), dichlorobis(triphenylphosphine)palladium (II), tris (dibenzylideneacetone)dipalladium (0) or the like can be used for the catalyst. In order to obtain a favorable result, 0.25 to 1.5 equivalents of a phosphate ligand (such as triphenylphosphine, tri-tert-butylphosphine or the like) may be added with respect to compound (2-1). A base such as potassium carbonate, sodium carbonate, cesium carbonate, potassium fluoride, cesium fluoride, potassium phosphate, sodium hydroxide, barium hydroxide, potassium hydroxide or the like can be used for the base. This reaction is preferably carried out under an inert gas atmosphere such as nitrogen gas, argon gas or the like, and a solvent such as tetrahydrofuran, 1,4-dioxane, methanol, ethanol, toluene, water or the like can be used for the solvent. A quaternary ammonium salt such as tetrabutyl ammonium bromide or the like can also be added depending on the reagents used. 0.05 to 0.3 equivalents of catalyst are used with respect to compound (2-1). 2 equivalents to an excess of base are used with respect to compound (2-1). The reaction temperature is from room temperature to the reflux temperature and the reaction time is from 30 minutes to 24 hours.

[Step 2-5]

This step is a step for obtaining compound (2-4) by reacting compound (2-1) and compound (2-1-5). Compound (2-4) can be obtained by reacting compound (2-1) and compound (2-1-5) in the presence of a catalyst and base. A catalyst such as palladium (II) acetate, tetrakis(triphenylphosphine)palladium (0), dichlorobis(triphenylphosphine)palladium (II), tris(dibenzylideneacetone)dipalladium (0) or the like can be used for the catalyst. A base such as triethylamine, N,N'-diisopropylethylamine, pyridine or the like can be used for the base. A solvent such as tetrahydrofuran, acetonitrile, 1,4-dioxane, N,N-dimethylformamide, N-methylpyrrolidinone, dimethylsulfoxide, toluene or the like can be used for the solvent. In addition, in order to obtain a favorable result, 0.1 to 0.3 equivalents of copper (I) iodide or tetrabutyl ammonium fluoride may be added with respect to compound (2-1). 1 to 5 equivalents of compound (2-1-5) are used with respect to compound (2-1). 0.05 to 0.3 equivalents of catalyst are used with respect to compound (2-1). 2 to 5 equivalents of base are used with respect to compound (2-1). The reaction temperature is from room temperature to 150° C. and the reaction time is from 30 minutes to 24 hours.

[Step 2-6]

This step is a step for obtaining compound (2-5) by reducing the triple bond of compound (2-4) to a double bond. Compound (2-5) can be obtained by using a catalyst such as Lindlar's catalyst, palladium-barium sulfate or the like in a solvent such as tetrahydrofuran, ethyl acetate, acetonitrile, methanol, ethanol or the like and under a hydrogen atmosphere. A preferable solvent is ethyl acetate. In order to obtain a favorable result, 0.1 to 1 equivalent of quinoline may be added with respect to compound (2-4). A catalytic amount to an excess of catalyst is used with respect to compound (2-4). The reaction temperature is room temperature, the reaction time is from 15 minutes to 24 hours, and the reaction pressure is from 1 to 4 atmospheres.

[Step 2-7]

This step is a step for obtaining compound (2-6) by reducing compound (2-5). Compound (2-6) can be obtained by using a catalyst such as palladium-carbon, Raney nickel, platinum dioxide or the like in a solvent such as tetrahydrofuran, ethyl acetate, acetonitrile, methanol, ethanol or the like and under a hydrogen atmosphere. A catalytic amount to an excess of catalyst are used with respect to compound (2-5). The reaction temperature is room temperature, the reaction time is from 5 minutes to 24 hours, and the reaction pressure is from 1 to 4 atmospheres.

[Step 2-8]

This step is a step for obtaining compound (2-6) by reducing compound (2-4). Compound (2-6) can be produced using the same method as in [Step 2-7].

[Step 2-9]

This step is a step for obtaining compound (2-7) by reacting compound (2-1) and compound (2-1-6). Compound (2-7) can be obtained by reacting compound (2-1) and compound (2-1-6) in the presence of a catalyst and base. A catalyst such as palladium (II) acetate, tetrakis(triphenylphosphine)palladium (0), dichlorobis(triphenylphosphine)palladium (II), tris(dibenzylideneacetone)dipalladium (0) or the like can be used for the catalyst. A base such as triethylamine, N,N'-diisopropylethylamine, N,N'-dicyclohexylmethylamine or the like can be used for the base. A solvent such as acetonitrile, tetrahydrofuran, 1,4-dioxane, benzene, toluene, xylene, N,N-dimethylformamide, N-methylpyrrolidinone or the like can be used for the solvent. In addition, in order to obtain a favorable result, 0.25 to 1.5 equivalents of a phosphine ligand (such as triphenylphosphine, tri-tert-butylphosphine, 2-(di-tert-butylphosphino)biphenyl) or the like may be added with respect to compound (2-1). 1 to 4 equivalents of compound (2-1-6) are used with respect to compound (2-1). 0.05 to 0.3 equivalents of catalyst are used with respect to compound (2-1). 2 to 5 equivalents of base are used with respect to compound (2-1). The reaction temperature is from room temperature to 150° C. and the reaction time is from 5 minutes to 24 hours.

[Step 2-10]

This step is a step for obtaining compound (2-8) by reducing compound (2-7). Compound (2-8) can be produced using the same method as in [Step 2-7].

[Production Process 2-2] Conversion of Substituent on Pyridine Ring in Compound (1a)-2

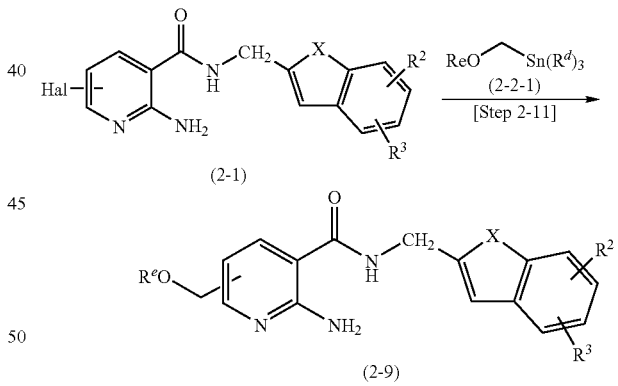

[wherein Hal, $R^2$, $R^3$ and X are the same as previously defined, and $R^d$ and $R^e$ are the same as or different from each other and represent a $C_{1-6}$ alkyl group.]

[Step 2-11]

This step is a step for obtaining compound (2-9) by reacting compound (2-1) and compound (2-2-1). This reaction is preferably carried out under an inert gas atmosphere, and although varying according to the starting materials and reagents used, a solvent such as N-methylpyrrolidinone, 1,4-dioxane or the like can be used for the solvent. A catalyst such as palladium (II) acetate, tetrakis(triphenylphosphine)palladium (0), dichlorobis(triphenylphosphine)palladium (II), tris(dibenzylideneacetone)dipalladium (0) or the like can be used for the catalyst. In order to obtain a favorable result, a phosphine ligand, and preferably a phosphine ligand such as triphenylphosphine, tri-tert-butylphosphine, diphenylphosphinoferrocene or the like may be added. 1 to 10 equivalents of compound (2-2-1) are used with respect to compound (2-1). 0.001 to 0.2 equivalents of catalyst are used with respect to compound (2-1). 0.001 to 0.4 equivalents of phosphine ligand are used with respect to compound (2-1). The reaction temperature is from room temperature to the reflux temperature and the reaction time is from 10 minutes to 24 hours.

[Production Process 2-3] Conversion of a Substituent on Pyridine Ring in Compound (1a)-3

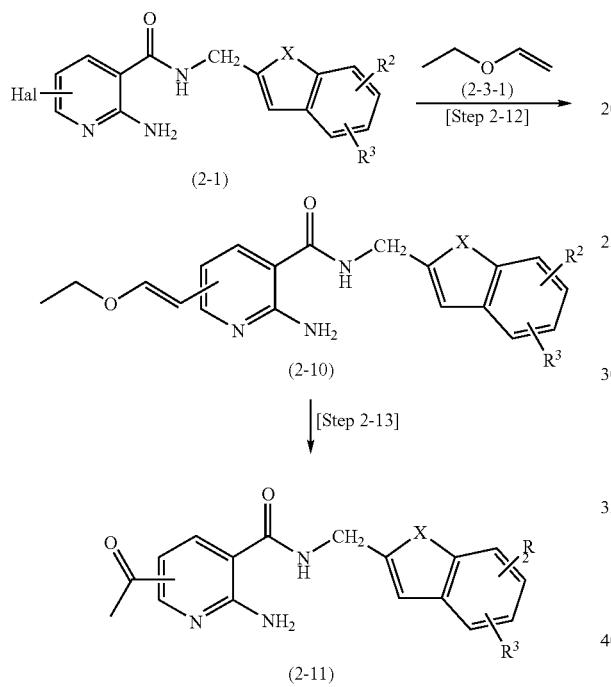

[wherein Hal, $R^2$, $R^3$ and X are the same as previously defined.]

[Step 2-12]

This step is a step for obtaining compound (2-10) by reacting compound (2-1) and compound (2-3-1). Compound (2-10) can be obtained by reacting compound (2-1) with catechol borane in a solvent such as tetrahydrofuran, 1,4-dioxane or the like and then reacting with compound (2-3-1) in the presence of a base and catalyst. A base such as sodium hydroxide, potassium hydroxide, potassium carbonate, cesium carbonate or the like can be used for the base. A catalyst such as palladium (II) acetate, tetrakis(triphenylphosphine)palladium (0), dichlorobis(triphenylphosphine)palladium (II), tris(dibenzylideneacetone)dipalladium (0) or the like can be used for the catalyst. 1 equivalent to an excess of compound (2-3-1) can be used with respect to compound (2-1). 1 equivalent of catechol borane can be used with respect to compound (2-3-1). 2 equivalents to an excess of base can be used with respect to compound (2-1). 0.05 to 1 equivalent of catalyst can be used with respect to compound (2-1). The reaction temperature is from 0° C. to the reflux temperature and the reaction time is from 1 to 24 hours.

[Step 2-13]

This step is a step for obtaining compound (2-11) from compound (2-10). Compound (2-11) can be obtained by reacting compound (2-10) in a solvent such as acetone, methanol, tetrahydrofuran, water or the like and under acidic conditions with an acid such as sulfuric acid, hydrochloric acid, para-toluenesulfonic acid or the like. A catalytic amount to an excess of acid can be used with respect to compound (2-10). The reaction temperature is from 0° C. to the reflux temperature and the reaction time is from 5 minutes to 24 hours.

[Production Process 2-4] Conversion of a Substituent on Pyridine Ring in Compound (1a)-4

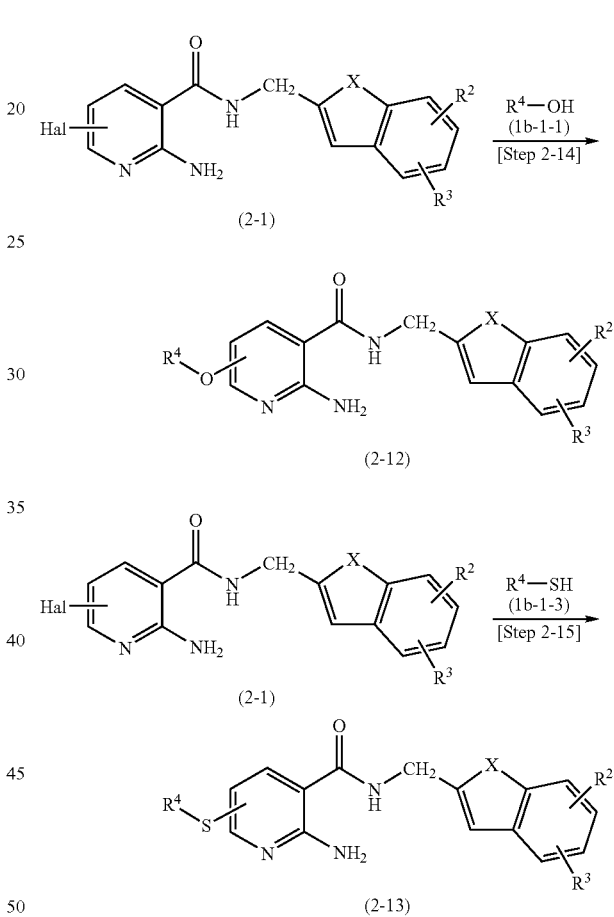

[wherein Hal, $R^2$, $R^3$, $R^4$ and X are the same as previously defined.]

[Step 2-14]

This step is a step for obtaining compound (2-12) by reacting compound (2-1) and compound (1b-1-1). Compound (2-12) can be produced using the same method as in [Production Process 1-2-1].

[Step 2-15]

This step is a step for obtaining compound (2-13) by reacting compound (2-1) and compound (1b-1-3). Compound (2-13) can be produced using the same method as in [Production Process 1-2-3].

[Production Process 2-5] Conversion of a Substituent on Heterobicyclic Ring in Compound (1a)-1
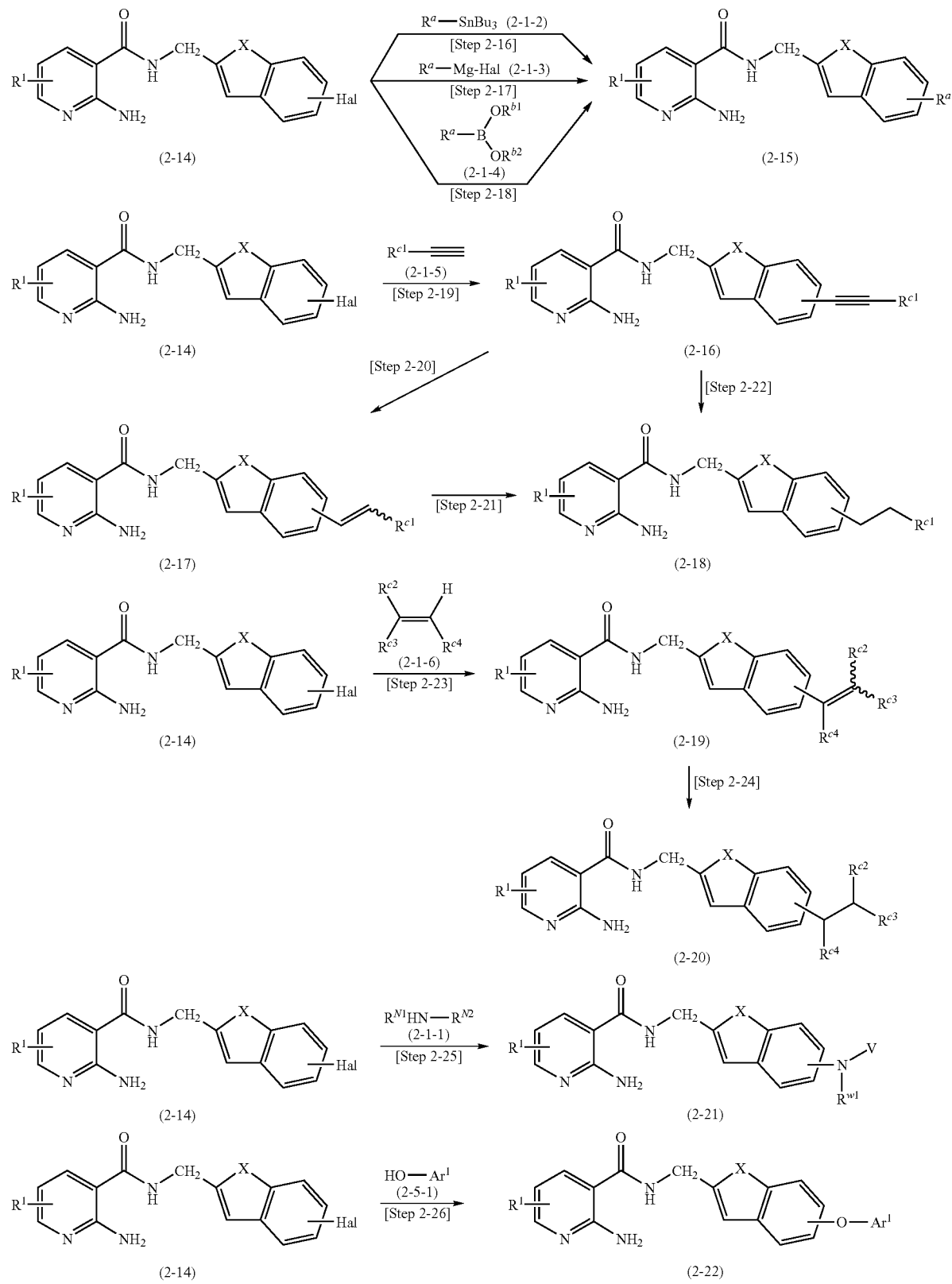

[wherein Hal, $R^1$, $R^a$, $R^{b1}$, $R^{b2}$, $R^{c1}$, $R^{c2}$, $R^{c3}$, $R^{c4}$, $R^{N1}$, $R^{N2}$ and X are the same as previously defined, and $Ar^1$ represents a $C_{6-10}$ aryl group optionally having 1 to 3 groups selected from the group consisting of a halogen atom, a $C_{1-6}$ alkyl group and a $C_{1-6}$ alkoxy group.]

Commercially available products can be used as is for compound (2-1-2), compound (2-1-3), compound (2-1-4), compound (2-1-5), compound (2-1-6), compound (2-1-1) and compound (2-5-1), or they can be produced from commercially available products using the known methods.

[Step 2-16]

This step is a step for obtaining compound (2-15) by reacting compound (2-14) and compound (2-1-2). Compound (2-15) can be produced using the same method as in [Step 2-2].

[Step 2-17]

This step is a step for obtaining compound (2-15) by reacting compound (2-14) and compound (2-1-3). Compound (2-15) can be produced using the same method as in [Step 2-3].

[Step 2-18]

This step is a step for obtaining compound (2-15) by reacting compound (2-14) and compound (2-1-4). Compound (2-15) can be produced using the same method as in [Step 2-4].

[Step 2-19]

This step is a step for obtaining compound (2-16) by reacting compound (2-14) and compound (2-1-5). Compound (2-16) can be produced using the same method as in [Step 2-5].

[Step 2-20]

This step is a step for obtaining compound (2-17) by reducing the triple bond of compound (2-16) to a double bond. Compound (2-17) can be produced using the same method as in [Step 2-6].

[Step 2-21]

This step is a step for obtaining compound (2-18) by reducing compound (2-17). Compound (2-18) can be produced using the same method as in [Step 2-7].

[Step 2-22]

This step is a step for obtaining compound (2-18) by reducing compound (2-16). Compound (2-18) can be produced using the same method as in [Step 2-8].

[Step 2-23]

This step is a step for obtaining compound (2-19) by reacting compound (2-14) and compound (2-1-6). Compound (2-19) can be produced using the same method as in [Step 2-9].

[Step 2-24]

This step is a step for obtaining compound (2-20) by reducing compound (2-19). Compound (2-20) can be produced using the same method as in [Step 2-10].

[Step 2-25]

This step is a step for obtaining compound (2-21) by reacting compound (2-14) and compound (2-1-1). Compound (2-21) can be obtained by reacting compound (2-14) with compound (2-1-1) in a solvent such as tetrahydrofuran, benzene, toluene, xylene or the like and in the presence of catalyst such as tris(benzylideneacetone)dipalladium (0), dichloro(1,1'-bis(diphenylphosphono)ferrocene)palladium (II), palladium (II) acetate or the like, a phosphine ligand such as 2,2-bis(diphenylphosphono)-1,1'-binaphthyl or the like, and a base such as sodium tert-butoxide or the like. 1 to 3 equivalents of compound (2-1-1) are used with respect to compound (2-14). 0.05 to 0.3 equivalents of catalyst are used with respect to compound (2-14). 1.5 equivalents to an excess of base are used with respect to compound (2-14). 0.25 to 1.5 equivalents of phosphine ligand are used with respect to compound (2-14). The reaction temperature is from 50° C. o the reflux temperature and the reaction time is from 1 to 48 hours.

[Step 2-26]

This step is a step for obtaining compound (2-22) by reacting compound (2-14) and compound (2-5-1). Compound (2-22) can be obtained by reacting compound (2-14) and compound (2-5-1) in a solvent such as tetrahydrofuran, toluene or the like and in the presence of a catalyst such as copper (I) chloride, copper (I) iodide or the like, and a base such as potassium carbonate, cesium carbonate, potassium phosphate, pyridine or the like. 1 to 3 equivalents of compound (2-5-1) are used with respect to compound (2-14). 0.5 to 3 equivalents of catalyst are used with respect to compound (2-14). 2 to 10 equivalents of base are used with respect to compound (2-14). The reaction temperature is from 50° C. to the reflux temperature and the reaction time is from 1 to 48 hours.

[Production Process 2-6] Conversion of a Substituent on Heterobicyclic Ring in Compound (1a)-2

-continued

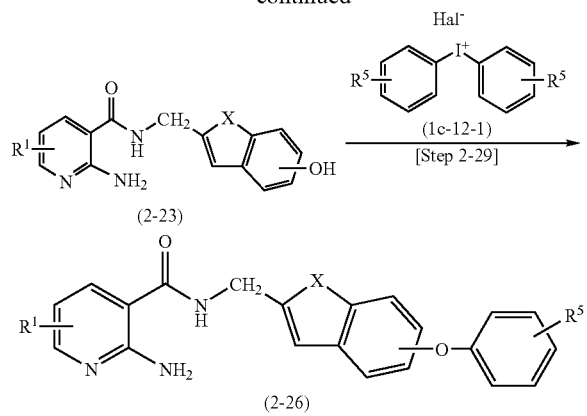

[wherein $R^1$, $R^5$, $R^a$, Hal and X are the same as previously defined, $R_{w1}$ represents a hydrogen atom, halogen, an alkyl group or an alkoxy group, V represents a $C_{3-8}$ cycloalkyl group, a $C_{6-10}$ aryl group, a 5- to 10-membered heterocyclic group or a $C_{1-6}$ alkoxy group, and p1 represents an integer of 1 to 6.]

Commercially available products can be used as is for compound (2-6-1), compound (2-6-2), compound (2-6-3) and compound (1c-12-1), or they can be produced from commercially available products using the known methods.

[Step 2-27]
This step is a step for obtaining compound (2-24) by reacting compound (2-23) and compound (2-6-1). Compound (2-24) can be obtained by reacting compound (2-23) and compound (2-6-1) in the presence of a catalyst and a base. A copper catalyst such as copper (II) acetate or the like can be used for the catalyst. A base such as triethylamine, N,N'-diisopropylethylamine or the like can be used for the base. A solvent such as dichloromethane, tetrahydrofuran, toluene or the like can be used for the solvent, and dichloromethane is used preferably. This reaction is preferably carried out in the presence of oxygen. In order to obtain a favorable result, molecular sieves 4A may also be added. 0.1 to 0.3 equivalents of compound (2-6-1) are used with respect compound. 2 equivalents to an excess of base are used with respect to compound (2-23). 1 to 4 equivalents of catalyst are used with respect to compound (2-23). The reaction temperature is from room temperature to 50° C. and the reaction time is from 24 hours to 5 days.

[Step 2-28]
This step is a step for obtaining compound (2-25) by reacting compound (2-23) and compound (2-6-2). Compound (2-25) can be obtained by reacting compound (2-23) and compound (2-6-2) in a solvent such as N,N-dimethylformamide, N-methylpyrrolidinone, tetrahydrofuran or the like and in the presence of a base such as potassium carbonate, cesium carbonate, sodium hydride or the like. In order to obtain a favorable result, a catalytic amount of sodium iodide or potassium iodide may be added. The reaction temperature is from room temperature to 160° C. and the reaction time is from 10 minutes to 48 hours.

A method using the Mitsunobu reaction can be used as an alternative method. Compound (2-25) can be obtained by reacting compound (2-23), compound (2-6-3), triphenylphosphine and diethylazodicarboxylate or diisopropylazodicarboxylate in a solvent such as dichloromethane, tetrahydrofuran or the like. 1 to 1.5 equivalents of compound (2-6-3) are used with respect to compound (2-23). 1 to 1.5 equivalents of triphenylphosphine are used with respect to compound (2-23). 1 to 1.5 equivalents of diethylazodicarboxylate or diisopropylazodicarboxylate are used with respect to compound (2-23). The reaction temperature is from room temperature to the reflux temperature and the reaction time is from 5 minutes to 24 hours.

[Step 2-29]
This step is a step for obtaining compound (2-26) by reacting compound (2-23) and compound (1c-12-1). Compound (2-26) can be produced using the same method as in [Step 1-21].

[Production Process 2-7] Conversion of a Substituent on Heterobicyclic Ring in Compound (1a)-3

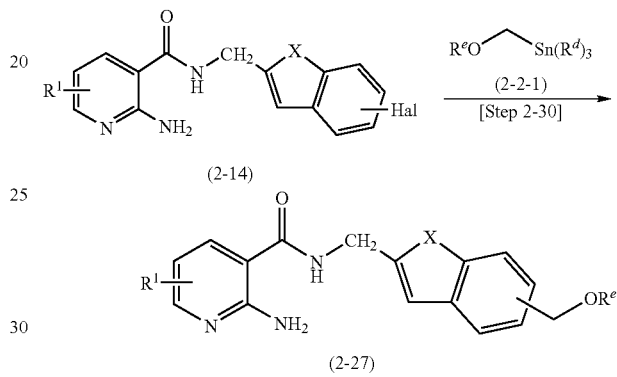

[wherein $R^1$, Hal, $R^d$, $R^e$ and X are the same as previously defined.]

[Step 2-30]
This step is a step for obtaining compound (2-27) by reacting compound (2-14) and compound (2-2-1). Compound (2-27) can be produced using the same method as in [Step 2-11].

(Production Process of Compound (2-2-1))

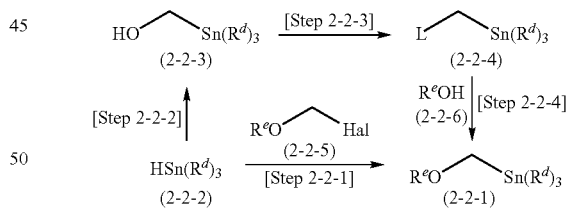

[wherein L, $R^d$ and $R^e$ are the same as previously defined.]

Commercially available products can be used as is for compound (2-2-2), compound (2-2-5) and compound (2-2-6), or they can be produced from commercially available products using the known methods.

[Step 2-2-1]
This step is a step for obtaining compound (2-2-1) by reacting compound (2-2-2) and compound (2-2-5). Compound (2-2-1) can be obtained by extracting a hydrogen atom of compound (2-2-2) with a strong base such as lithium diisopropylamine or the like in a solvent such as tetrahydrofuran or the like and then reacting with compound (2-2-5). A compound such as chloromethyl ethyl ether, chloromethyl benzyl ether or the like can be used for compound (2-2-5). 1 to 2 equivalents of strong base are used with respect to compound (2-2-2). 1 to 2 equivalents of compound (2-2-5) are used with respect to compound (2-2-2). The reaction temperature is from −78° C. to the reflux temperature and the reaction time is from 1 to 24 hours.

[Step 2-2-2]

This step is a step for obtaining compound (2-2-3) by reacting compound (2-2-2) and a formaldehyde equivalent. Compound (2-2-3) can be obtained by extracting a hydrogen atom of compound (2-2-2) with a base such as lithium diisopropylamide or the like in a solvent such as tetrahydrofuran or the like and then reacting with paraformaldehyde. 1 to 2 equivalents of strong base are used with respect to compound (2-2-2). 1 to 2 equivalents of formaldehyde equivalent are used with respect to compound (2-2-2). The reaction temperature is from −78° C. to the reflux temperature and the reaction time is from 1 to 24 hours.

[Step 2-2-3]

This step is a step for obtaining compound (2-2-4) by converting the hydroxyl group of compound (2-2-3) to a leaving group.

In the case L is a methanesulfonyloxy group, p-toluenesulfonyloxy group or the like, compound (2-2-4) can be obtained by reacting compound (2-2-3) with sulfonyl halide such as methanesulfonyl chloride, p-toluenesulfonyl chloride or the like in a solvent such as dichloromethane or the like and in the presence of an organic base such as triethylamine or the like. 1 to 3 equivalents of the organic base are used with respect to compound (2-2-3). 1 to 2 equivalents of sulfonyl halide are used with respect to compound (2-2-3). The reaction temperature is from 0° C. to the reflux temperature and the reaction time is from 10 minutes to 24 hours.

In the case L is a bromine atom or an iodine atom, compound (2-2-4) can be obtained by allowing a halogenation agent such as carbon tetrabromide, N-bromosuccinimide, N-iodosuccinimide or the like to act on compound (2-2-3) in a solvent such as dichloromethane or the like and in the presence of triphenylphosphine. 1 to 2 equivalents of triphenylphoshine are used with respect to compound (2-2-3). 1 to 2 equivalents of halogenation agent are used with respect to compound (2-2-3). The reaction temperature is from 0° C. to room temperature and the reaction time is from 10 minutes to 24 hours.

[Step 2-2-4]

This step is a step for obtaining compound (2-2-1) by reacting compound (2-2-4) and compound (2-2-6). Compound (2-2-1) can be obtained by extracting a hydrogen atom of compound (2-2-6) by using a base such as sodium hydride or the like in a solvent such as N,N-dimethylformamide or the like and then reacting with compound (2-2-4). 1 to 10 equivalents of compound (2-2-6) are used with respect to compound (2-2-4). 1 to 10 equivalents of base are used with respect to compound (2-2-4). The reaction temperature is from 0° C. to the reflux temperature and the reaction time is from 10 minutes to 24 hours.

EXAMPLES

The compounds according to the present invention can be produced in accordance with, for example, the methods described in the following production examples and examples. However, these are only exemplary and are not intended under any circumstances to limit the compounds according to the present invention to any of the following specific examples thereof.

Example 1

2,6-Diamino-N-(6-benzyloxy-benzofuran-2-ylm-ethyl)-nicotinamide

To a dimethylsulfoxide (10 mL) solution of C-(6-benzyloxy-benzofuran-2-yl)-methylamine (300 mg, 1.18 mmol) described in Production Example 1-2-4 were added 2,6-diaminonicotinic acid (181 mg) described in Production Example 1-1-4, 1-hydroxybenzotriazole (319 mg, 2.36 mmol), triethylamine (329 μL, 2.36 mmol) and 1-ethyl-3-(3-dimethylaminopropyl)carbodiimide hydrochloride (452 mg, 2.36 mmol) at room temperature, which was stirred at room temperature for 26 hours. To the reaction solution was added water at room temperature followed by extracting with ethyl acetate. After washing the organic layer with water and sat. NaCl, the organic layer was dried over anhydrous magnesium sulfate and filtered. The filtrate was concentrated under a reduced pressure and the residue was purified by silica gel column chromatography (ethyl acetate) to obtain the title compound (227 mg, 60%) as a white solid.

$^1$H-NMR spectrum (DMSO-d$_6$) δ (ppm): 4.47 (2H, d, J=5.5 Hz), 5.13 (2H, s), 5.67 (1H, d, J=8.6 Hz), 6.11 (2H, brs), 6.59 (1H, s), 6.91 (1H, dd, J=2.2 Hz, J=8.4 Hz), 6.97 (2H, brs), 7.23 (1H, d, J=2.0 Hz), 7.32 (1H, t, J=7.3 Hz), 7.39 (2H, t, J=7.3 Hz), 7.43 (1H, d, J=8.4 Hz), 7.46 (2H, d, J=7.3 Hz), 7.68 (1H, d, J=8.6 Hz), 8.34 (1H, t, J=5.5 Hz).

The starting material in the form of 2,6-diaminonicotinic acid was synthesized according to the method described below.

Production Example 1-1-1

2-(2-Cyanoethyl)3,3-diaminopropenoic acid ethyl ester (1-Ethoxyformimidoyl)1-acetic acid ethyl ester hydrochloride (50 g, 0.26 mol) was suspended in an ammonia-ethanol solution (300 mL, room temperature, prepared by saturating ethanol with ammonia gas), which was stirred at room temperature for 4 hours. Following completion of the reaction, the precipitated salt was filtered out and the filtrate was concentrated under a reduced pressure to one-third the original volume at room temperature. To this filtrate was added hydrochloric acid-methanol (130 mL, hydrochloric acid content: 7.5%), followed by concentrating under a reduced pressure to obtain 3,3-diamino-acrylic acid ethyl ester hydrochloride (40 g, 0.24 mol, 92%) as a solid.

The resulting 3,3-diamino-acrylic acid ethyl ester hydrochloride (2.2 g, 13.2 mmol) was suspended in tetrahydrofuran (40 mL) followed by the addition of triethylamine (2 mL, 14.3 mmol) and acrylonitrile (1.2 mL, 19.3 mmol) and refluxing while heating for 6 hours. Following completion of the reaction, the resulting triethylamine hydrochloride was filtered out and the filtrate was concentrated to obtain the title compound (0.6 g, 3.3 mmol, 25%).

$^1$H-NMR spectrum (CDCl$_3$) δ (ppm): 1.26 (3H, t, J=7.2 Hz), 2.42-2.49 (2H, m), 2.50-2.57 (2H, m), 4.12 (2H, q, J=7.2 Hz), 4.22 (2H, brs), 6.45 (2H, brs).

Production Example 1-1-2

2,6-Diamino-4,5-dihydronicotinic acid ethyl ester

A tetrahydrofuran (7 mL) solution of 2-(2-cyanoethyl)3,3-diaminopropenoic acid ethyl ester (0.55 g, 3 mmol) described in Production Example 1-1-1 was dropped into a tetrahydrofuran (7 mL) suspension of sodium hydride (208 mg, 5.2 mmol, 60% in oil), which was refluxed while heating and stirring for 19 hours 20 minutes. Following completion of the reaction, the reaction mixture was poured into ice water and extracted with ethyl acetate. The organic layer was dried over anhydrous magnesium sulfate and then concentrated to obtain the title compound (0.188 g, 1 mmol, 34%) as a crude product.

$^1$H-NMR spectrum (CDCl$_3$) δ (ppm): 1.27 (3H, t, J=7.2 Hz), 2.28-2.34 (2H, m), 2.46-2.52 (2H, m), 4.14 (2H, q, J=7.2 Hz).

Production Example 1-1-3

2,6-Diamino-nicotinic acid ethyl ester

To a tetrahydrofuran (300 mL) solution of 2,6-diamino-4,5-dihydronicotinic acid ethyl ester (4.5 g, 24.6 mmol) described in Production Example 1-1-2 was added 2,3-dichloro-5,6-dicyano-1,4-benzoquinone (5.6 g, 24.7 mmol), which was stirred at room temperature for 40 minutes. Next, the reaction mixture was concentrated and the resulting residue was purified by NH silica gel column chromatography (ethyl acetate) to obtain a target compound as a solid. This solid was washed with hexane and dried to obtain the title compound (3.1 g, 17.1 mmol, 69.5%).

$^1$H-NMR spectrum (CDCl$_3$) δ (ppm): 1.35 (3H, t, J=7.2 Hz), 4.27 (2H, q, J=7.2 Hz), 4.60 (2H, brs), 5.82 (1H, d, J=6.4 Hz), 7.90 (1H, d, J=8.4 Hz).

Production Example 1-1-4

2,6-Diamino-nicotinic acid 2,6-diamino-nicotinic acid ethyl ester (2 g, 11 mmol) described in Production Example 1-1-3 was dissolved in ethanol (15 mL) followed by the addition of 1 N aqueous sodium hydroxide solution (15 mL) and stirring for 2 hours while heating under reflux. After allowing the reaction mixture to return to room temperature, the ethanol was distilled off under a reduced pressure and the residue was cooled with ice and neutralized with 1 N hydrochloric acid. After filtering the precipitated solid and washing with water, the solid was dried to obtain the title compound (1.72 g, 11 mmol, quantitative).

$^1$H-NMR spectrum (DMSO-d$_6$) δ (ppm): 5.70 (1H, d, J=8.4 Hz), 6.31 (2H, brs), 6.58-7.12 (1H, brs), 7.62 (1H, d, J=8.4 Hz).

The starting material in the form of C-(6-benzyloxy-benzofuran-2-yl)-methylamine was synthesized according to the method described below.

Production Example 1-2-1

6-Benzyloxy-benzofuran-2-carboxylic acid ethyl ester

To a N,N-dimethylformamide (200 mL) solution of 4-benzyloxy-2-hydroxybenzaldehyde (18.6 g, 81.4 mmol) were added ethyl bromoacetate (9.94 mL, 89.6 mmol) and potassium carbonate (22.6 g, 163 mmol) at room temperature, which was stirred at 125° C. for 3 hours. To the reaction mixture was added water at room temperature followed by extraction with ethyl acetate. After washing the organic layer with water and sat. NaCl, the organic layer was dried over anhydrous magnesium sulfate and filtered followed by concentrating the filtrate under a reduced pressure. The residue was purified by NH silica gel column chromatography (heptane:ethyl acetate=7:3) to obtain the title compound (18.4 g, 76%) as a white solid.

$^1$H-NMR spectrum (DMSO-d$_6$) δ (ppm): 1.33 (3H, t, J=7.1 Hz), 4.34 (2H, q, J=7.1 Hz), 5.19 (2H, s), 7.07 (1H, dd, J=2.2 Hz, J=8.6 Hz), 7.35 (1H, t, J=7.1 Hz), 7.37-7.43 (3H, m), 7.49 (2H, d, J=7.0 Hz), 7.67-7.69 (2H, m).

Production Example 1-2-2

(6-Benzyloxy-benzofuran-2-yl)-methanol

To a tetrahydrofuran (370 mL) solution of 6-benzyloxy-benzofuran-2-carboxylic acid ethyl ester (18.4 g, 62.1 mmol) described in Production Example 1-2-1 was added lithium aluminum hydride (7.07 g, 186 mmol) at 0° C., which was stirred at room temperature for 4 hours. To the reaction mixture were added water (7.07 mL), 5 N aqueous sodium hydroxide solution (7.07 mL) and water (21.2 mL) at 0° C. After filtering the mixture through Celite, the filtrate was concentrated under a reduced pressure. The residue was purified by silica gel column chromatography (heptane:ethyl acetate=1:1) to obtain the title compound (14.2 g, 90%) as a white solid.

$^1$H-NMR spectrum (DMSO-d$_6$) δ (ppm): 4.51 (2H, d, J=5.1 Hz), 5.14 (2H, s), 5.39 (1H, t, J=5.3 Hz), 6.65 (1H, s), 6.92 (1H, d, J=8.6 Hz), 7.23 (1H, s), 7.31-7.48 (6H, m).

Production Example 1-2-3

2-(6-Benzyloxy-benzofuran-2-ylmethyl)-isoindole-1,3-dione

To a tetrahydrofuran (300 mL) solution of (6-benzyloxy-benzofuran-2-yl)-methanol (14.2 g, 55.8 mmol) described in Production Example 1-2-2 were added phthalimide (9.03 g, 61.4 mmol), triphenylphosphine (17.6 g, 67 mmol) and diethylazodicarboxylate (29.2 g, 67 mmol) at 0° C., which was stirred at room temperature for 7 hours 30 minutes. To the reaction mixture was added water at room temperature followed by extraction with ethyl acetate. After washing the organic layer with water and sat. NaCl, the organic layer was dried over anhydrous magnesium sulfate and filtered. The filtrate was concentrated under a reduced pressure and the residue was purified by NH silica gel column chromatography (heptane:ethyl acetate=3:1) to obtain a mixture of the title compound and a by-product (14.3 g) as a white solid. This was then used in the next reaction without additional purification.

Production Example 1-2-4

C-(6-Benzyloxy-benzofuran-2-yl)-methylamine

To a mixed ethanol (50 mL) and tetrahydrofuran (50 mL) solution of 2-(6-benzyloxy-benzofuran-2-ylmethyl)-isoindole-1-dione (5.60 g, 14.6 mmol) described in Production Example 1-2-3 was added hydrazine hydrate (7.08 mL, 146 mmol) at room temperature, which was stirred for 1 hour while heating under reflux. To the reaction solution was added water was added at room temperature followed by extracting with ethyl acetate. After washing the organic layer with sat. NaCl, the organic layer was dried over anhydrous magnesium sulfate and filtered. The filtrate was concentrated under a reduced pressure and the residue was purified by NH silica gel column chromatography (ethyl acetate) to obtain the title compound (1.83 g, 50%) as a pale yellow oil.

¹H-NMR spectrum (DMSO-d₆) δ (ppm): 3.76 (2H, s), 5.12 (2H, s), 6.55 (1H, s), 6.89 (1H, dd, J=2.0 Hz, 8.4 Hz), 7.18 (1H, s), 7.31 (1H, t, J=6.8 Hz), 7.36-7.46 (5H, m).

Example 2

2,6-Diamino-N-(6-ethoxy-benzofuran-2-ylmethyl)-nicotinamide

To a tetrahydrofuran (2 mL) solution of 2,6-diamino-N-(6-hydroxy-benzofuran-2-ylmethyl)-nicotinamide (101 mg, 339 μmol) described in Production Example 2-1 was added 5 N aqueous sodium hydroxide solution (68 μL, 339 μmol) at room temperature. The reaction solution was concentrated under a reduced pressure to obtain a sodium salt of 2,6-diamino-N-(6-hydroxy-benzofuran-2-ylmethyl)-nicotinamide (130 mg). To an N,N-dimethylformamide (500 μL) solution of the resulting sodium salt (4 mg, 13 μmol) was added bromoethane (2.85 mg, 26.2 μmol) at room temperature, which was stirred at room temperature for 2 hours. After filtering the reaction solution, the filtrate was purified by reverse phase high-performance liquid chromatography (using an acetonitrile-aqueous mobile phase (containing 0.1% trifluoroacetic acid)) to obtain the title compound (2.6 mg, 61%) as a trifluoroacetatic acid salt.

MS m/e (ESI): 327.15 (MH⁺)

The starting material in the form of 2,6-diamino-N-(6-hydroxy-benzofuran-2-ylmethyl)-nicotinamide was synthesized according to the method described below.

Production Example 2-1

2,6-Diamino-N-(6-hydroxy-benzofuran-2-ylmethyl)-nicotinamide

To a trifluoroacetic acid (5 mL) solution of 2,6-diamino-N-(6-benzyloxy-benzofuran-2-ylmethyl)-nicotinamide (238 mg, 612 μmol) described in Example 1 was added thioanisole (287 μL, 2.45 mmol) at 0° C., which was stirred at room temperature for 2 hours. To the reaction solution were added sodium bicarbonate and water at 0° C., followed by extraction with ethyl acetate. After washing the organic layer with sat. NaCl, the organic layer was dried over anhydrous magnesium sulfate and filtered. The filtrate was concentrated under a reduced pressure and the residue was purified by NH silica gel column chromatography (ethyl acetate:methanol=10:1) to obtain the title compound (101 mg, 55%) as a pale brown solid.

¹H-NMR spectrum (DMSO-d₆) δ (ppm): 4.43 (2H, d, J=5.7 Hz), 5.65 (1H, d, J=8.6 Hz), 6.08 (2H, brs), 6.50 (1H, s), 6.67 (1H, dd, J=2.4 Hz, 8.4 Hz), 6.84 (1H, s), 6.95 (2H, brs), 7.29 (1H, d, J=8.4 Hz), 7.66 (1H, d, J=8.6 Hz), 8.30 (1H, t, J=5.7 Hz), 9.45 (1H, s).

Example 3

2,6-Diamino-N-(6-cyclopropylmethoxy-benzofuran-2-ylmethyl)-nicotinamide

To an N,N-dimethylformamide (8 mL) solution of a sodium salt of 2,6-diamino-N-(6-hydroxy-benzofuran-2-ylmethyl)-nicotinamide (400 mg, 1.25 mmol) obtained in the same manner as Example 2 was added cyclopropylmethyl bromide (364 μL, 3.75 mmol) at room temperature, which was stirred at room temperature for 20 hours. To the reaction solution was added water at room temperature followed by extraction with ethyl acetate. After washing the organic layer with water and sat. NaCl, the organic layer was dried over anhydrous magnesium sulfate and filtered. The filtrate was concentrated under a reduced pressure and the residue was purified by NH silica gel column chromatography (ethyl acetate) to obtain the title compound (99 mg, 23%) as a white solid.

MS m/e (ESI): 353.25 (MH⁺)

¹H-NMR spectrum (DMSO-d₆) δ (ppm): 0.019 (2H, dt, J=4.9 Hz, 10.1 Hz), 0.27 (2H, dt, J=4.8 Hz, 12.6 Hz), 0.90-0.94 (1H, m), 3.52 (2H, d, J=7.1 Hz), 4.17 (2H, d, J=5.5 Hz), 5.37 (1H, d, J=8.6 Hz), 5.81 (2H, brs), 6.27 (1H, s), 6.53 (1H, dd, J=2.4 Hz, 8.6 Hz), 6.67 (2H, brs), 6.80 (1H, s), 7.10 (1H, d, J=8.4 Hz), 7.38 (1H, d, J=8.2 Hz), 8.04 (1H, t, J=5.7 Hz).

Example 4

2-Amino-N-(6-benzyloxy-benzofuran-2-ylmethyl)-6-methoxymethyl-nicotinamide

To a N,N-dimethylformamide (8 mL) solution of C-(6-benzyloxy-benzofuran-2-yl)-methylamine (400 mg, 1.58 mmol) described in Production Example 1-2-4 were added 2-amino-6-methoxymethyl-nicotinic acid (316 mg, 1.74 mmol) described in Production Example 4-1-5, triethylamine (660 μL, 4.74 mmol) and benzotriazol-1-yloxytris(dimethylamino)phosphonium hexafluorophosphate (908 mg, 2.05 mmol) at room temperature, which was stirred at room temperature for 2 hours 30 minutes. To the reaction solution was added water at room temperature followed by extraction with ethyl acetate. After washing the organic layer with water and sat. NaCl, the organic layer was dried over anhydrous magnesium sulfate and filtered. The filtrate was concentrated under a reduced pressure and purified by silica gel column chromatography (heptane:ethyl acetate=1:2) to obtain the title compound (454 mg, 69%) as a white solid.

¹H-NMR spectrum (DMSO-d₆) δ (ppm): 3.32 (3H, s), 4.28 (2H, s), 4.52 (2H, d, J=5.3 Hz), 5.11 (2H, s), 6.59 (1H, d, J=7.9 Hz), 6.64 (1H, s), 6.90 (1H, dd, J=2.4 Hz, 8.6 Hz), 7.13 (2H, s), 7.22 (1H, d, J=1.8 Hz), 7.31 (1H, d, J=7.3 Hz), 7.37 (2H, t, J=7.7 Hz), 7.44 (3H, t, J=8.4 Hz), 7.97 (1H, d, J=7.9 Hz), 8.96 (1H, t, J=5.3 Hz).

The starting material in the form of 2-amino-6-methoxymethyl-nicotinic acid was synthesized according to the method described below.

Production Example 4-1-1A

2-Amino-6-chloro-nicotinic acid 2,6-Dichloronicotinic acid (0.38 g, 2 mmol) and copper (I) iodide (720 mg, 3.8 mmol) were added to liquid ammonia (approx. 20 mL) in a sealed tube at −78° C., which was heated for 25 hours (oil bath temperature: 115° C.). The oil bath temperature was raised to 125° C. followed by additionally heating for 14 hours 30 minutes. The reaction mixture was allowed to return to room temperature followed by distilling off the ammonia. The insoluble material that precipitated following addition of methanol was filtered out and the filtrate was concentrated to obtain the title compound (0.25 g, 1.45 mmol, 72%) as a solid.

¹H-NMR spectrum (DMSO-d₆) δ (ppm): 6.63 (1H, d, J=8.0 Hz), 7.55 (2H, brs), 8.02 (1H, d, J=8.0 Hz).

Production Example 4-1-1B

2-Amino-6-chloro-nicotinic acid

To a mixture of 2,6-dichloronicotinic acid (40 g (purity: 90%), 0.19 mol), acetoamide (80 g, 1.4 mol), potassium carbonate (78 g, 0.56 mol), copper (I) chloride (0.93 g, 9.4 mmol) and xylene (80 mL) was added tris(2-(2-methoxyethoxy)ethyl)amine (3.0 mL, 9.4 mmol), which was stirred overnight at 145° C. After allowing to cool on standing, to the reaction mixture was added copper (I) chloride (0.46 g, 4.6 mmol), followed by stirring overnight at 145° C. After cooling the reaction mixture to 105° C., water (100 mL) was added followed by stirring for 1 hour at the same temperature and allowing to cool to room temperature on standing. After neutralizing the reaction mixture with 5 N hydrochloric acid (150 mL) and aqueous citric acid, ethyl acetate was added. This mixture was filtered through Celite. After separating the organic phase and washing with sat. NaCl, the solvent was concentrated under a reduced pressure. The residue was purified by silica gel column chromatography (ethyl acetate) and recrystallized from an ethyl acetate-hexane system to obtain the title compound (1.4 g, 8.3 mmol, 4.5%) as white crystals.
¹H-NMR spectrum (DMSO-d₆) δ (ppm): 6.61 (H1, d, J=8.1 Hz), 7.53 (2H, brs), 8.01 (1H, d, J=8.1 Hz).

Production Example 4-1-2

2-Amino-6-chloro-nicotinic acid methyl ester

Concentrated sulfuric acid (25 mL) and 2-amino-6-chloronicotinic acid (4.3 g, 25 mmol) described in Production Example 4-1-1A (or 4-1-1B) were added to methanol (50 mL) while cooling with ice followed by stirring for 5 hours at 70° C. After allowing to cool on standing, the reaction mixture was neutralized with sodium bicarbonate (90 g). The resulting solid was filtered to obtain the title compound (3.2 g, 17 mmol, 68%) as a pale brown solid.
¹H-NMR spectrum (CDCl₃) δ (ppm): 3.88 (3H, s), 6.62 (1H, d J=8.2 Hz), 8.05 (1H, d, J=8.1 Hz).

Production Example 4-1-3

Tributyl-methoxymethyl-stannane n-Butyl lithium (2.4 M, n-hexane solution, 25 mL, 61 mmol) was dropped into a mixture of diisopropylamine (9.4 mL, 67 mmol) and tetrahydrofuran (150 mL) at −78° C. followed by stirring for 30 minutes at the same temperature. Tributyl tin hydride (16 mL, 61 mmol) was dropped in at the same temperature followed by stirring for 30 minutes while cooling with ice. The reaction mixture was brought to a temperature of −78° C. followed by dropping in chloromethyl methyl ether (4.6 mL, 61 mmol) and gradually warming to room temperature. Water (100 mL) was added to the reaction mixture followed by extraction with diethyl ether (300 mL). After washing the organic layer with sat. NaCl, the organic layer was distilled under a reduced pressure. The residue was purified by neutral silica gel column chromatography (heptane/ethyl acetate=30/1) to obtain the title compound (18 g, 0.52 mmol, 86%) as a colorless oil.
¹H-NMR spectrum (CDCl₃) δ (ppm): 0.88-0.93 (15H, m), 1.26-1.35 (6H, m), 1.47-1.55 (6H, m), 3.30 (3H, s), 3.71 (2H, t, J=6.8 Hz).

Production Example 4-1-4

2-Amino-6-methoxymethyl-nicotinic acid methyl ester

A mixture of 2-amino-6-chloro-nicotinic acid methyl ester (1.4 g, 7.6 mmol) described in Production Example 4-1-2, tributyl methoxymethyl stannane (3.1 g, 9.1 mmol) described in Production Example 4-1-3, tetrakis(triphenylphosphine) palladium (440 mg, 0.38 mmol) and N-methylpyrrolidinone (20 mL) was stirred for 3.5 hours at 130° C. The reaction mixture was allowed to cool on standing followed by the addition of aqueous potassium fluoride solution while cooling with ice and filtering through Celite. After washing the organic layer with sat. NaCl, the organic layer was distilled under a reduced pressure. The residue was purified by silica gel column chromatography (heptane/ethyl acetate=2/1) to obtain the title compound (0.93 g, 4.7 mmol, 63%) as a pale brown oil.
¹H-NMR spectrum (CDCl₃) δ (ppm): 3.47 (3H, s), 3.88 (3H, s), 4.41 (2H, s), 6.74 (1H, d, J=7.9 Hz), 8.14 (1H, d, J=7.9 Hz).

Production Example 4-1-5

2-Amino-6-methoxymethyl-nicotinic acid

To a mixture of 2-amino-6-methoxymethyl-nicotinic acid methyl ester (2.9 g, 15 mmol) described in Production Example 4-1-4, tetrahydrofuran (30 mL), methanol (7.5 mL) and water (7.5 ml) was added sodium hydroxide monohydrate (1.2 g, 29 mmol), which was stirred overnight at room temperature. To the reaction mixture was added acetic acid (1.7 mL, 29 mmol), followed by distilling off the solvent under a reduced pressure. The residue was dissolved in methanol/ethyl acetate (1/3) and filtered using silica gel. The filtrate was collected, concentrated under a reduced pressure and the residue was washed with water to obtain the title compound (2.1 g, 12 mmol, 80%) as a pale yellow solid.
¹H-NMR spectrum (DMSO-d₆) δ (ppm): 3.32 (3H, s), 4.29 (2H, s), 6.61 (1H, d, J=7.9 Hz), 7.16 (2H, brs), 8.02 (1H, d, J=7.9 Hz).

Example 5

N-(6-Allyloxy-benzofuran-2-ylmethyl)-2-amino-6-methoxymethyl-nicotinamide

To a tetrahydrofuran (7 ml) solution of 2-amino-N-(6-hydroxy-benzofuran-2-ylmethyl)-6-methoxymethyl-nicotinamide (331 mg, 1.01 mmol) described in Production Example 5-1 was added 5 N aqueous sodium hydroxide solution (202 μL, 1.01 mmol) at room temperature. The reaction solution was concentrated under a reduced pressure to obtain 2-amino-N-(6-hydroxy-benzofuran-2-ylmethyl)-6-methoxymethyl-nicotinamide (416 mg). To an N,N-dimethylformamide (1 mL) solution of the resulting sodium salt (30 mg, 86 μmol) was added allyl bromide (29.7 μL, 344 μmol), followed by stirring for 23 hours at room temperature. Water was added to the reaction solution at room temperature followed by extraction with ethyl acetate. The organic layer was washed with water and sat. NaCl followed by drying over anhydrous magnesium sulfate and filtering. The filtrate was concentrated under a reduced pressure and the residue was purified by NH silica gel column chromatography (heptane:ethyl acetate=1:2) to obtain the title compound (17 mg, 54%) as a white solid.

MS m/e (ESI): 368.28 (MH+)

¹H-NMR spectrum (DMSO-d₆) δ (ppm): 3.40 (3H, s), 4.30 (2H, s), 4.55 (2H, d, J=5.5 Hz), 4.59 (2H, d, J=5.3 Hz), 5.26 (1H, d, J=10.4 Hz), 5.41 (1H, dd, J=1.7 Hz, 17.2 Hz), 6.00-6.11 (1H, m), 6.62 (1H, d, J=7.7 Hz), 6.66 (1H, s), 6.87 (1H, dd, J=2.2 Hz, 8.4 Hz), 7.16 (2H, s), 7.17 (1H, s), 7.44 (1H, d, J=8.4 Hz), 8.00 (1H, d, J=7.9 Hz), 8.99 (1H, t, J=5.5 Hz).

The starting material in the form of 2-amino-N-(6-hydroxy-benzofuran-2-ylmethyl)-6-methoxymethyl-nicotinamide was synthesized according to the method described below.

Production Example 5-1

2-amino-N-(6-hydroxy-benzofuran-2-ylmethyl)-6-methoxymethyl-nicotinamide

To a trifluoroacetic acid (11 mL) solution of 2-amino-N-(6-benzyloxy-benzofuran-2-ylmethyl)-6-methoxymethyl-nicotinamide (557 mg, 1.33 mmol) described in Example 4 was added thioanisole (626 µL, 5.35 mmol) at 0° C., which was stirred at 0° C. for 3 hours. To the reaction solution were added sodium bicarbonate and water at 0° C. followed by extraction with ethyl acetate and tetrahydrofuran. The organic layer was washed with sat. NaCl followed by drying over anhydrous magnesium sulfate and filtering. The filtrate was concentrated under a reduced pressure and the residue was purified by NH silica gel column chromatography (ethyl acetate:methanol=10:1) to obtain the title compound (331 mg, 76%) as a white solid.

¹H-NMR spectrum (DMSO-d₆) δ (ppm): 3.32 (3H, s), 4.27 (2H, s), 4.49 (2H, d, J=4.8 Hz), 6.57 (1H, s), 6.59 (1H, d, J=8.2 Hz), 6.67 (1H, dd, J=2.0 Hz, 8.4 Hz), 6.84 (1H, s), 7.12 (2H, brs), 7.30 (1H, d, J=8.4 Hz), 7.97 (1H, d, J=7.9 Hz), 8.93 (1H, t, J=5.3 Hz), 9.45 (1H, s).

Example 6

2-Amino-N-(6-cyclopropylmethoxy-benzofuran-2-ylmethyl)-6-methoxymethyl-nicotinamide To a tetrahydrofuran (7 mL) solution of 2-amino-N-(6-hydroxy-benzofuran-2-ylmethyl)-6-methoxymethyl-nicotinamide (331 mg, 1.01 mmol) described in Production Example 5-1 was added 5 N aqueous sodium hydroxide solution (202 µL, 1.01 mmol) at room temperature. The reaction solution was concentrated under a reduced pressure to obtain 2-amino-N-(6-hydroxy-benzofuran-2-ylmethyl)-6-methoxymethyl-nicotinamide (416 mg). To an N,N-dimethylformamide (1 mL) solution of the resulting sodium salt (30 mg, 86 µmol) was added cyclopropylmethyl bromide (33.3 µL, 343 µmol) at room temperature, which was stirred at room temperature for 17.5 hours. Water was added to the reaction solution at room temperature followed by extracting with ethyl acetate. The organic layer was washed with water and sat. NaCl, followed by drying over anhydrous magnesium sulfate and filtering. The filtrate was concentrated under a reduced pressure and the residue was purified by NH silica gel column chromatography (heptane:ethyl acetate=1:2) to obtain the title compound (19 mg, 58%) as a white solid.

MS m/e (ESI): 382.27 (MH+)

¹H-NMR spectrum (DMSO-d₆) δ (ppm): 0.02 (2H, dt, J=5.2 Hz, 10.4 Hz), 0.27 (2H, dt, J=6.0 Hz, 12.0 Hz), 0.91-0.96 (1H, m), 3.04 (3H, s), 3.53 (2H, d, J=7.1 Hz), 3.99 (2H, s), 4.24 (2H, d, J=5.3 Hz), 6.31 (1H, d, J=7.9 Hz), 6.34 (1H, s), 6.54 (1H, dd, J=1.5 Hz, 8.6 Hz), 6.82 (1H, s), 6.85 (2H, s), 7.12 (1H, d, J=8.8 Hz), 7.69 (1H, d, J=8.1 Hz), 8.68 (1H, t, J=5.2 Hz).

Example 7

2-Amino-N-(5-benzyloxy-benzofuran-2-ylmethyl)-6-methoxymethyl-nicotinamide

To a N,N-dimethylformamide (5 mL) solution of C-(5-benzyloxy-benzofuran-2-yl)-methylamine (135 mg, 533 µmol) described in Production Example 7-1-6 were added 2-amino-6-methoxymethyl-nicotinic acid (107 mg, 586 µmol) described in Production Example 4-1-5, triethylamine (223 µL, 1.60 mmol) and benzotriazol-1-yloxytris(dimethylamino)phosphonium hexafluorophosphate (306 mg, 693 µmol) at room temperature, which was stirred at room temperature for 27 hours. Water was added to the reaction solution at room temperature followed by extracting with ethyl acetate. The organic layer was washed with water and sat. NaCl followed by drying over anhydrous magnesium sulfate and filtering. The filtrate was concentrated under a reduced pressure and the residue was purified by silica gel column chromatography (heptane:ethyl acetate=1:5) to obtain the title compound (166 mg, 75%) as a white solid.

¹H-NMR spectrum (DMSO-d₆) δ (ppm): 3.35 (3H, s), 4.03 (2H, s), 4.56 (2H, d, J=5.3 Hz), 5.11 (2H, s), 6.62 (1H, d, J=8.2 Hz), 6.67 (1H, s), 6.93 (1H, dd, J=2.6 Hz, 9.0 Hz), 7.15 (2H, brs), 7.19 (1H, d, J=2.6 Hz), 7.32 (1H, t, J=7.1 Hz), 7.39 (2H, t, J=7.1 Hz), 7.43-7.47 (3H, m), 8.00 (1H, d, J=7.9 Hz), 9.01 (1H, t, J=5.5 Hz).

The starting material in the form of C-(5-benzyloxy-benzofuran-2-yl)-methylamine was synthesized according to the method described below.

Production Example 7-1-1

2,5-Bis-benzyloxy-benzaldehyde

To an N,N-dimethylformamide (100 mL) solution of 2,5-dihydroxybenzaldehyde (10.0 g, 72.4 mmol) were added sodium hydride (5.79 g, 145 mmol) and benzyl bromide (18.9 mL, 159 mmol) at 0° C., which was stirred at room temperature for 24 hours. Water was added to the reaction solution at 0° C. followed by extraction with ethyl acetate. The organic layer was washed with water and sat. NaCl, followed by drying over anhydrous magnesium sulfate and filtering. The filtrate was concentrated under a reduced pressure and the residue was purified by silica gel column chromatography (heptane:ethyl acetate=4:1) to obtain the title compound (17.6 g, 76%) as a white solid.

¹H-NMR spectrum (DMSO-d₆) δ (ppm): 5.11 (2H, s), 5.24 (2H, s), 7.27-7.50 (13H, m), 10.38 (1H, s).

Production Example 7-1-2

5-Benzyloxy-2-hydroxy-benzaldehyde

To a mixed suspension of magnesium (305 mg, 12.6 mmol) in diethyl ether (7.5 mL) and toluene (7.5 mL) was added bromine (354 µL, 6.91 mmol) at 0° C., which was stirred at room temperature for 5 minutes under nitrogen atmosphere and was refluxed while heating for 5 minutes. After the reaction mixture was cooled to room temperature, a toluene (20 mL) solution of 2,5-bis-benzyloxy-benzaldehyde (2.00 g, 6.28 mmol) described in Production Example 7-1-1 were added followed by stirring at room temperature for 24 hours under nitrogen atmosphere. Moreover, after stirring for 6 hours while refluxing while heating, the reaction mixture was cooled to room temperature. The precipitated solid was filtered out and washed with toluene. 1 N aqueous hydrochloric acid solution (20 mL) was added to the filtered solid followed by stirring for 1 hour while refluxing and heating. The reaction solution was allowed to cool to room temperature followed by extraction with ethyl acetate. The organic layer was washed with sat. NaCl followed by drying over anhydrous magnesium sulfate and filtering. The filtrate was concentrated under a reduced pressure and the residue was purified by silica gel column chromatography (heptane:ethyl acetate=1:1) to obtain the title compound (830 mg, 58%) as a pale yellow solid.

$^1$H-NMR spectrum (CDCl$_3$) δ (ppm): 5.07 (2H, s), 6.94 (1H, d, J=9.0 Hz), 7.08 (1H, d, J=2.9 Hz), 7.22 (1H, dd, J=3.1 Hz, 9.0 Hz), 7.33-7.44 (5H, m), 9.84 (1H, s), 10.67 (1H, s).

Production Example 7-1-3

5-Benzyloxy-benzofuran-2-carboxylic acid ethyl ester

To a N,N-dimethylformamide (10 mL) solution of 5-benzyloxy-2-hydroxy-benzaldehyde (830 mg, 3.64 mmol) described in Production Example 7-1-2 were added bromoethyl acetate (446 µL, 4.00 mmol) and potassium carbonate (1.01 g, 7.28 mmol) at room temperature, which was stirred at 120° C. for 8 hours. Water was added to the reaction solution at 0° C. followed by extraction with ethyl acetate. The organic layer was washed with water and sat. NaCl followed by drying over anhydrous magnesium sulfate and filtering. The filtrate was concentrated under a reduced pressure and the residue was purified by NH silica gel column chromatography (heptane:ethyl acetate=2:1) to obtain the title compound (890 mg, 83%) as a pale yellow oil.

$^1$H-NMR spectrum (DMSO-d$_6$) δ (ppm): 1.33 (3H, t, J=7.1 Hz), 4.35 (2H, q, J=7.1 Hz), 5.15 (2H, s), 7.21 (1H, dd, J=2.6 Hz, 9.0 Hz), 7.32-7.42 (4H, m), 7.48 (2H, d, J=7.0 Hz), 7.66 (1H, d, J=9.3 Hz), 7.68 (1H, s).

Production Example 7-1-4

(5-Benzyloxy-benzofuran-2-yl)-methanol

To a tetrahydrofuran (20 mL) solution of 5-benzyloxy-benzofuran-2-carboxylic acid ethyl ester (890 mg, 3.00 mmol) described in Production Example 7-1-3 was added lithium aluminum hydride (342 mg, 9.00 mmol) at 0° C., which was stirred at room temperature for 3 hours. To the reaction solution were added water (342 µL), 5 N aqueous sodium hydroxide solution (342 µL) and water (1.03 mL) at 0° C. followed by filtering through Celite. The filtrate was concentrated under a reduced pressure and the residue was purified by silica gel column chromatography (heptane:ethyl acetate=3:1) to obtain the title compound (561 mg, 74%) as a white solid.

$^1$H-NMR spectrum (DMSO-d$_6$) δ (ppm): 4.53 (2H, d, J=5.5 Hz), 5.11 (2H, s), 5.44 (1H, t, J=5.7 Hz), 6.67 (1H, s), 6.93 (1H, dd, J=2.4 Hz, 8.8 Hz), 7.20 (1H, d, J=2.2 Hz), 7.33 (1H, t, J=7.1 Hz), 7.38-7.47 (5H, m).

Production Example 7-1-5

2-(5-Benzyloxy-benzofuran-2-ylmethyl)-isoindole-1,3-dione

To a tetrahydrofuran (10 mL) solution of (5-benzyloxy-benzofuran-2-yl)-methanol (561 mg, 2.21 mmol) described in Production Example 7-1-4 were added phthalimide (358 mg, 2.43 mmol), triphenylphosphine (696 mg, 2.65 mmol) and diethylazodicarboxylate (1.21 mL, 2.65 mmol) at 0° C., which was stirred at room temperature for 9 hours. Water was added to the reaction solution at room temperature followed by extraction with ethyl acetate. The organic layer was washed with sat. NaCl followed by drying over anhydrous magnesium sulfate and filtering. The filtrate was concentrated under a reduced pressure and the residue was purified by NH silica gel column chromatography (heptane:ethyl acetate=7:3) to obtain the title compound (635 mg, 75%) as a white solid.

$^1$H-NMR spectrum (DMSO-d$_6$) δ (ppm): 4.92 (2H, s), 5.10 (2H, s), 6.81 (1H, s), 6.93 (1H, dd, J=2.4 Hz, 9.0 Hz), 7.17 (1H, d, J=2.4 Hz), 7.31 (1H, t, J=7.0 Hz), 7.36-7.46 (5H, m), 7.83-7.94 (4H, m).

Production Example 7-1-6

C-(5-Benzyloxy-benzofuran-2-yl)-methylamine

To a mixed solution of 2-(5-benzyloxy-benzofuran-2-ylmethyl)-indole-1,3-dione (635 mg, 1.66 mmol) described in Production Example 7-1-5 in ethanol (6 mL) and tetrahydrofuran (6 mL) was added hydrazine hydrate (805 µL, 16.6 mmol) at room temperature, which was stirred for 1 hour while refluxing and heating. Water was added to the reaction solution at room temperature followed by extraction with ethyl acetate. The organic layer was washed with sat. NaCl followed by drying over anhydrous magnesium sulfate and filtering. The filtrate was concentrated under a reduced pressure and the residue was purified by NH silica gel column chromatography (ethyl acetate) to obtain the title compound (337 mg, 80%) as a white solid.

$^1$H-NMR spectrum (DMSO-d$_6$) δ (ppm): 3.78 (2H, s), 5.11 (2H, s), 6.60 (1H, s), 6.89 (1H, dd, J=2.6 Hz, 8.6 Hz), 7.17 (1H, d, J=2.6 Hz), 7.33 (1H, t, J=7.0 Hz), 7.38-7.41 (3H, m), 7.46 (2H, d, J=8.1 Hz).

Example 8

2,6-Diamino-N-(6-but-2-ynyloxy-benzofuran-2-ylmethyl)-nicotinamide

The title compound was obtained from C-(6-but-2-ynyloxy-benzofuran-2-yl)-methylamine described in Production Example 8-1-3 according the same method as Example 1.

$^1$H-NMR spectrum (DMSO-d$_6$) δ (ppm): 1.81 (3H, s), 4.46 (2H, d, J=5.6 Hz), 4.74 (2H, d, J=1.8 Hz), 5.65 (1H, d, J=8.4 Hz), 6.09 (2H, brs), 6.58 (1H, s), 6.83 (1H, dd, J=1.5 Hz, 8.6 Hz), 6.95 (2H, brs), 7.16 (1H, s), 7.42 (1H, d, J=8.4 Hz), 7.66 (1H, d, J=8.6 Hz), 8.33 (1H, t, J=5.7 Hz).

The starting material in the form C-(6-but-2-ynyloxy-benzofuran-2-yl)-methylamine was synthesized according to the method described below.

Production Example 8-1-1

6-But-2-ynyloxy-benzofuran-2-carboxlic acid ethyl ester

To a mixed solution of 6-hydroxy-benzofuran-2-carboxylic acid ethyl ester (250 mg, 1.21 mmol) in tetrahydrofuran (5 mL) and N,N-dimethylformamide (5 mL) were added sodium hydride (58 mg, 2.42 mmol) and 1-bromo-2-butyne (127 µL) at room temperature, which was stirred at room temperature for 1 hour. Water was added to the reaction solution followed by extraction with ethyl acetate. The organic layer was washed with water and sat. NaCl followed by drying over anhydrous magnesium sulfate and filtering. The filtrate was concentrated under a reduced pressure and the residue was purified by silica gel column chromatography (heptane:ethyl acetate=5:1) to obtain the title compound (254 mg, 81%) as a white solid.

$^1$H-NMR spectrum (CDCl$_3$) δ (ppm): 1.42 (3H, t, J=7.2 Hz), 1.87 (3H, s), 4.43 (2H, q, J=7.2 Hz), 4.70 (2H, s), 6.97 (1H, dd, J=1.6 Hz, 8.4 Hz), 7.20 (1H, s), 7.46 (1H, s), 7.53 (1H, d, J=8.4 Hz).

Production Example 8-1-2

(6-But-2-ynyloxy-benzofuran-2-yl)-methanol

The title compound (198 mg, 93%) was obtained as a white solid from 6-but-2-ynyloxy-benzofuran-2-carboxylic acid ethyl ester (254 mg, 983 μmol) described in Production Example 8-1-1 according to the same method as Production Example 7-1-4.

$^1$H-NMR spectrum (CDCl$_3$) δ (ppm): 1.85 (1H, t, J=6.2 Hz), 1.87 (3H, t, J=2.2 Hz), 4.69 (2H, q, J=2.2 Hz), 4.74 (2H, d, J=6.2 Hz), 6.60 (1H, s), 6.91 (1H, dd, J=2.4 Hz, 8.6 Hz), 7.11 (1H, d, J=1.8 Hz), 7.42 (1H, d, J=8.6 Hz)

Production Example 8-1-3

C-(6-But-2-ynyloxy-benzofuran-2-yl)-methylamine 2-(6-But-2-ynyloxy-benzofuran-2-ylmethyl)-isoindole-1,3-dione was obtained as a crude product (214 mg) from (6-but-2-ynyloxy-benzofuran-2-yl)-methanol (198 mg, 916 μmol) described in Production Example 8-1-2 according to the same method as Production Example 7-1-5. Then, the title compound (120 mg) was obtained as a pale yellow oil from the crude 2-(6-but-2-ynyloxy-benzofuran-2-ylmethyl)-isoindole-1,3-dione (214 mg) according to the same method as Production Example 7-1-6.

Example 9

N-(6-Allyloxy-benzofuran-2-ylmethyl)-2,6-diamino-nicotinamide

The title compound was obtained from a sodium salt of 2,6-diamino-N-(6-hydroxy-benzofuran-2-ylmethyl)-nicotinamide according to the same method as Example 3.

MS m/e (ESI): 339.25 (MH$^+$)

$^1$H-NMR spectrum (DMSO-d$_6$) δ (ppm): 4.45 (2H, d, J=5.5 Hz), 4.56 (2H, d, J=5.1 Hz), 5.24 (1H, d, J=10.6 Hz), 5.39 (1H, dd, J=1.8 Hz, 17.4 Hz), 5.65 (1H, d, J=8.6 Hz), 5.98-6.07 (1H, m), 6.09 (2H, brs), 6.56 (1H, s), 6.83 (1H, dd, J=2.4 Hz, 8.6 Hz), 6.95 (2H, brs), 7.13 (1H, d, J=1.8 Hz), 7.40 (1H, d, J=8.6 Hz), 7.65 (1H, d, J=8.6 Hz), 8.32 (1H, t, J=5.6 Hz).

The title compounds of Examples 10 to 23 were obtained according to the same method as Example 2.

Example 10

2,6-Diamino-N-(6-propoxy-benzofuran-2-ylmethyl)-nicotinamide

MS m/e (ESI): 341.19 (MH$^+$)

Example 11

2,6-Diamino-N-(6-butoxy-benzofuran-2-ylmethyl)-nicotinamide

MS m/e (ESI): 355.23 (MH$^+$)

Example 12

2,6-Diamino-N-(6-pentyloxy-benzofuran-2-ylmethyl)-nicotinamide

MS m/e (ESI): 369.27 (MH$^+$)

Example 13

2,6-Diamino-N-(6-isobutoxy-benzofuran-2-ylmethyl)-nicotinamide

MS m/e (ESI): 355.28 (MH$^+$)

Example 14

2,6-Diamino-N-(6-(3-methyl-butoxy)-benzofuran-2-ylmethyl)-nicotinamide

MS m/e (ESI): 369.31 (MH$^+$)

Example 15

2,6-Diamino-N-(6-(2-methyl-butoxy)-benzofuran-2-ylmethyl)-Nicotinamide

MS m/e (ESI): 369.33 (MH$^+$)

Example 16

2,6-Diamino-N-(6-(2,2-dimethyl-propoxy)-benzofuran-2-ylmethyl)-nicotinamide

MS m/e (ESI): 369.33 (MH$^+$)

Example 17

2,6-Diamino-N-(6-(3-methyl-but-2-enyloxy)-benzofuran-2-ylmethyl)-nicotinamide

MS m/e (ESI): 367.31 (MH$^+$)

Example 18

2,6-Diamino-N-(6-but-2-enyloxy-benzofuran-2-ylmethyl)-nicotinamide

MS m/e (ESI): 353.31 (MH$^+$)

Example 19

2,6-Diamino-N-(6-prop-2-ynyloxy-benzofuran-2-ylmethyl)-nicotinamide

MS m/e (ESI): 337.28 (MH$^+$)

Example 20

2,6-Diamino-N-(6-(2-fluoro-benzyloxy)-benzofuran-2-ylmethyl)-nicotinamide

MS m/e (ESI): 407.16 (MH$^+$)

Example 21

2,6-Diamino-N-(6-(4-fluoro-benzyloxy)-benzofuran-2-ylmethyl)-nicotinamide

MS m/e (ESI): 407.23 (MH$^+$)

Example 22

2,6-Diamino-N-(6-(3-fluoro-benzyloxy)-benzofuran-2-ylmethyl)-nicotinamide

MS m/e (ESI): 407.20 (MH$^+$)

Example 23

2,6-Diamino-N-(6-(2-fluoro-benzyloxy)-benzofuran-2-ylmethyl)-nicotinamide

MS m/e (ESI): 423.24 (MH$^+$)

The title compounds of Examples 24 to 35 were obtained by synthesizing according to the same reaction as Example 6 and purified by reverse phase high-performance liquid chromatography (using an acetonitrile-aqueous mobile phase (containing 0.1% trifluoroacetic acid)).

Example 24

2-Amino-N-(6-methoxy-benzofuran-2-ylmethyl)-6-methoxymethyl-nicotinamide

MS m/e (ESI): 342.36 (MH$^+$)

Example 25

2-Amino-N-(6-butoxy-benzofuran-2-ylmethyl)-6-methoxymethyl-nicotinamide

MS m/e (ESI): 384.40 (MH$^+$)

Example 26

2-Amino-6-methoxymethyl-N-(6-benzyloxy-benzofuran-2-ylmethyl)-nicotinamide

MS m/e (ESI): 398.42 (MH$^+$)

Example 27

2-Amino-N-(6-isobutoxy-benzofuran-2-ylmethyl)-6-methoxymethyl-nicotinamide

MS m/e (ESI): 384.15 (MH$^+$)

Example 28

2-Amino-6-methoxymethyl-N-(6-(3-methyl-butoxy)-benzofuran-2-ylmethyl)-nicotinamide MS m/e (ESI): 398.34 (MH$^+$)

Example 29

2-Amino-6-methoxymethyl-N-(6-(2-methyl-butoxy)-benzofuran-2-ylmethyl)-nicotinamide MS m/e (ESI): 398.43 (MH$^+$)

Example 30

2-Amino-N-(6-(2,2-dimethyl-propoxy)-benzofuran-2-ylmethyl)-nicotinamide

MS m/e (ESI): 398.43 (MH$^+$)

Example 31

2-Amino-6-methoxymethyl-N-(6-(3-methyl-but-2-enyloxy)-benzofuran-2-ylmethyl)-nicotinamide MS m/e (ESI): 396.40 (MH$^+$)

Example 32

2-Amino-N-(6-but-2-ynyloxy-benzofuran-2-ylmethyl)-6-methoxymethyl-nicotinamide

MS m/e (ESI): 380.24 (MH$^+$)

Example 33

2-Amino-6-methoxymethyl-N-(6-(tetrahydro-pyran-2-ylmethoxy)-benzofuran-2-ylmethyl)-nicotinamide MS m/e (ESI): 426.28 (MH$^+$)

Example 34

2-Amino-N-(6-(4-fluoro-benzyloxy)-benzofuran-2-ylmethyl)-6-methoxymethyl-nicotinamide MS m/e (ESI): 436.26 (MH$^+$)

Example 35

2-Amino-N-(6-(2-chloro-benzyloxy)-benzofuran-2-ylmethyl)-6-methoxymethyl-nicotinamide MS m/e (ESI): 452.23 (MH$^+$)

The title compounds of Examples 36 to 43 were obtained according to the same method as Example 6.

Example 36

2-Amino-N-(6-ethoxy-benzofuran-2-ylmethyl)-6-methoxymethyl-nicotinamide

MS m/e (ESI): 356.37 (MH$^+$)

$^1$H-NMR spectrum (CDCl$_3$) δ (ppm): 1.44 (3H, t, J=7.0 Hz), 3.45 (3H, s), 4.05 (2H, q, J=7.0 Hz), 4.39 (2H, s), 4.69 (2H, d, J=5.5 Hz), 6.41 (2H, brs), 6.47 (1H, t, J=4.8 Hz), 6.58 (1H, s), 6.70 (1H, dd, J=0.37 Hz, 7.9 Hz), 6.85 (1H, dd, J=2.2 Hz, 8.4 Hz), 6.97 (1H, s), 7.37 (1H, d, J=8.6 Hz), 7.64 (1H, d, J=7.9 Hz).

Example 37

2-Amino-6-methoxymethyl-N-(6-propoxy-benzofuran-2-ylmethyl)-nicotinamide

MS m/e (ESI): 370.39 (MH$^+$)

$^1$H-NMR spectrum (CDCl$_3$) δ (ppm): 1.05 (3H, t, J=7.3 Hz), 1.83 (2H, dt, J=6.8 Hz, 7.3 Hz), 3.45 (3H, s), 3.94 (2H, t, J=6.6 Hz), 4.39 (2H, s), 4.69 (2H, d, J=5.5 Hz), 6.40 (2H, brs), 6.46 (1H, t, J=5.3 Hz), 6.58 (1H, s), 6.69 (1H, d, J=7.9 Hz), 6.85 (1H, dd, J=2.2 Hz, 8.6 Hz), 6.97 (1H, d, J=2.0 Hz), 7.37 (1H, d, J=8.4 Hz), 7.64 (1H, d, J=7.9 Hz).

Example 38

2-Amino-N-(6-but-2-enyloxy-benzofuran-2-ylmethyl)-6-methoxymethyl-nicotinamide

MS m/e (ESI): 382.39 (MH$^+$)

$^1$H-NMR spectrum (CDCl$_3$) δ (ppm): 1.76 (3H, t, J=6.2 Hz), 3.45 (3H, s), 4.39 (2H, s), 4.48 (2H, dt, J=1.1 Hz, 6.0 Hz), 4.69 (2H, d, J=5.7 Hz), 5.69-5.80 (1H, m), 5.84-5.93 (1H, m), 6.40 (2H, brs), 6.47 (1H, t, J=5.3 Hz), 6.58 (1H, s), 6.69 (1H, d, J=7.9 Hz), 6.87 (1H, ddd, J=2.0 Hz, 3.8 Hz, 8.6 Hz), 6.99 (1H, dd, J=2.0 Hz, 4.2 Hz), 7.37 (1H, dd, J=3.1 Hz, 8.4 Hz), 7.63 (1H, d, J=7.9 Hz).

Example 39

2-Amino-6-methoxymethyl-N-(6-prop-2-ynyloxy-benzofuran-2-ylmethyl)-nicotinamide

MS m/e (ESI): 366.37 (MH$^+$)
$^1$H-NMR spectrum (CDCl$_3$) δ (ppm): 2.54 (1H, t, J=2.4 Hz), 3.45 (3H, s), 4.39 (2H, s), 4.70 (2H, d, J=5.5 Hz), 4.72 (2H, d, J=2.2 Hz), 6.41 (2H, brs), 6.47 (1H, t, J=5.1 Hz), 6.60 (1H, s), 6.70 (1H, d, J=7.9 Hz), 6.92 (1H, dd, J=2.2 Hz, 8.4 Hz), 7.10 (1H, d, J=1.8 Hz), 7.41 (1H, d, J=8.6 Hz), 7.64 (1H, d, J=7.9 Hz).

Example 40

2-Amino-N-(6-(2-methoxy-ethoxy)-benzofuran-2-ylmethyl)-6-methoxymethyl-nicotinamide MS m/e (ESI): 386.24 (MH$^+$)
$^1$H-NMR spectrum (CDCl$_3$) δ (ppm): 3.44 (3H, s), 3.47 (3H, s), 3.78 (2H, t, J=4.8 Hz), 4.15 (2H, t, J=4.8 Hz), 4.39 (2H, s), 4.70 (2H, d, J=5.5 Hz), 6.40 (2H, brs), 6.44 (1H, brs), 6.60 (1H, s), 6.71 (1H, d, J=7.9 Hz), 6.90 (1H, dd, J=2.2 Hz, 7.9 Hz), 7.01 (1H, s), 7.38 (1H, d, J=8.6 Hz), 7.65 (1H, d, J=7.9 Hz).

Example 41

2-Amino-N-(6-(2-ethoxy-ethoxy)-benzofuran-2-ylmethyl)-6-methoxymethyl-nicotinamide MS m/e (ESI): 400.27 (MH$^+$)
$^1$H-NMR spectrum (DMSO-d$_6$) δ (ppm): 1.11 (3H, t, J=7.0 Hz), 3.32 (3H, s), 3.48 (2H, q, J=7.0 Hz), 3.68 (2H, t, J=4.8 Hz), 4.08 (2H, t, J=4.8 Hz), 4.27 (2H, s), 4.52 (2H, d, J=4.2 Hz), 6.59 (1H, d, J=7.9 Hz), 6.63 (1H, s), 6.83 (1H, dd, J=2.2 Hz, 8.4 Hz), 7.10-7.16 (3H, m), 7.41 (1H, d, J=8.4 Hz), 7.97 (1H, d, J=8.1 Hz), 8.96 (1H, t, J=5.1 Hz).

Example 42

2-Amino-N-(6-(2-fluoro-benzyloxy)-benzofuran-2-ylmethyl)-6-methoxymethyl-nicotinamide MS m/e (ESI): 436.26 (MH$^+$)
$^1$H-NMR spectrum (CDCl$_3$) δ (ppm): 3.45 (3H, s), 4.39 (2H, s), 4.69 (2H, d, J=5.5 Hz), 5.16 (2H, s), 6.41 (2H, brs), 6.47 (1H, t, J=5.3 Hz), 6.59 (1H, s), 6.69 (1H, d, J=7.9 Hz), 6.94 (1H, dd, J=2.2 Hz, 8.6 Hz), 7.07 (1H, d, J=2.2 Hz), 7.07-7.12 (1H, m), 7.16 (1H, dt, J=0.92 Hz, 7.5 Hz), 7.29-7.34 (1H, m), 7.39 (1H, d, J=8.6 Hz), 7.52 (1H, dt, J=1.7 Hz, 7.5 Hz), 7.64 (1H, d, J=8.1 Hz).

Example 43

2-Amino-N-(6-(3-fluoro-benzyloxy)-benzofuran-2-ylmethyl)-6-methoxymethyl-nicotinamide MS m/e (ESI): 436.26 (MH$^+$)
$^1$H-NMR spectrum (DMSO-d$_6$) δ (ppm): 3.32 (3H, s), 4.27 (2H, s), 4.52 (2H, d, J=4.8 Hz), 5.14 (2H, s), 6.59 (1H, d, J=8.1 Hz), 6.64 (1H, s), 6.91 (1H, dd, J=2.2 Hz, 8.4 Hz), 7.13 (3H, brs), 7.22 (1H, s), 7.26-7.29 (2H, m), 7.39-7.44 (2H, m), 7.97 (1H, d, J=8.1 Hz), 8.96 (1H, brs).

Example 44

2-Amino-6-methoxymethyl-N-(6-(pyridin-2-ylmethoxy)-benzofuran-2-ylmethyl)-nicotinamide To a tetrahydrofuran (2 mL) solution of 2-amino-N-(6-hydroxy-benzofuran-2-ylmethyl)-6-methoxymethyl-nicotinamide (20 mg, 61 µmol) described in Production Example 5-1 were added 2-(hydroxymethyl)pyridine (6.5 µL, 67 µmol), triphenylphosphine (19.2 mg, 73 µmol) and diethylazodicarboxylate (33 µL, 73 µmol) at room temperature, which was stirred at room temperature for 30 minutes. After filtering the reaction solution, the filtrate was purified by reverse phase high-performance liquid chromatography (using an acetonitrile-aqueous mobile phase (containing 0.1% trifluoroacetic acid)) to obtain a mixture of the title compound and 2-amino-N-(6-hydroxy-benzofuran-2-ylmethyl)-6-methoxymethyl-nicotinamide. Then, this mixture was purified by silica gel column chromatography (ethyl acetate:methanol=10:1) to obtain the title compound (6 mg, 24%) as a white solid.

MS m/e (ESI): 419.26 (MH$^+$)
$^1$H-NMR spectrum (CDCl$_3$) δ (ppm): 3.45 (3H, s) 4.39 (2H, s), 4.69 (2H, d, J=5.5 Hz), 5.24 (2H, s), 6.40 (2H, brs), 6.44 (1H, brs), 6.60 (1H, s), 6.71 (1H, d, J=8.1 Hz), 6.96 (1H, dd, J=2.2 Hz, 8.6 Hz), 7.06 (1H, d, J=2.2 Hz), 7.24 (1H, ddd, J=1.1 Hz, 4.9 Hz, 7.5 Hz), 7.40 (1H, d, J=8.4 Hz), 7.54 (1H, d, J=7.9 Hz), 7.64 (1H, d, J=7.9 Hz), 7.72 (1H, ddd, J=1.8 Hz, 5.9 Hz, 7.7 Hz), 8.61 (1H, d, J=4.2 Hz).

Example 45

2-Amino-6-methoxymethyl-N-(6-(pyridin-3-ylmethoxy)-benzofuran-2-ylmethyl)-nicotinamide The title compound was obtained according to the same method as Example 44.

MS m/e (ESI): 419.36 (MH$^+$)
$^1$H-NMR spectrum (CDCl$_3$) δ (ppm): 3.45 (3H, s), 4.39 (2H, s), 4.70 (2H, d, J=5.5 Hz), 5.10 (2H, s), 6.41 (2H, brs), 6.52 (1H, brs), 6.61 (1H, s) 6.71 (1H, d, J=7.9 Hz), 6.93 (1H, dd, J=2.2 Hz, 8.6 Hz), 7.05 (1H, s), 7.33 (1H, dd, J=4.9 Hz, 7.9 Hz), 7.41 (1H, d, J=8.4 Hz), 7.66 (1H, d, J=7.9 Hz), 7.80 (1H, d, J=7.9 Hz), 8.59 (1H, d, J=4.0 Hz), 8.69 (1H, s).

Example 46

2-Amino-6-methoxymethyl-N-(6-(pyridin-4-ylmethoxy)-benzofuran-2-ylmethyl)-nicotinamide The title compound was obtained according to the same method as Example 44.

MS m/e (ESI): 419.39 (MH$^+$)
$^1$H-NMR spectrum (CDCl$_3$) δ (ppm): 3.46 (3H, s), 4.39 (2H, s), 4.70 (2H, d, J=5.7 Hz), 5.13 (2H, s), 6.41 (2H, brs), 6.43 (1H, brs), 6.61 (1H, s), 6.71 (1H, d, J=7.9 Hz), 6.93 (1H, dd, J=2.2 Hz, 8.4 Hz), 7.01 (1H, d, J=2.2 Hz), 7.37 (2H, d, J=6.0 Hz), 7.42 (1H, d, J=8.6 Hz), 7.64 (1H, d, J=7.9 Hz), 8.62 (2H, dd, J=1.7 Hz, 4.6 Hz)

Example 47

2-Amino-6-methoxymethyl-N-(6-methoxymethyl-benzofuran-2-ylmethyl)-nicotinamide

To a 1-methyl-2-pyrrolidinone (500 μL) solution of trifluoromethanesulfonic acid 2-(((2-amino-6-methoxymethyl-pyridin-3-carbonyl)-amino)-methyl)-benzofuran-6-yl ester (15 mg, 33 μmol) described in Production Example 47-1 were added tributyl-methoxymethyl-stannane (14 mg, 43 μmol), tetrakis(triphenylphosphine)palladium (0) (3.78 mg, 3.3 μmol) and tetrabutyl ammonium chloride (1.82 mg, 6.5 μmol) at room temperature, which was stirred at 135° C. for 4 hours under nitrogen atmosphere. After allowing the reaction solution to cool to room temperature, the reaction solution was filtered and purified by reverse phase high-performance liquid chromatography (using an acetonitrile-aqueous mobile phase (containing 0.1% trifluoroacetic acid)) followed by further purifying by silica gel column chromatography (ethyl acetate) to obtain the title compound (0.7 mg, 6%) as a white solid.

MS m/e (ESI): 356.23 (MH$^+$)

$^1$H-NMR spectrum (CDCl$_3$) δ (ppm): 3.40 (3H, s), 3.46 (3H, s), 4.40 (2H, s), 4.56 (2H, s), 4.74 (2H, d, J=5.5 Hz), 6.42 (3H, brs), 6.66 (1H, s), 6.72 (1H, d, J=7.9 Hz), 7.20 (1H, dd, J=1.3 Hz, 7.9 Hz), 7.45 (1H, s), 7.50 (1H, d, J=8.1 Hz), 7.65 (1H, d, J=8.1 Hz).

The starting material in the form of trifluoromethanesulfonic acid 2-(((2-amino-6-methoxymethyl-pyridin-3-carbonyl)-amino)-methyl)-benzofuran-6-yl ester was synthesized according to the method described below.

Production Example 47-1

Trifluoromethanesulfonic acid 2-(((2-amino-6-methoxymethyl-pyridin-3-carbonyl)-amino)-methyl)-benzofuran-6-yl ester

To a tetrahydrofuran solution of 2-amino-N-(6-hydroxy-benzofuran-2-ylmethyl)-6-methoxymethyl-nicotinamide (331 mg, 1.01 mmol) described in Production Example 5-1 was added 5 N aqueous sodium hydroxide solution (202 μL, 1.01 mmol), followed by concentrating the reaction solution under a reduced pressure to obtain a sodium salt (416 mg). To a mixed solution of the sodium salt (100 mg, 286 μmol) in methylene chloride (2 mL) and N,N-dimethylformamide (1 mL) were added triethylamine (79 μL, 572 μmol) and N-phenyltrifluoromethanesulfonimide (153 mg, 429 μmol) at room temperature, which was stirred for 15 hours. Water was added to the reaction solution followed by extraction with ethyl acetate. The organic phase was washed with sat. NaCl followed by drying over anhydrous magnesium sulfate and filtering. The residue was concentrated under a reduced pressure and the residue was purified by NH silica gel column chromatography (heptane:ethyl acetate=1:1) to obtain the title compound (101 mg, 77%) as a white solid.

$^1$H-NMR spectrum (DMSO-d$_6$) δ (ppm): 3.35 (3H, s), 4.30 (2H, s), 4.62 (2H, d, J=5.1 Hz), 6.63 (1H, d, J=7.9 Hz), 6.89 (1H, s), 7.16 (2H, brs), 7.36 (1H, dd, J=2.2 Hz, 8.4 Hz), 7.75 (1H, d, J=8.6 Hz), 7.91 (1H, d, J=2.4 Hz), 8.01 (1H, d, J=8.1 Hz), 9.06 (1H, m).

Example 48

2-Amino-N-(6-benzyl-benzofuran-2-ylmethyl)-6-methoxymethyl-nicotinamide

To a tetrahydrofuran (1 mL) solution of trifluoromethanesulfonic acid (2-(((2-amino-6-methoxymethyl-pyridin-3-carbonyl)-amino)-methyl)-benzofuran-6-yl ester (5 mg, 11 μmol) described in Production Example 47-1 were added (1,1'-bis(diphenylphosphino)ferrocene)dichloro nickel (II) (1.49 mg, 2.2 μmol) and benzyl magnesium chloride (56 μL, 55 μmol) at room temperature, which was stirred at room temperature for 25 hours under nitrogen atmosphere. Water was added to the reaction solution followed by extraction with ethyl acetate. The organic layer was washed with sat. NaCl followed by drying over anhydrous magnesium sulfate and filtering. The filtrate was concentrated under a reduced pressure and the residue was purified by silica gel column chromatography (ethyl acetate) to obtain the title compound (0.5 mg, 11%) as a white solid.

$^1$H-NMR spectrum (CDCl$_3$) δ (ppm): 3.46 (3H, s), 4.08 (2H, s), 4.39 (2H, s), 4.71 (2H, d, J=5.5 Hz), 6.39 (3H, brs), 6.63 (1H, s), 6.72 (1H, d, J=7.9 Hz), 7.09 (1H, d, J=7.9 Hz), 7.19-7.21 (3H, m), 7.26-7.30 (3H, m), 7.44 (1H, d, J=7.9 Hz), 7.63 (1H, d, J=7.9 Hz).

Example 49

2-Amino-6-methoxymethyl-N-(6-phenoxy-benzofuran-2-ylmethyl)-nicotinamide

The title compound was obtained by synthesizing from C-(6-phenoxy-benzofuran-2-yl)-methylamine described in Production Example 49-1-4 and 2-amino-6-methoxymethyl nicotinic acid described in Production Example 4-1-5 in accordance with the same method as Example 7 followed by purifying by reverse phase high-performance liquid chromatography (using an acetonitrile-aqueous mobile phase (containing 0.1% trifluoroacetic acid)).

MS m/e (ESI): 403.89 (MH$^+$)

The starting material in the form of C-(6-phenoxy-benzofuran-2-yl)-methylamine was synthesized according to the method described below.

Production Example 49-1-1

6-Phenoxy-benzofuran-2-carboxylic acid ethyl ester

To a mixed solution of 6-hydroxy-benzofuran-2-carboxylic acid ethyl ester (200 mg, 967 μmol) in tetrahydrofuran (4 mL) and N,N-dimethylformamide (4 mL) were added diphenylindonium iodine (395 mg, 967 μmol) and potassium t-butoxide (109 mg, 967 μmol) at 0° C., which was stirred at room temperature for 40 minutes under nitrogen atmosphere. After further stirring for 3 hours at 60° C., water was added to the reaction solution at room temperature followed by extraction with ethyl acetate, washing the organic layer with sat. NaCl, drying over anhydrous magnesium sulfate and filtering. The filtrate was concentrated under a reduced pressure and the residue was purified by silica gel column chromatography (hexane:ethyl acetate=20:1) to obtain the title compound (189 mg, 69%) as a colorless oil.

$^1$H-NMR spectrum (DMSO-d$_6$) δ (ppm): 1.33 (3H, t, J=7.1 Hz), 4.35 (2H, q, J=7.1 Hz), 7.05-7.10 (3H, m), 7.19 (1H, dt, J=1.1 Hz, 7.7 Hz), 7.37 (1H, s), 7.43 (2H, dd, J=7.3 Hz, 7.9 Hz), 7.76 (1H, s), 7.80 (1H, d, J=8.2 Hz).

Production Example 49-1-2

(6-Phenoxy-benzofuran-2-yl)-methanol

To a tetrahydrofuran (5 mL) solution of 6-phenoxy-benzofuran-2-carboxylic acid ethyl ester (251 mg, 889 μmol)

described in Production Example 49-1-1 was added lithium aluminum hydride (135 mg, 3.56 mmol) at 0° C., which was stirred at room temperature for 2 hours. To the reaction solution were added water (135 μL), 5 N aqueous sodium hydroxide solution (135 μL) and water (405 μL) at 0° C., followed by filtering through celite. The filtrate was concentrated under a reduced pressure and the residue was purified by NH silica gel column chromatography (hexane:ethyl acetate=1:1) to obtain the title compound (177 mg, 83%) as a colorless oil.

$^1$H-NMR spectrum (CDCl$_3$) δ (ppm): 1.85 (1H, t, J=6.0 Hz), 4.75 (2H, d, J=6.0 Hz), 6.64 (1H, s), 6.97 (1H, dd, J=2.0 Hz, 8.4 Hz), 7.01 (2H, dd, J=1.1 Hz, 8.8 Hz), 7.08-7.13 (2H, m), 7.33 (2H, dd, J=7.5 Hz, 8.6 Hz), 7.48 (1H, d, J=8.4 Hz).

Production Example 49-1-3

2-(6-Phenoxy-benzofuran-2-ylmethyl)-isoindole-1,3-dione

To a tetrahydrofuran (4 mL) solution of (6-phenoxy-benzofuran-2-yl)-methanol (177 mg, 737 μmol) described in Production Example 49-1-2 were added phthalimide (119 mg, 811 μmol), triphenylphosphine (232 mg, 884 μmol) and diethylazodicarboxylate (403 μL, 884 mmol) at 0° C., which was stirred at room temperature for 4 hours and 30 minutes. Water was added to the reaction solution followed by extraction with ethyl acetate. The organic layer was washed with sat. NaCl followed by drying over anhydrous magnesium sulfate and filtering. The filtrate was concentrated under a reduced pressure and the residue was purified by NH silica gel column chromatography (hexane:ethyl acetate=5:1) to obtain the title compound (209 mg, 77%) as a colorless oil.

$^1$H-NMR spectrum (DMSO-d$_6$) δ (ppm): 4.94 (2H, s), 6.90 (1H, s), 6.94 (1H, dd, J=2.2 Hz, 8.4 Hz), 6.98 (2H, dd, J=1.1 Hz, 8.9 Hz), 7.11 (1H, dt, J=1.1 Hz, 7.5 Hz), 7.22 (1H, d, J=1.8 Hz), 7.36 (2H, dd, J=7.5 Hz, 8.6 Hz), 7.58 (1H, d, J=8.6 Hz), 7.86-7.94 (4H, m).

Production Example 49-1-4

C-(6-Phenoxy-benzofuran-2-yl)-methylamine

To an ethanol (5 mL) solution of 2-(6-phenoxy-benzofuran-2-ylmethyl)-isoindole-1,3-dione (209 mg, 566 μmol) described in Production Example 49-1-3 was added hydrazine hydrate (549 μL, 11.3 mmol) at room temperature, which was stirred for 1 hour while heating under reflux. Water was added to the reaction solution at room temperature followed by extraction with ethyl acetate. The organic layer was dried over anhydrous magnesium sulfate and filtered. The filtrate was concentrated under a reduced pressure and the residue was purified by silica gel column chromatography (ethyl acetate:methanol=10:1) to obtain the title compound (92 mg, 68%) as a colorless oil.

$^1$H-NMR spectrum (DMSO-d$_6$) δ (ppm): 3.80 (2H, s), 6.67 (1H, d, J=0.92 Hz), 6.92 (1H, dd, J=2.2 Hz, 8.4 Hz), 6.98 (2H, dd, J=1.1 Hz, 8.8 Hz), 7.11 (1H, dt, J=1.1 Hz, 7.5 Hz), 7.21 (1H, s), 7.37 (2H, dd, J=7.5 Hz, 8.4 Hz), 7.56 (1H, d, J=8.4 Hz).

Example 50

2,6-Diamino-N-(6-phenoxy-benzofuran-2-ylmethyl)-nicotinamide

The title compound was obtained from C-(6-phenoxy-benzofuran-2-yl)-methylamine described in Production Example 49-1-4 and 2,6-diaminonicotinic acid described in Production Example 1-1-4 in accordance with the same method as Example 1.

$^1$H-NMR spectrum (DMSO-d$_6$) δ (ppm): 4.50 (2H, d, J=5.7 Hz), 5.68 (1H, d, J=8.6 Hz), 6.12 (2H, brs), 6.69 (1H, s), 6.93 (1H, dd, J=2.0 Hz, J=8.4 Hz), 6.97 (2H, brs), 6.98 (2H, d, J=8.1 Hz), 7.11 (1H, t, J=7.5 Hz), 7.25 (1H, d, J=1.8 Hz), 7.37 (2H, t, J=8.2 Hz), 7.57 (1H, d, J=8.4 Hz), 7.68 (1H, d, J=8.6 Hz), 8.38 (1H, t, J=5.7 Hz).

Example 51

2,6-Diamino-N-(5-benzyloxy-benzofuran-2-ylmethyl)-nicotinamide

The title compound was obtained from C-(5-benzyloxy-benzofuran-2-yl)-methylamine described Production Example 7-1-6 and 2,6-diaminonicotinic acid described in Production Example 1-1-4 in accordance with the same method as Example 1.

$^1$H-NMR spectrum (DMSO-d$_6$) δ (ppm): 4.48 (2H, d, J=5.7 Hz), 5.10 (2H, s), 5.68 (1H, d, J=8.4 Hz), 6.11 (2H, s), 6.60 (1H, s), 6.91 (1H, dd, J=2.8 Hz, 9.0 Hz), 6.96 (2H, s), 7.17 (1H, d, J=2.4 Hz), 7.32 (1H, t, J=7.3 Hz), 7.37-7.41 (3H, m), 7.44 (2H, t, J=7.3 Hz), 7.68 (1H, d, J=8.6 Hz), 8.37 (1H, t, J=5.7 Hz).

Example 52

N-(5-Allyloxy-benzofuran-2-ylmethyl)-2,6-diamino-nicotinamide

The title compound was obtained from 2,6-diamino-N-(5-hydroxy-benzofuran-2-ylmethyl)-nicotinamide described in Production Example 52-1 and allyl bromide in accordance with the same method as Example 2.

MS m/e (ESI): 339.34 (MH$^+$)

The starting material in the form of 2,6-diamino-N-(5-hydroxy-benzofuran-2-ylmethyl)-nicotinamide was synthesized according to the method described below.

Production Example 52-1

2,6-Diamino-N-(5-hydroxy-benzofuran-2-ylmethyl)-nicotinamide

The title compound (136 mg, as equivalent) was obtained as a white powder from 2,6-diamino-N-(5-benzyloxy-benzofuran-2-ylmethyl)-nicotinamide (151 mg, 389 μmol) described in Example 51 in accordance with the same method as Production Example 2-1.

$^1$H-NMR spectrum (DMSO-d$_6$) δ (ppm): 4.45 (2H, s), 5.81 (1H, d, J=8.8 Hz), 6.53 (1H, s), 6.65 (1H, d, J=8.6 Hz), 6.84 (1H, s), 7.26 (1H, d, J=8.6 Hz), 7.89 (1H, d, J=8.1 Hz), 8.62 (1H, s), 9.08 (1H, s).

Example 53

2,6-Diamino-N-(5-cyclopropylmethoxy-benzofuran-2-ylmethyl)-nicotinamide

The title compound was obtained from 2,6-diamino-N-(5-hydroxy-benzofuran-2-ylmethyl)-nicotinamide described in Production Example 52-1 and cyclopropylmethyl bromide in accordance with the same method as Example 52.

MS m/e (ESI): 353.37 (MH$^+$)

Example 54

N-(5-Allyloxy-benzofuran-2-ylmethyl)-2-amino-6-methoxymethyl-nicotinamide

The title compound was obtained from 2-amino-N-(5-benzyloxy-benzofuran-2-ylmethyl)-6-methoxymethyl-nicotinamide described in Example 7 in accordance with the same method as Example 5.

$^1$H-NMR spectrum (CDCl$_3$) δ (ppm): 3.46 (3H, s), 4.40 (2H, s), 4.54 (2H, ddd, J=1.3 Hz, J=1.5 Hz, J=5.3 Hz), 4.71 (2H, d, J=5.7 Hz), 5.29 (1H, ddd, J=1.3 Hz, 1.5 Hz, 11.9 Hz), 5.43 (1H, ddd, J=1.3 Hz, 1.5 Hz, 17.2 Hz), 6.03-6.13 (1H, m), 6.39 (3H, brs), 6.61 (1H, s), 6.72 (1H, d, J=7.9 Hz), 6.91 (1H, dd, J=2.7 Hz, 8.8 Hz), 7.01 (1H, d, J=2.6 Hz), 7.33 (1H, d, J=9.0 Hz), 7.65 (1H, d, J=7.9 Hz).

Example 55

2-Amino-N-(5-cyclopropylmethoxy-benzofuran-2-ylmethyl)-6-methoxymethyl-nicotinamide The title compound was obtained from 2-amino-N-(5-benzyloxy-benzofuran-2-ylmethyl)-6-methoxymethyl-nicotinamide described in Example 7 in accordance with the same method as Example 54.

$^1$H-NMR spectrum (CDCl$_3$) δ (ppm): 0.36 (2H, dt, J=4.8 Hz, 5.9 Hz), 0.65 (2H, dt, J=4.8 Hz, 5.9 Hz), 1.26-1.31 (1H, m), 3.46 (3H, s), 3.82 (2H, d, J=7.0 Hz), 4.40 (2H, s), 4.71 (2H, d, J=5.7 Hz), 6.39 (3H, brs), 6.60 (1H, d, J=0.73 Hz), 6.72 (1H, d, J=7.9 Hz), 6.90 (1H, dd, J=2.6 Hz, 8.8 Hz), 6.98 (1H, d, J=2.6 Hz), 7.33 (1H, d, J=8.8 Hz), 7.65 (1H, d, J=8.1 Hz).

Example 56

2-Amino-6-methoxymethyl-N-(5-methoxymethyl-benzofuran-2-ylmethyl)-nicotinamide

The title compound was obtained from 2-amino-N-(5-bromo-benzofuran-2-ylmethyl)-6-methoxymethyl-nicotinamide described in Production Example 56-1-5 in accordance with the same method as Example 47.

MS m/e (ESI): 356.29 (MH$^+$)

$^1$H-NMR spectrum (CDCl$_3$) δ (ppm): 3.39 (3H, s), 3.46 (3H, s), 4.41 (2H, s), 4.53 (2H, s), 4.74 (2H, d, J=5.7 Hz), 6.44 (3H, brs), 6.61 (1H, s), 6.72 (1H, d, J=7.9 Hz), 7.25-7.26 (1H, m), 7.42 (1H, d, J=8.6 Hz), 7.51 (1H, s), 7.67 (1H, d, J=7.9 Hz).

The starting material in the form of 2-amino-N-(5-bromo-benzofuran-2-ylmethyl)-6-methoxymethyl-nicotinamide was synthesized according to the method described below.

Production Example 56-1-1

5-Bromo-benzofuran-2-carboxylic acid ethyl ester

The title compound (7.29 g, 77%) was obtained as a white solid from 5-bromosalicylaldehyde (7.05 g, 35.1 mmol) in accordance with the same method as Production Example 1-2-1.

$^1$H-NMR spectrum (DMSO-d$_6$) δ (ppm): 1.31 (3H, dt, J=1.8 Hz, 7.1 Hz), 4.35 (2H, dq, J=1.8 Hz, 7.1 Hz), 7.65 (1H, ddd, J=0.37 Hz, 1.7 Hz, 8.8 Hz), 7.70-7.73 (2H, m), 8.01 (1H, t, J=1.7 Hz).

Production Example 56-1-2

(5-Bromo-benzofuran-2-yl)-methanol

To a tetrahydrofuran (20 mL) solution of lithium aluminum hydride (706 mg, 18.6 mmol) was added aluminum chloride (2.98 g, 22.3 mmol), which was stirred until the aluminum chloride dissolved in tetrahydrofuran. Then, to the reaction mixture was added 5-bromo-benzofuran-2-carboxylic acid ethyl ester (1.00 g, 3.72 mmol) described in Production Example 56-1-1 at 0° C. followed by stirring at 0° C. for 20 minutes. To the reaction solution was added aqueous ammonium followed by filtering through Celite. The filtrate was concentrated under a reduced pressure and the residue was purified by silica gel column chromatography (heptane:ethyl acetate=2:1) to obtain the title compound (780 mg, 92%) as a white solid.

$^1$H-NMR spectrum (DMSO-d$_6$) δ (ppm): 4.57 (2H, d, J=5.6 Hz), 5.54 (1H, t, J=5.9 Hz), 6.75 (1H, s), 7.41 (1H, dd, J=2.0 Hz, 8.4 Hz), 7.53 (1H, d, J=8.6 Hz), 7.81 (1H, d, J=2.0 Hz).

Production Example 56-1-3

2-(5-Bromo-benzofuran-2-ylmethyl)-isoindole-1,3-dione

The title compound (1.24 g, as equivalent) was obtained as a white solid from (5-bromo-benzofuran-2-yl)-methanol (780 mg, 3.44 mmol) described in Production Example 56-1-2 in accordance with the same method as Production Example 1-2-3.

$^1$H-NMR spectrum (DMSO-d$_6$) δ (ppm): 4.97 (2H, s), 6.90 (1H, s), 7.41 (1H, ddd, J=2.4 Hz, 2.8 Hz, 8.8 Hz), 7.53 (1H, dd, J=1.2 Hz, 8.8 Hz), 7.80 (1H, t, J=2.2 Hz), 7.87-7.95 (4H, m).

Production Example 56-1-4

C-(5-Bromo-benzofuran-2-yl)-methylamine

The title compound (976 mg, as equivalent) was obtained as a pale yellow oily material from 2-(5-bromo-benzofuran-2-ylmethyl)-isoindole-1,3-dione (1.24 g, 3.48 mmol) described in Production Example 56-1-3 in accordance with the same method as Production Example 1-2-4.

$^1$H-NMR spectrum (DMSO-d$_6$) δ (ppm): 3.82 (2H, s), 6.68 (1H, s), 7.37 (1H, dd, J=2.2 Hz, 8.6 Hz), 7.49 (1H, d, J=8.6 Hz), 7.78 (1H, d, J=1.8 Hz).

Production Example 56-1-5

2-Amino-N-(5-bromo-benzofuran-2-ylmethyl)-6-methoxymethyl-nicotinamide

To an N,N-dimethylformamide (10 mL) solution of C(5-bromo-benzofuran-2-yl)-methylamine (455 mg, 2.01 mmol) described in Production Example 56-1-4 were added 2-amino-6-methoxymethyl-nicotinic acid (293 mg, 1.61 mmol) described in Production Example 4-1-5, triethylamine (700 mL, 5.03 μmol) and benzotriazol-1-yloxytris(dimethylamino)phosphonium hexafluorophosphate (1.07 g, 2.41 mmol) at room temperature, which was stirred for 12 hours. Water was added to the reaction solution at room temperature followed by extraction with ethyl acetate. The organic layer was washed with water and sat. NaCl followed by drying over anhydrous magnesium sulfate and filtering. The filtrate was concentrated under a reduced pressure and the residue was purified by NH silica gel column chromatography (heptane: ethyl acetate=1:1) to obtain the title compound (255 mg, 33%) as a white solid.

$^1$H-NMR spectrum (DMSO-$d_6$) δ (ppm): 3.35 (3H, s), 4.30 (2H, s), 4.60 (2H, d, J=5.1 Hz), 6.62 (1H, d, J=7.9 Hz), 6.75 (1H, s), 7.15 (2H, brs), 7.40 (1H, ddd, J=0.9 Hz, 1.1 Hz, 8.6 Hz), 7.54 (1H, d, J=8.6 Hz), 7.80 (1H, d, J=2.2 Hz), 8.00 (1H, d, J=8.1 Hz), 9.05 (1H, t, J=5.9 Hz).

Example 57

2-Amino-N-(5-butyl-benzofuran-2-ylmethyl)-6-methoxymethyl-nicotinamide

The title compound was obtained as a by-product of Example 56.

MS m/e (ESI): 368.32 (MH$^+$)

$^1$H-NMR spectrum (CDCl$_3$) δ (ppm): 0.924 (3H, t, J=7.2 Hz), 1.35 (2H, dt, J=7.2 Hz, 7.6 Hz), 1.57-1.65 (2H, m), 2.67 (2H, t, J=7.6 Hz), 3.45 (3H, s), 4.40 (2H, s), 4.72 (2H, d, J=5.7 Hz), 6.39 (3H, brs), 6.62 (1H, s), 6.71 (1H, dd, J=0.6 Hz, 7.9 Hz), 7.09 (1H, d, J=7.0 Hz), 7.32-7.35 (2H, m), 7.64 (1H, d, J=7.7 Hz).

Example 58

2-Amino-N-(6-benzyloxy-benzofuran-2-ylmethyl)-nicotinamide

The title compound was obtained from C-(6-benzyloxy-benzofuran-2-yl)-methylamine described in Production Example 1-2-4 and 2-aminonicotinic acid in accordance with the same method as Example 4.

$^1$H-NMR spectrum (DMSO-$d_6$) δ (ppm): 4.53 (2H, d, J=5.3 Hz), 5.11 (2H, s), 6.56 (1H, dd, J=7.7 Hz, 7.9 Hz), 6.64 (1H, s), 6.90 (1H, dd, J=2.2 Hz, 8.4 Hz), 7.07 (2H, s), 7.22 (1H, d, J=1.8 Hz), 7.30 (1H, t, J=7.5 Hz), 7.37 (2H, t, J=7.9 Hz), 7.42 (1H, d, J=8.4 Hz), 7.43-7.45 (2H, m), 7.93 (1H, dd, J=1.8 Hz, 8.0 Hz), 8.06 (1H, dd, J=1.7 Hz, 4.8 Hz), 8.98 (1H, t, J=5.3 Hz).

The title compounds of Examples 59 to 72 were obtained by synthesizing from 2-amino-N-(6-hydroxy-benzofuran-2-ylmethyl)-nicotinamide described in Production Example 59-1 in accordance with the same method as Example 5 and purifying by reverse phase high-performance liquid chromatography (using an acetonitrile-aqueous mobile phase (containing 0.1% trifluoroacetic acid)).

Example 59

2-Amino-N-(6-ethoxy-benzofuran-2-ylmethyl)-nicotinamide

MS m/e (ESI): 312.13 (MH$^+$)

The starting material in the form of 2-amino-N-(6-hydroxy-benzofuran-2-ylmethyl)-nicotinamide was synthesized according to the method described below.

Production Example 59-1

2-Amino-N-(6-hydroxy-benzofuran-2-ylmethyl)-nicotinamide

To a trifluoroacetic acid solvent of 2-amino-N-(6-benzyloxy-benzofuran-2-ylmethyl)-nicotinamide (323 mg, 865 mmol) described in Example 58 at 0° C., which was stirred at room temperature for 3 hours. Sodium bicarbonate and water were added to the reaction solution at 0° C. followed by extraction with ethyl acetate. The organic layer was washed with sat. NaCl followed by drying by adding anhydrous magnesium sulfate and filtering. The filtrate was concentrated under a reduced pressure and the resulting residue was purified by NH silica gel column chromatography (ethyl acetate: methanol=10:1) to obtain the title compound (219 mg, 89%) as a white solid.

$^1$H-NMR spectrum (DMSO-$d_6$) δ (ppm): 4.50 (2H, d, J=5.1 Hz), 6.55-6.58 (1H, m), 6.58 (1H, s), 6.68 (1H, d, J=8.2 Hz), 6.85 (1H, d, J=1.8 Hz), 7.07 (2H, brs, 7.30 (1H, d, J=8.2 Hz), 7.93 (1H, dd, J=1.5 Hz, 7.7 Hz), 8.06 (1H, d, J=6.0 Hz), 8.96 (1H, t, J=5.3 Hz), 9.44 (1H, brs).

Example 60

2-Amino-N-(6-propoxy-benzofuran-2-ylmethyl)-nicotinamide

MS m/e (ESI): 326.17 (MH$^+$)

Example 61

2-Amino-N-(6-butoxy-benzofuran-2-ylmethyl)-nicotinamide

MS m/e (ESI): 340.22 (MH$^+$)

Example 62

2-Amino-N-(6-pentyloxy-benzofuran-2-ylmethyl)-nicotinamide

MS m/e (ESI): 354.26 (MH$^+$)

Example 63

2-Amino-N-(6-isobutoxy-benzofuran-2-ylmethyl)-nicotinamide

MS m/e (ESI): 340.37 (MH$^+$)

Example 64

2-Amino-N-(6-(3-methyl-butoxy)-benzofuran-2-ylmethyl)-nicotinamide

MS m/e (ESI): 354.37 (MH$^+$)

Example 65

2-Amino-N-(6-(2-methyl-butoxy)-benzofuran-2-ylmethyl)-nicotinamide

MS m/e (ESI): 354.29 (MH$^+$)

Example 66

2-Amino-N-(6-(2,2-dimethyl-propoxy)-benzofuran-2-ylmethyl)-nicotinamide

MS m/e (ESI): 354.32 (MH$^+$)

Example 67

N-(6-Allyloxy-benzofuran-2-ylmethyl)-2-amino-nicotinamide

MS m/e (ESI): 324.33 (MH$^+$)

Example 68

2-Amino-N-(6-(3-methyl-but-2-enyloxy)-benzofuran-2-ylmethyl)-nicotinamide

MS m/e (ESI): 352.35 (MH$^+$)

Example 69

2-Amino-N-(6-but-2-enyloxy-benzofuran-2-ylmethyl)-nicotinamide

MS m/e (ESI): 338.28 (MH$^+$)

Example 70

2-Amino-N-(6-prop-2-ynyloxy-benzofuran-2-ylmethyl)-nicotinamide

MS m/e (ESI): 322.27 (MH$^+$)

Example 71

2-Amino-N-(6-but-2-ynyloxy-benzofuran-2-ylmethyl)-nicotinamide

MS m/e (ESI): 336.34 (MH$^+$)

Example 72

2-Amino-N-(6-cyclopropylmethoxy-benzofuran-2-ylmethyl)-nicotinamide

MS m/e (ESI): 338.34 (MH$^+$)

Example 73

2-Amino-N-(6-cyclopropylmethoxy-1H-indol-2-ylmethyl)-6-methoxymethyl-nicotinamide The title compound was obtained from C-(6-cyclopropylmethoxy-1H-indol-2-yl)-methylamine described in Production Example 73-1-5 and 2-amino-6-methoxymethylnicotinic acid described in Example 4-1-5 in accordance with the same method as Example 4.

$^1$H-NMR spectrum (DMSO-d$_6$) δ (ppm): 0.30-0.34 (2H, m), 0.54-0.58 (2H, m), 1.20-1.26 (1H, m), 3.34 (3H, s), 3.77 (2H, d, J=7.0 Hz), 4.29 (2H, s), 4.51 (2H, s), 6.18 (1H, s), 6.59-6.62 (2H, m), 6.83 (1H, d, J=2.2 Hz), 7.12 (2H, brs), 7.29 (1H, d, J=8.6 Hz), 7.98 (1H, d, J=7.9 Hz), 8.87 (1H, brs), 10.67 (1H, s).

The starting material in the form of C-(6-cyclopropylmethoxy-1H-indol-2-yl)-methylamine was synthesized according to the method described below.

Production Example 73-1-1

6-Hydroxy-1H-indole-2-carboxylic acid methyl ester

To a dichloromethane (10 mL) solution of 6-methoxy-1H-indole-2-carboxylic acid methyl ester (500 mg, 2.44 mmol) was added boron tribromide (12.2 mL, 12.2 mmol) at −78° C., which was stirred for 50 minutes at 0° C. under nitrogen atmosphere. To the reaction solution was added water at 0° C. followed by extraction with ethyl acetate. The organic layer was washed with sat. NaCl followed by drying over anhydrous magnesium sulfate and filtering. The filtrate was concentrated under a reduced pressure and the residue was purified by silica gel column chromatography (heptane:ethyl acetate=1:1) to obtain the title compound (395 mg, 85%) as a white solid.

$^1$H-NMR spectrum (CDCl$_3$) δ (ppm): 3.92 (3H, s), 4.97 (1H, s), 6.74 (1H, dd, J=2.2 Hz, 8.6 Hz), 6.82 (1H, s), 7.16 (1H, dd, J=1.1 Hz, 2.2 Hz), 7.54 (1H, d, J=8.8 Hz), 8.70 (1H, brs).

Production Example 73-1-2

6-Cyclopropylmethoxy-1H-indole-2-carboxylic acid methyl ester

To a tetrahydrofuran (8 mL) solution of 6-hydroxy-1H-indole-2-carboxylic acid methyl ester (395 mg, 2.07 mmol) described in Production Example 73-1-1 was added 5 N aqueous sodium hydroxide solution (414 μL, 2.07 mmol), which was concentrated under a reduced pressure. To an N,N-dimethylformamide (8 mL) solution of the residue was added cyclopropylmethyl bromide (241 μL, 2.48 mmol) at room temperature followed by stirring at room temperature for 12 hours. Moreover, after stirring at 50° C. for 4 hours, water was added to the reaction solution at room temperature followed by extraction with ethyl acetate. The organic layer was washed with water and sat. NaCl followed by drying over anhydrous magnesium sulfate and filtering. The filtrate was concentrated under a reduced pressure and the residue was purified by NH silica gel column chromatography (heptane:ethyl acetate=3:1) to obtain the title compound (297 mg, 59%) as a white solid.

$^1$H-NMR spectrum (CDCl$_3$) δ (ppm): 0.36-0.40 (2H, m), 0.64-0.69 (2H, m), 1.28-1.35 (1H, m), 3.84 (2H, d, J=7.0 Hz), 3.92 (3H, s), 6.81 (1H, d, J=2.2 Hz), 6.85 (1H, dd, J=2.2 Hz, 8.8 Hz), 7.15 (1H, dd, J=0.92 Hz, 2.0 Hz), 7.55 (1H, d, J=8.8 Hz), 8.70 (1H, brs).

Production Example 73-1-3

(6-Cyclopropylmethoxy-1H-indol-2-yl)-methanol

The title compound (197 mg, 75%) was obtained as a white solid from 6-cyclopropylmethoxy-1H-indole-2-carboxylic acid methyl ester (297 mg, 1.21 mmol) described in Production Example 73-1-2 in accordance with the same method as Production Example 1-2-2.

$^1$H-NMR spectrum (CDCl$_3$) δ (ppm): 0.35-0.38 (2H, m), 0.63-0.67 (2H, m), 1.29-1.33 (1H, m), 1.69 (1H, t, J=5.6 Hz), 3.83 (2H, d, J=6.8 Hz), 4.79 (2H, d, J=6.0 Hz), 6.33 (1H, dd, J=0.80 Hz, 2.4 Hz), 6.79 (1H, dd, J=2.4 Hz, 8.4 Hz), 6.84 (1H, d, J=2.0 Hz), 7.43 (1H, d, J=8.8 Hz), 8.18 (1H, brs).

Production Example 73-1-4

6-Cyclopropylmethoxy-1H-indole-2-carbaldehyde

To a dichloromethane (5 mL) solution of (6-cyclopropylmethoxy-1H-indol-2-yl)-methanol (197 mg, 907 μmol) described in Production Example 73-1-3 was added manganese dioxide (789 mg, 9.07 mmol) at room temperature, which was stirred at room temperature for 17 hours. The reaction solution was filtered followed by concentrating the filtrate under a reduced pressure. The residue was purified by silica gel column chromatography (heptane:ethyl acetate=1:1) to obtain the title compound (144 mg, 74%) as a pale brown solid.

¹H-NMR spectrum (CDCl₃) δ (ppm): 0.37-0.41 (2H, m), 0.65-0.70 (2H, m), 1.28-1.34 (1H, m), 3.86 (2H, d, J=6.8 Hz), 6.79 (1H, d, J=2.0 Hz), 6.87 (1H, dd, J=2.2 Hz, 8.8 Hz), 7.20 (1H, dd, J=0.92 Hz, 2.2 Hz), 7.60 (1H, d, J=8.8 Hz), 8.93 (1H, brs), 9.72 (1H, s).

Production Example 73-1-5

C-(6-cyclopropylmethoxy-1H-indol-2-yl)-methylamine

To an ammonia-methanol (5 mL) solution of 6-cyclopropylmethoxy-1H-indole-2-carbaldehyde (144 mg, 669 μmol) described in Production Example 73-1-4 was added Raney nickel, which was stirred at room temperature for 8 hours under hydrogen atmosphere. The reaction mixture was filtered through Celite and the filtrate was concentrated under a reduced pressure. The residue was purified by NH silica gel column chromatography (ethyl acetate:methanol=10:1) to obtain the title compound (91 mg, 63%) as a pale brown oil.

¹H-NMR spectrum (CDCl₃) δ (ppm): 0.34-0.38 (2H, m), 0.62-0.67 (2H, m), 1.26-1.32 (1H, m), 3.83 (2H, d, J=7.0 Hz), 4.02 (2H, s), 6.24 (1H, s), 6.77 (1H, dd, J=2.2 Hz, 8.6 Hz), 6.84 (1H, d, J=2.2 Hz), 7.40 (1H, d, J=8.6 Hz), 8.35 (1H, brs).

Example 74

2,6-Diamino-N-(6-cyclopropylmethoxy-1H-indol-2-ylmethyl)-nicotinamide

The title compound was obtained from C-(6-cyclopropylmethoxy-1H-indol-2-yl)-methylamine described in Production Example 73-1-5 and 2,6-diaminonicotinic acid described in Production Example 1-1-4 in accordance with the same method as Example 1.

¹H-NMR spectrum (DMSO-d₆) δ (ppm): 0.00-0.026 (2H, m), 0.22-0.27 (2H, m), 0.86-0.94 (1H, m), 3.46 (2H, d, J=6.8 Hz), 4.14 (2H, d, J=5.5 Hz), 5.36 (1H, d, J=8.6 Hz), 5.77 (2H, s), 5.82 (1H, s), 6.28 (1H, dd, J=2.4 Hz, 8.6 Hz), 6.53 (1H, d, J=2.4 Hz), 6.67 (2H, brs), 6.97 (1H, d, J=8.6 Hz), 7.36 (1H, d, J=8.6 Hz), 7.93 (1H, t, J=5.9 Hz), 10.25 (1H, s).

Example 75

2-Amino-6-methoxymethyl-N-(2-phenoxymethyl-benzofuran-5-ylmethyl)-nicotinamide

The title compound was obtained from C-(2-phenoxymethyl-benzofuran-5-yl)-methylamine described in Production Example 75-1-3 and 2-amino-6-methoxymethyl-nicotinic acid described in Production Example 4-1-5 in accordance with the same method as Example 4.

¹H-NMR spectrum (CDCl₃) δ (ppm): 3.45 (3H, s), 4.39 (2H, s), 4.76 (2H, d, J=5.2 Hz), 5.17 (2H, s), 6.03 (1H, brs), 6.42 (2H, brs), 6.68-6.70 (1H, m), 6.76-6.77 (1H, m), 6.98-7.04 (3H, m), 7.29-7.34 (3H, m), 7.46-7.49 (1H, m), 7.54 (1H, d, J=1.2 Hz), 7.60 (1H, d, J=8.0 Hz).

The starting material in the form of C-(2-phenoxymethyl-benzofuran-5-yl)-methylamine was synthesized according to the method described below.

Production Example 75-1-1

5-Iodo-2-phenoxymethyl-benzofuran

To a carbon tetrachloride (28 mL) solution of 5-iodo-2-methylbenzofuran (500 mg, 1.94 mmol) were added N-bromosuccinimide (410 mg, 2.3 mmol) and 2,2-azobis(isobutyronitrile) (47.8 mg, 0.291 mmol). This mixture was stirred for 2 hours and 45 minutes while heating under reflux. After allowing the reaction mixture to cool on standing, the reaction mixture was concentrated under a reduced pressure. The resulting residue was purified by silica gel column chromatography (hexane:ethyl acetate=10:1) to obtain 2-bromomethyl-5-iodo-benzofuran (320 mg, 49%).

To an N,N-dimethylformamide (20 mL) solution of 2-bromomethyl-5-iodo-benzofuran (270 mg, 0.801 mmol) and phenol (113 mg, 1.2 mmol) was added potassium carbonate (332 mg, 2.4 mmol). This mixture was stirred at room temperature for 14 hours. The reaction mixture was poured into sat. NaCl and extracted with ethyl acetate. The organic layer was separated and dried over anhydrous magnesium sulfate followed by concentrating under a reduced pressure. The resulting residue was purified by silica gel column chromatography (hexane:ethyl acetate=7:1) to obtain the title compound (251 mg, 90%).

¹H-NMR spectrum (CDCl₃) δ (ppm): 5.16 (2H, s), 6.72 (1H, s), 6.98-7.02 (3H, m), 7.28-7.33 (3H, m), 7.57 (1H, dd, J=1.6 Hz, 8.4 Hz), 7.89 (1H, d, J=1.6 Hz).

Production Example 75-1-2

2-Phenoxymethyl-benzofuran-5-carbonitrile

To a 1-methyl-2-pyrrolidinone (10 mL) solution of 5-iodo-2-phenoxymethyl-benzofuran (250 mg, 0.714 mmol) described in Production Example 75-1-1 were added zinc cyanide (168 mg, 1.43 mmol) and tetraquis(triphenylphosphine) palladium (0) (165 mg, 0.143 mmol). This mixture was stirred at 130° C. for 3 hours. After adding ice water and concentrated aqueous ammonia to the reaction mixture and stirring, the reaction mixture was extracted with ethyl acetate. The organic layer was separated followed by washing with sat. NaCl, drying over anhydrous magnesium sulfate and concentrating under a reduced pressure. The resulting residue was purified by silica gel column chromatography (hexane:ethyl acetate=5:1) to obtain the title compound (27 mg, 15%).

¹H-NMR spectrum (CDCl₃) δ (ppm): 5.19 (2H, s), 6.85 (1H, s), 7.00-7.04 (3H, m), 7.31-7.35 (2H, m), 7.58 (2H, d, J=1.2 Hz), 7.91 (1H, m).

Production Example 75-1-3

C-(2-phenoxymethyl-benzofuran-5-yl)-methylamine

A tetrahydrofuran (1 mL) solution of 2-phenoxymethyl-benzofuran-5-carbonitrile (25 mg, 0.1 mmol) described in Production Example 75-1-2 was dropped into a tetrahydrofuran (5 mL) suspension of lithium aluminum hydride (19 mg, 0.5 mmol). This mixture was stirred at room temperature for 3 hours and 45 minutes. After adding ice water to the reaction mixture and stirring, insoluble matter was filtered out through Celite followed by rinsing with ethyl acetate. The organic layer was separated followed by washing with sat. NaCl, drying over anhydrous magnesium sulfate and concentrating under a reduced pressure to obtain the title compound (12 mg, 47%).

¹H-NMR spectrum (CDCl₃) δ (ppm): 3.90 (2H, s), 5.16 (2H, s), 6.82 (1H, d, J=8.0 Hz), 6.98-7.03 (2H, m), 7.21-7.25 (2H, m), 7.29-7.33 (2H, m), 7.44-7.52 (2H, m).

Example 76

2-Amino-N-(2-(4-fluoro-benzyl)-benzofuran-5-ylmethyl)-6-methoxymethyl-nicotinamide The title compound was obtained from C-(2-(4-fluoro-benzyl)-benzofuran-5-yl)-methylamine described in Production Example 76-1-4 and 2-amino-6-methoxymethyl-nicotinic acid described in Production Example 4-1-5 in accordance with the same method as Example 4.

$^1$H-NMR spectrum (CDCl$_3$) δ (ppm): 3.44 (3H, s), 4.07 (2H, s), 4.38 (2H, s), 7.64 (2H, d, J=5.6 Hz), 6.31 (1H, brs), 6.35 (1H, s), 6.41 (2H, brs), 6.67 (1H, d, J=7.6 Hz), 6.99-7.03 (2H, m), 7.18-7.26 (3H, m), 7.38 (1H, d, J=8.4 Hz), 7.45 (1H, s), 7.58 (1H, d, J=8.0 Hz).

The starting material in the form of C-(2-(4-fluoro-benzyl)-benzofuran-5-yl)-methylamine was synthesized according to the method described below.

Production Example 76-1-1

2-(4-Fluoro-benzyl)-benzofuran-5-carbaldehyde 2-(4-fluorobenzoyl)-1-benzofuran-5-carbaldehyde (500 mg, 1.86 mmol) and ethylene glycol (2.31 g, 37.2 mmol) were suspended in toluene (20 mL) followed by the addition of (1S)-(+)-10-camphorsulfonic acid (30 mg). This suspension was heated under reflux for 2 hours. After allowing the reaction mixture to cool on standing, saturated aqueous sodium bicarbonate solution was poured thereinto followed by extraction with ethyl acetate. The organic layer was separated followed by washing with sat. NaCl and drying over anhydrous magnesium sulfate. The organic layer was filtered using a glass filter and the filtrate was filtered with a glass filter coated with NH-silica gel. This filtrate was concentrated under a reduced pressure to obtain (5-[1,3]-dioxolan-2-yl-benzofuran-2-yl)-(4-fluoro-phenyl)-methanone (377 mg, 65%).

To an ethylene glycol (5 mL) suspension of (5-[1,3]-dioxolan-2-yl-benzofuran-2-yl)-(4-fluoro-phenyl)-methanone (370 mg, 1.18 mmol) were added hydrazine monohydrate (165 mg, 2.8 mmol) and potassium hydroxide (152 mg, 2.71 mmol). After stirring this suspension for 2 hours at 10° C., this suspension was further stirred for 1 hour at 160° C. After allowing the reaction mixture to cool on standing, sat. NaCl was poured thereinto followed by extraction with ethyl acetate. The organic layer was separated followed by drying over anhydrous magnesium sulfate and concentrating under a reduced pressure. The resulting residue was purified by silica gel column chromatography (hexane:ethyl acetate=5:1) to obtain 5-[1,3]-dioxolan-2-yl-2-(4-fluoro-benzyl)-benzofuran (151 mg, 43%).

Into a methylene chloride (4 mL) solution of 5-[1,3]dioxolan-2-yl-2-(4-fluoro-benzyl)-benzofuran (100 mg, 0.335 mmol) and carbon tetrabromide (222 mg, 0.67 mmol) was dropped a methylene chloride (1 mL) solution of triphenylphosphine (176 mg, 0.67 mmol), while cooling with ice.

After stirring this mixture for 1 hour while cooling with ice, this solution was stirred at room temperature for 14 hours. The reaction mixture was concentrated under a reduced pressure and the resulting residue was purified by silica gel column chromatography (hexane:ethyl acetate=5:1) to obtain the title compound (84 mg, 99%).

$^1$H-NMR spectrum (CDCl$_3$) δ (ppm): 4.08 (2H, brs), 6.45 (1H, m), 6.98-7.02 (2H, m), 7.23-7.26 (2H, m), 7.48 (1H, d, J=8.8 Hz), 7.76 (1H, dd, J=1.6 Hz, 8.4 Hz), 7.99 (1H, d, J=1.6 Hz), 9.99 (1H, s).

Production Example 76-1-2

(2-(4-Fluoro-benzyl)-benzofuran-5-yl)-methanol

To a methanol (5 mL) solution of 2-(4-fluoro-benzyl)-benzofuran-5-carbaldehyde (84 mg, 0.33 mmol) described in Production Example 76-1-1 was added sodium borohydride (18.7 mg, 0.495 mmol).

This mixture was stirred at room temperature for 30 minutes. Sat. NaCl was poured into the reaction mixture followed by extraction with ethyl acetate. The organic layer was separated followed by drying over anhydrous magnesium sulfate and concentrating under a reduced pressure to obtain the title compound (83 mg, 98%).

$^1$H-NMR spectrum (CDCl$_3$) δ (ppm): 4.07 (2H, s), 4.73 (2H, s), 6.35 (1H, m), 6.99-7.03 (2H, m), 7.20-7.27 (3H, m), 7.38 (1H, d, J=8.4 Hz), 7.47 (1H, m).

Production Example 76-1-3

2-(2-(4-fluoro-benzyl)-benzofuran-5-ylmethyl)-isoindole-1,3-dione

To a tetrahydrofuran (5 mL) solution of (2-(4-fluoro-benzyl)-benzofuran-5-yl)-methanol (83 mg, 0.324 mmol) described in Production Example 76-1-2 were added triphenylphosphine (93.5 mg, 0.356 mmol), phthalimide (52.4 mg, 0.356 mmol) and diethylazodicarboxylate (62.1 mg, 0.356 mmol). This mixture was stirred at room temperature for 14 hours. The reaction mixture was concentrated and the resulting residue was purified by silica gel column chromatography (hexane:ethyl acetate=5:1) to obtain the title compound (81 mg, 65%).

$^1$H-NMR spectrum (CDCl$_3$) δ (ppm): 4.04 (2H, s), 4.90 (2H, s), 6.33 (1H, s), 6.96-7.01 (2H, m), 7.20-7.24 (2H, m), 7.32-7.33 (2H, m), 7.57 (1H, s), 7.68-7.70 (2H, m), 7.82-7.84 (2H, m).

Production Example 76-1-4

C-(2-(4-fluoro-benzyl)-benzofuran-5-yl)-methylamine

To a mixed solution of 2-(2-(4-fluoro-benzyl)-benzofuran-5-ylmethyl)-isoindole-1,3-dione (81 mg, 0.21 mmol) described in Production Example 76-1-3 in ethanol (5 mL) and tetrahydrofuran (3 mL) was added hydrazine monohydrate (52.6 mg, 1.05 mmol). This mixture was stirred for 3 hours while heating under reflux. After allowing the reaction mixture to cool on standing, saturated aqueous sodium bicarbonate solution was poured thereinto followed by extraction with ethyl acetate. The organic layer was separated followed by washing with sat. NaCl, drying over anhydrous magnesium sulfate and concentrating under a reduced pressure to obtain the title compound (42 mg, 78%).

$^1$H-NMR spectrum (CDCl$_3$) δ (ppm): 3.91 (2H, s), 4.06 (2H, s), 6.34 (1H, s), 6.98-7.03 (2H, m), 7.16 (1H, dd, J=1.6 Hz, 8.4 Hz), 7.23-7.27 (2H, m), 7.35 (1H, d, J=8.4 Hz), 7.41 (1H, s).

Example 77

2-Amino-N-(6-benzyloxy-benzo[b]thiophen-2-ylmethyl)-6-methoxymethyl-nicotinamide The title compound was obtained from C-(6-benzyloxy-benzo[b]thiophen-2-yl)-methylamine described in Production Example 77-1-5 and 2-amino-6-methoxymethyl-nicotinamide described in Production Example 4-1-5 in accordance with the same method as Example 4.

$^1$H-NMR spectrum (CDCl$_3$) δ (ppm): 3.46 (3H, s), 4.40 (2H, s), 4.80-4.81 (2H, m), 5.12 (2H, s), 6.37-6.40 (3H, m), 6.70 (1H, d, J=8.0 Hz), 7.05 (1H, dd, J=2.4 Hz, 8.4 Hz), 7.16 (1H, s), 7.33-7.35 (2H, m), 7.38-7.42 (2H, m), 7.44-7.47 (2H, m), 7.59-7.62 (2H, m).

The starting material in the form of C-(6-benzyloxy-benzo[b]thiophen-2-yl)-methylamine was synthesized according to the method described below.

Production Example 77-1-1

6-Methoxy-benzo[b]thiophene-2-carboxylic acid ethyl ester

To an N,N-dimethylformamide (50 mL) solution of 2-fluoro-4-methoxybenzaldehyde (5.0 g, 32.5 mmol) and 2-mercapto-acetate (3.56 mL, 32.5 mmol) was added potassium carbonate (12.1 g, 87.5 mmol). This mixture was stirred at room temperature for 5 hours. The reaction mixture was distributed between ethyl acetate and water. The organic layer was separated followed by washing with water, drying over anhydrous magnesium sulfate and filtering. The filtrate was concentrated under a reduced pressure and the resulting residue was purified by silica gel chromatography (heptane:ethyl acetate=20:1 to 10:1) and NH silica gel chromatography (heptane:ethyl acetate=10:1) to obtain the title compound (6.72 g, 88%).

$^1$HNMR spectrum (CDCl$_3$) δ (ppm): 1.41 (3H, t, J=7.2 Hz), 3.90 (3H, s), 4.39 (2H, q, J=7.2 Hz), 7.02 (1H, dd, J=2.4 Hz, 9.0 Hz), 7.29 (1H, d, J=2.4 Hz), 7.74 (1H, d, J=9.0 Hz), 7.97 (1H, s).

Production Example 77-1-2

(6-Methoxy-benzo[b]thiophen-2-yl)-methanol

To a tetrahydrofuran (100 mL) solution of (6-methoxy-benzo[b]-thiophene-2-carboxylic acid ethyl ester (5.0 g, 21.1 mmol) described in Production Example 77-1-1 was added lithium aluminum hydride (2.0 g, 52.8 mmol). The suspension was stirred at room temperature for 30 minutes. The reaction mixture was distributed between water and ethyl acetate. The organic layer was separated followed by drying over anhydrous magnesium sulfate and filtering. The residue was concentrated under a reduced pressure to obtain the title compound (4.1 g, quantitative).

$^1$H-NMR spectrum (CDCl$_3$) δ (ppm): 1.92 (1H, t, J=6.0 Hz), 3.86 (3H, s), 4.87 (2H, d, J=6.0 Hz), 6.97 (1H, dd, J=2.4 Hz, 8.8 Hz), 7.12 (1H, s), 7.29 (1H, d, J=2.4 Hz), 7.60 (1H, d, J=8.8 Hz).

Production Example 77-1-3

2-(6-Methoxy-benzo[b]thiophen-2-ylmethyl-isoindole-1,3-dione

To a tetrahydrofuran (40 mL) solution of (6-methoxy-benzo[b]thiophen-2-yl)-methanol (4.1 g, 21.1 mmol) described in Production Example 77-1-2 were added diethyl azodicarboxylate (3.32 mL, 21.1 mmol), phthalimide (3.1 g, 21.1 mmol) and triphenylphosphine (5.53 g, 21.1 mmol). The mixture was stirred at room temperature for 3 hours. The reaction mixture was concentrated under a reduced pressure and the resulting residue was purified by silica gel chromatography (heptane:ethyl acetate=10:1 to 4:1) to obtain the title compound (2.34 g, 34%).

$^1$H-NMR spectrum (CDCl$_3$) δ (ppm): 3.83 (3H, s), 5.06 (2H, s), 6.94 (1H, dd, J=2.4 Hz, 8.8 Hz), 7.21 (1H, d, J=2.4 Hz), 7.58 (1H, d, J=8.8 Hz), 7.70-7.78 (3H, m), 7.85-7.89 (2H, m).

Production Example 77-1-4

2-(6-Benzyloxy-benzo[b]thiophen-2-ylmethyl)-isoindole-1,3-dione

Into a methylene chloride (10 mL) solution of 2-(6-methoxy-benzo[b]thiophen-2-ylmethyl-isoindole-1,3-dione (1.0 g, 3.09 mmol) described in Production Example 77-1-3 was dropped a heptane (1 M) solution of boron tribromide (15.5 mL, 15.5 mmol) while cooling with ice. The mixture was stirred at 0° C. for 4 hours. The reaction mixture was made alkaline with saturated aqueous sodium bicarbonate solution followed by extraction with ethyl acetate. The organic layer was separated followed by drying over anhydrous magnesium sulfate and filtering. The filtrate was concentrated under a reduced pressure to obtain 2-(6-hydroxy-benzo[b]thiophen-2-ylmethyl)-isoindole-1,3-dione (540 mg, 57%).

To an N,N-dimethylformamide (3 mL) solution of 2-(6-hydroxy-benzo[b]thiophen-2-ylmethyl)-isoindole-1,3-dione (121 mg, 0.391 mmol) were added potassium carbonate (162 mg, 1.17 mmol) and benzyl bromide (70 μL, 0.587 mmol). The mixture was stirred at 100° C. for 30 minutes. The reaction mixture was distributed between ethyl acetate and water. The organic layer was washed with water followed by drying over anhydrous magnesium sulfate and filtering. The filtrate was concentrated under a reduced pressure and the resulting residue was purified by silica gel chromatography (hexane:ethyl acetate=10:1 to 4:1 and then 1:1) to obtain the title compound (144 mg, 92%).

$^1$H-NMR spectrum (DMSO-d$_6$) δ (ppm): 5.05 (2H, s), 5.09 (2H, s), 7.00-7.03 (2H, m), 7.26-7.45 (4H, m), 7.58-7.60 (1H, m), 7.70-7.72 (2H, m), 7.82-7.87 (3H, m), 7.98-8.00 (1H, m).

Production Example 77-1-5

C-(6-benzyloxy-benzo[b]thiophen-2-yl)-methylamine

To an ethanol (5 mL) solution of 2-(6-benzyloxy-benzo[b]thiophen-2-ylmethyl)-isoindole-1,3-dione (144 mg, 0.36 mmol) described in Production Example 77-1-4 was added hydrazine monohydrate (18.7 mg, 0.374 mmol). The mixture was stirred for 4 hours while heating under reflux. The reaction mixture was allowed to cool on standing followed by the addition of water and concentrating under a reduced pressure until the total volume of the solution was reduced by half. The solution was distributed between ethyl acetate and water. The organic layer was separated followed by washing with 2 N aqueous sodium hydroxide solution and water, drying over anhydrous magnesium sulfate and filtering. The filtrate was concentrated under a reduced pressure to obtain the title compound (104 mg, quantitative). This amine was used in the subsequent reaction without purifying.

Example 78

2,6-Diamino-N-(6-benzyloxy-benzo[b]thiohen-2-ylmethyl)-nicotinamide

The title compound was obtained from C-(6-benzyloxy-benzo[b]-thiophen-2-yl)-methylamine described in Production Example 77-1-5 and 2,6-diaminonicotinic acid described in Production Example 1-1-4 in accordance with the same method as Example 1.

$^1$H-NMR spectrum (CDCl$_3$) δ (ppm): 4.51 (2H, brs), 4.77 (2H, d, J=6.0 Hz), 5.12 (2H, s), 5.78 (1H, d, J=8.4 Hz), 6.11 (1H, brs), 6.45 (2H, brs), 7.04 (1H, dd, J=2.4 Hz, 8.8 Hz), 7.13 (1H, s), 7.31-7.35 (2H, m), 7.37-7.41 (3H, m), 7.44-7.46 (2H, m), 7.59 (1H, d, J=8.8 Hz).

Example 79

2-Amino-N-(5-bromo-benzofuran-2-ylmethyl)-6-methoxymethyl-nicotinamide

To an N,N-dimethylformamide (10 mL) solution of C-(5-bromo-benzofuran-2-yl)-methylamine (455 mg, 2.01 mmol) described in Production Example 56-1-4 were added 2-amino-6-methoxymethyl-nicotinic acid (293 mg, 1.61 mmol) described in Production Example 4-1-5, triethylamine (700 μL, 5.03 mmol) and benzotriazol-1-yloxytris(dimethylamino)phosphonium hexafluorophosphate (1.07 g, 2.41 mmol) at room temperature, which was stirred for 12 hours. Water was added to the reaction solution at room temperature followed by extraction with ethyl acetate. The organic layer was washed with water and sat. NaCl followed by drying over anhydrous magnesium sulfate, filtering and concentrating the filtrate under a reduced pressure. The residue was purified by NH silica gel column chromatography (heptane:ethyl acetate=1:1) to obtain the title compound (255 mg, 33%) as a white solid.

$^1$H-NMR spectrum (DMSO-d$_6$) δ (ppm): 3.35 (3H, s), 4.30 (2H, s), 4.60 (2H, d, J=5.1 Hz), 6.62 (1H, d, J=7.9 Hz), 6.75 (1H, s), 7.15 (2H, brs), 7.40 (1H, ddd, J=0.9 Hz, 1.1 Hz, 8.6 Hz), 7.54 (1H, d, J=8.6 Hz), 7.80 (1H, d, J=2.2 Hz), 8.00 (1H, d, J=8.1 Hz), 9.05 (1H, t, J=5.9 Hz).

Example 80

2,6-Diamino-N-(6-(2-phenoxy-ethoxy)-benzofuran-2-ylmethyl)-nicotinamide

The title compound was obtained in accordance with the same method as Example 2.
MS m/e (ESI): 341.19 (MH$^+$)

Example 81

2-Amino-N-(5-ethoxymethyl-benzofuran-2-ylmethyl)-6-methoxymethyl-nicotinamide

The title compound was obtained from 2-amino-N-(5-bromo-benzofuran-2-ylmethyl)-6-methoxymethylnicotinamide described in Production Example 56-1-5 and tributyl-ethoxymethyl-stannane described in Production Example 81-1 in accordance with the same method as Example 47.
MS m/e (ESI): 370.21 (MH$^+$)

Production Example 81-1

Tributyl-ethoxymethyl-stannane

To a mixture of diisopropylamine (2.1 mL, 15 mmol) and tetrahydrofuran (30 mL) was dropped n-butyl lithium (2.4 M n-hexane solution, 5.0 mL, 12 mmol) at −78° C., which was stirred for 30 minutes at the same temperature. Tributyl tin hydride (3.3 mL, 12 mmol) was dropped at the same temperature followed by stirring for 40 minutes under ice-cold conditions. The reaction mixture was cooled to −78° C. and chloromethyl ethyl ether (1.1 mL, 12 mmol) was dropped into the reaction mixture. The reaction mixture was gradually warmed to room temperature followed by additionally stirring at room temperature for 3 hours. The reaction mixture was distributed among water (100 mL), saturated aqueous ammonia (50 mL) and diethyl ether (100 mL). The organic layer was separated followed by washing with sat. NaCl and concentrating under a reduced pressure. The residue was purified by neutral silica gel column chromatography (heptane:diethyl ether=30:1) to obtain the title compound (2.8 g, 65%) as a colorless oil.

$^1$H-NMR spectrum (CDCl$_3$) δ (ppm): 0.87-0.92 (15H, m), 1.16 (3H, t, J=7.0 Hz), 1.26-1.35 (6H, m), 1.43-1.55 (6H, m), 3.36 (2H, q, J=7.0 Hz), 3.74 (2H, t, J=6.5 Hz).

The structural formulas of the compounds obtained in the above-mentioned production examples and examples are shown in the following Tables 1 to 12.

TABLE 1

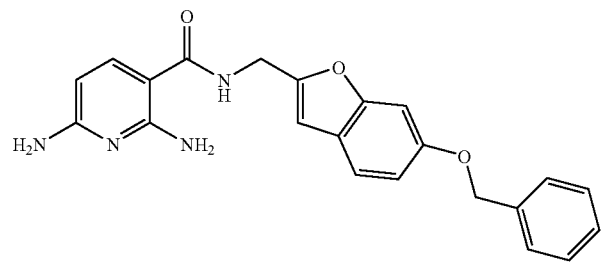

Example 1

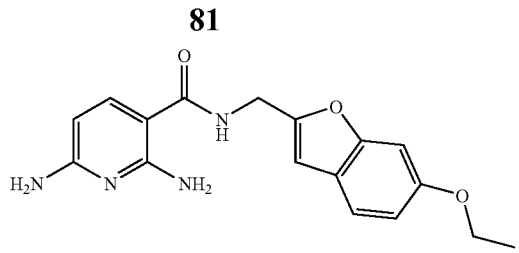
Example 2
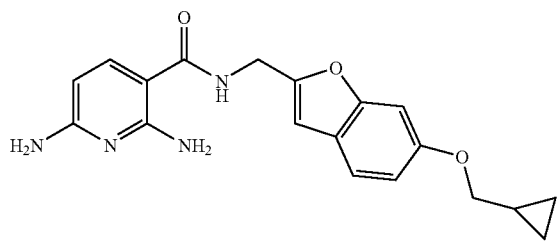
Example 3
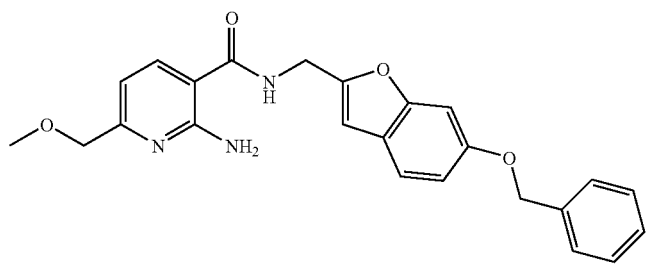
Example 4
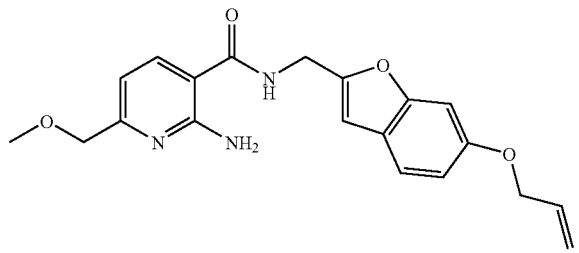
Example 5
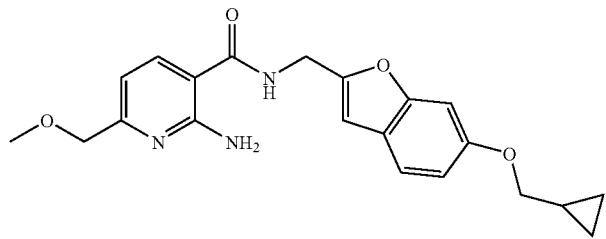
Example 6

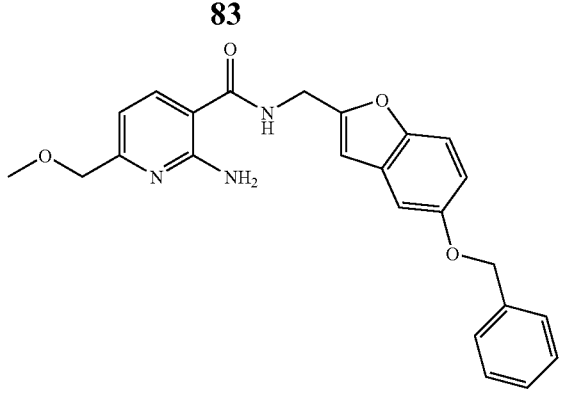
Example 7
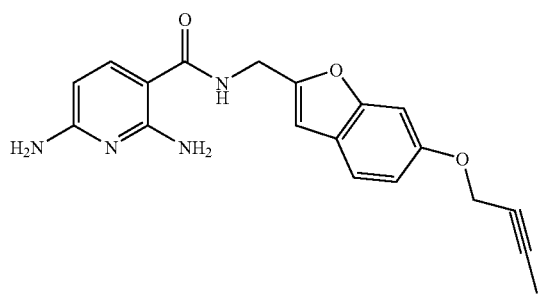
Example 8
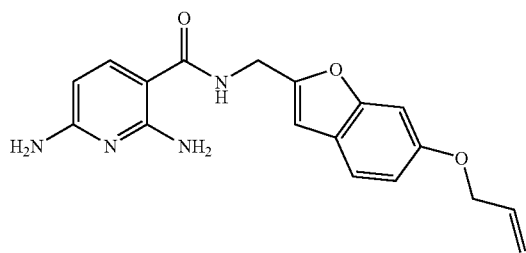
Example 9
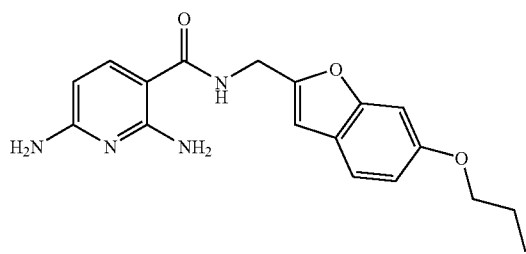
Example 10
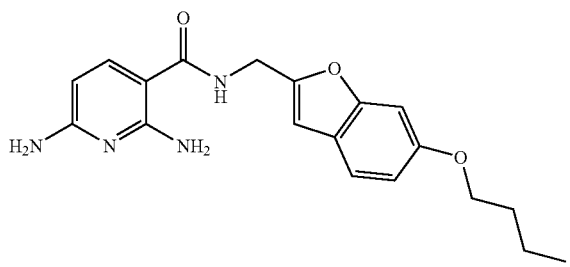
Example 11

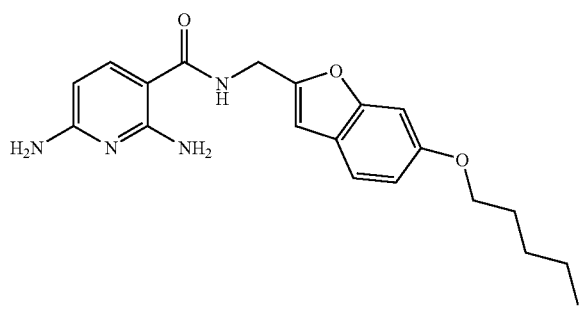
Example 12
TABLE 2
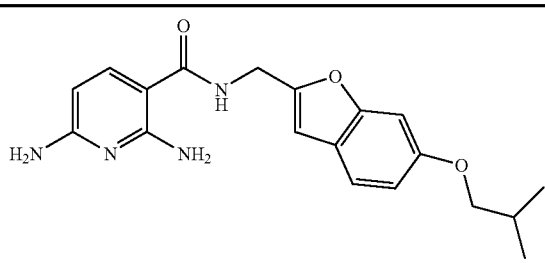
Example 13
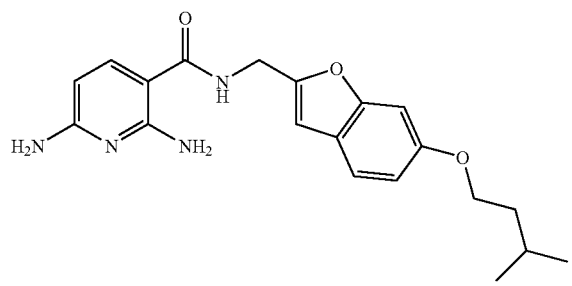
Example 14
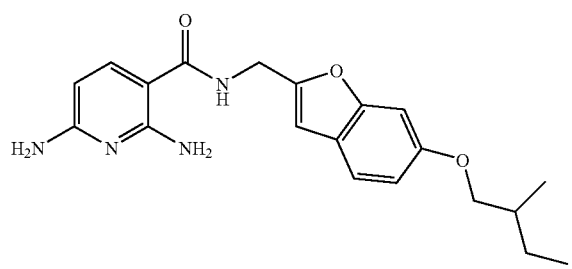
Example 15
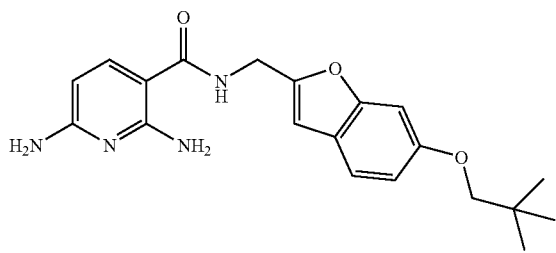
Example 16

TABLE 2-continued
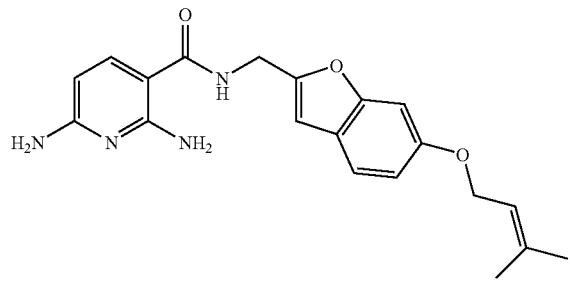
Example 17
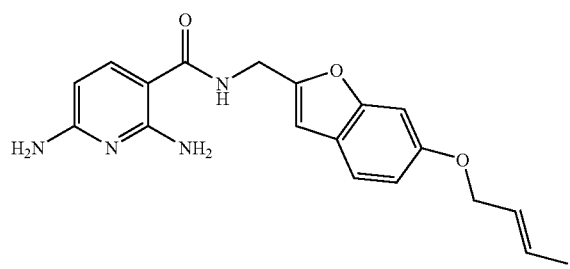
Example 18
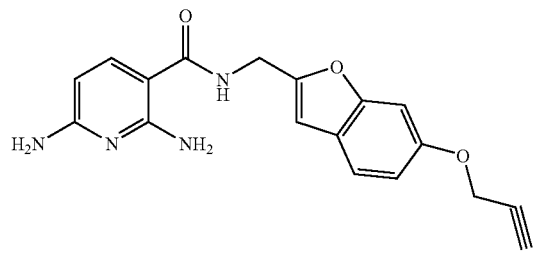
Example 19
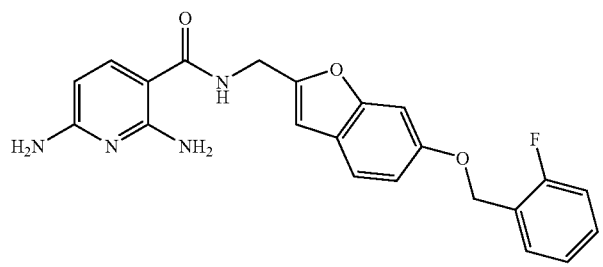
Example 20
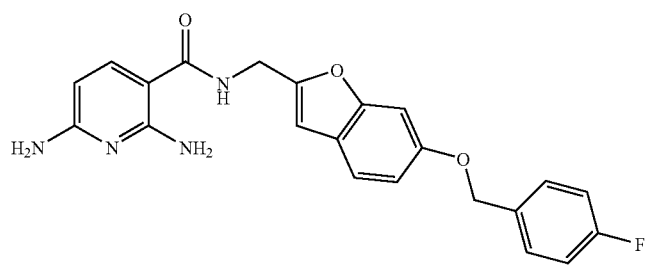
Example 21

TABLE 2-continued
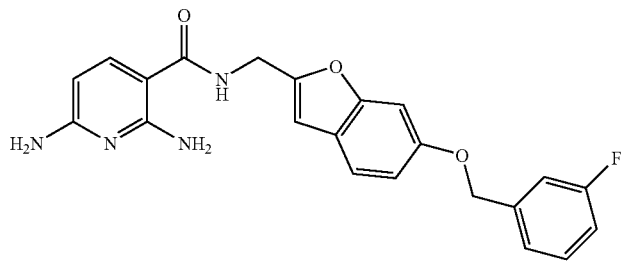
Example 22
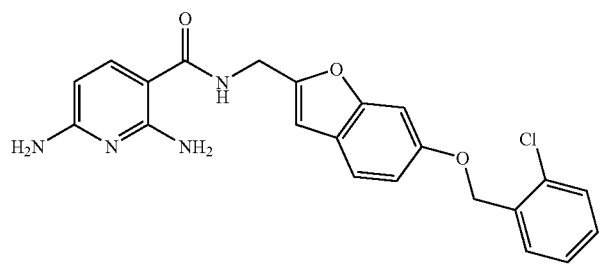
Example 23
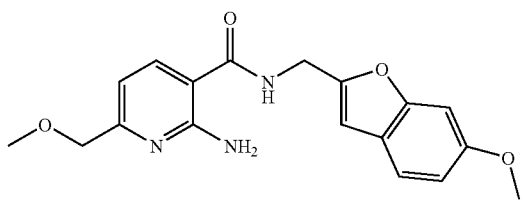
Example 24
TABLE 3
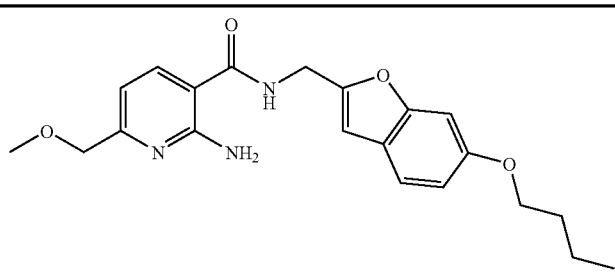
Example 25
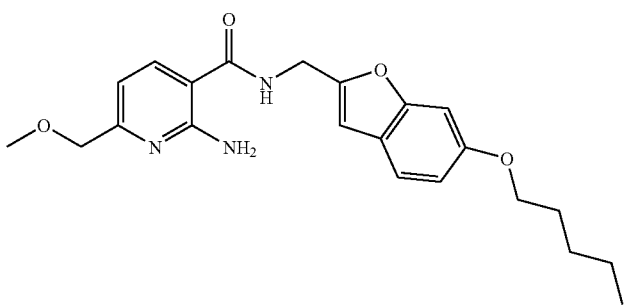
Example 26

TABLE 3-continued
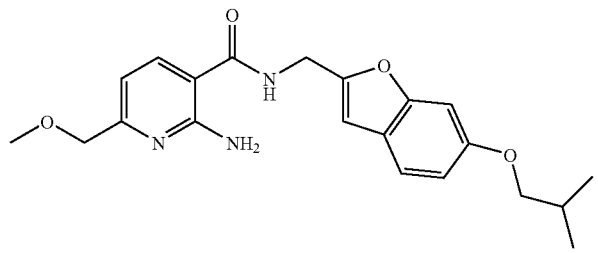
Example 27
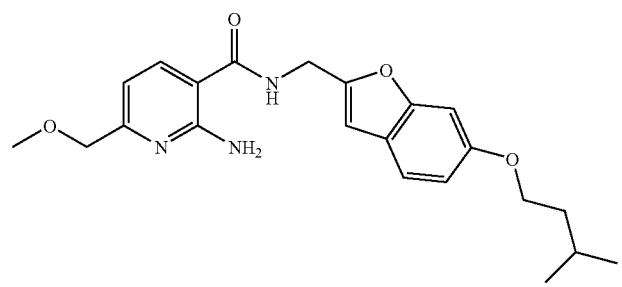
Example 28
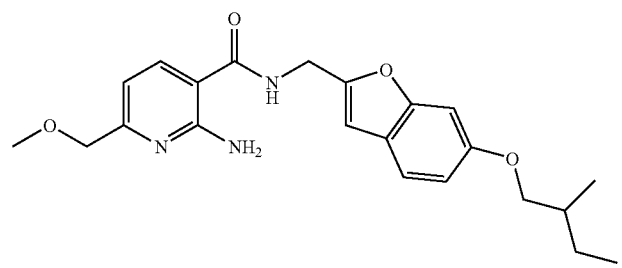
Example 29
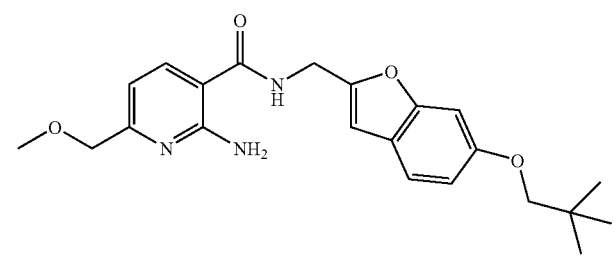
Example 30
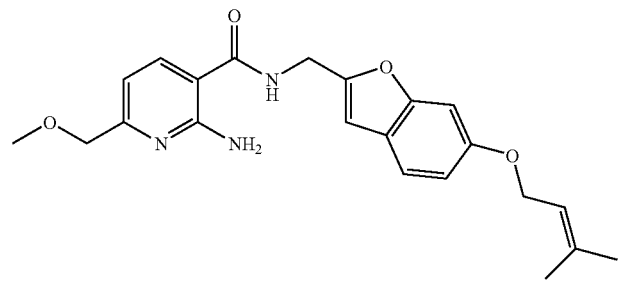
Example 31

TABLE 3-continued
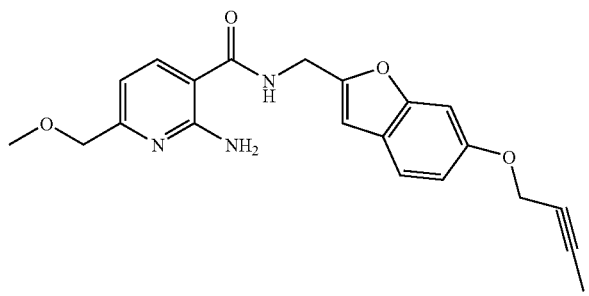
Example 32
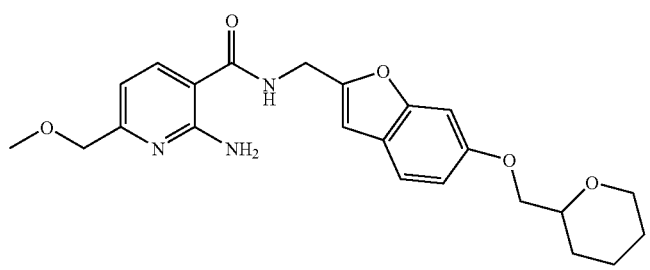
Example 33
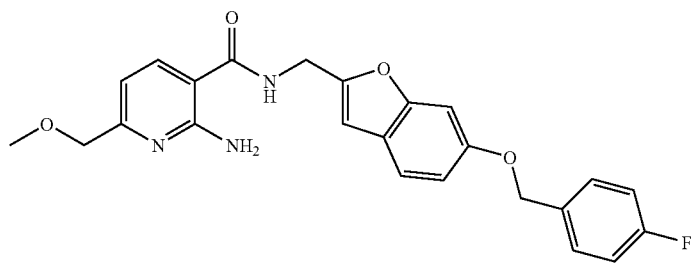
Example 34
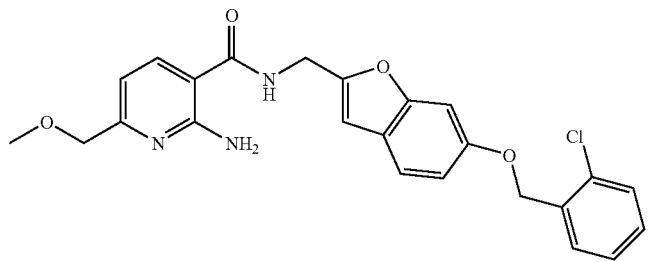
Example 35
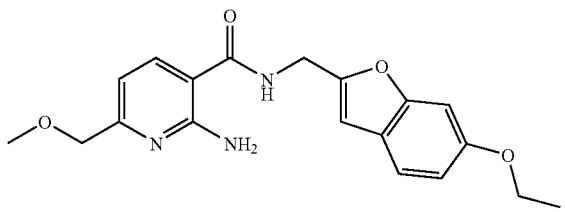
Example 36

TABLE 4
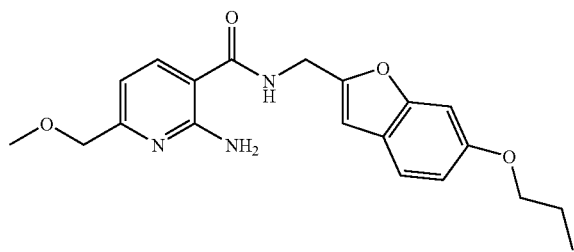
Example 37
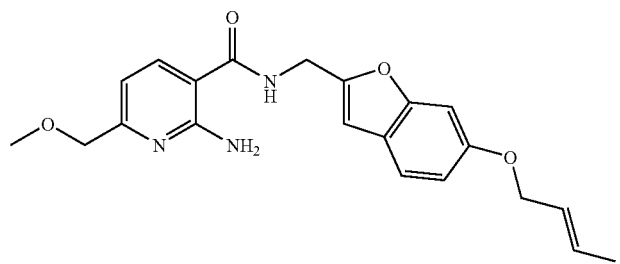
Example 38
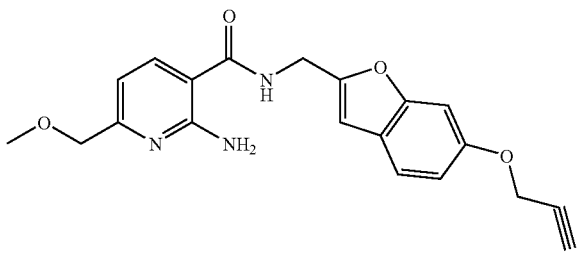
Example 39
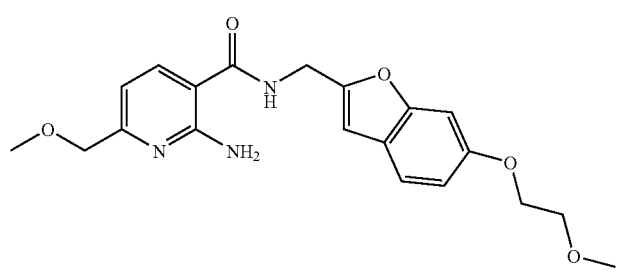
Example 40
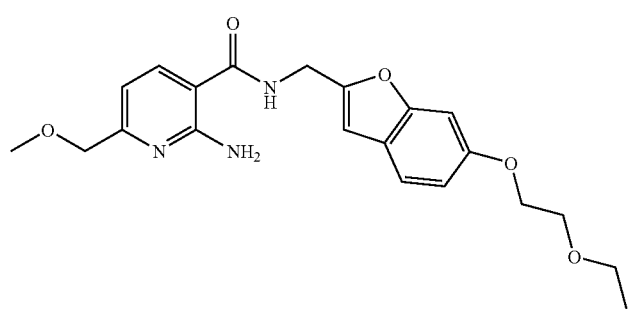
Example 41

TABLE 4-continued
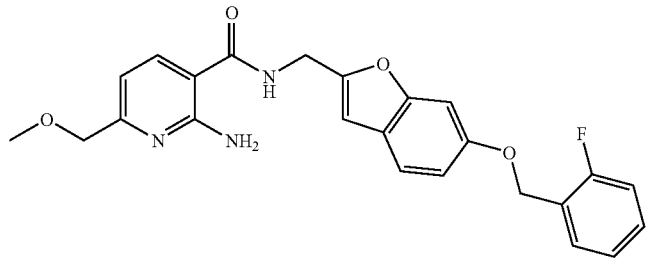
Example 42
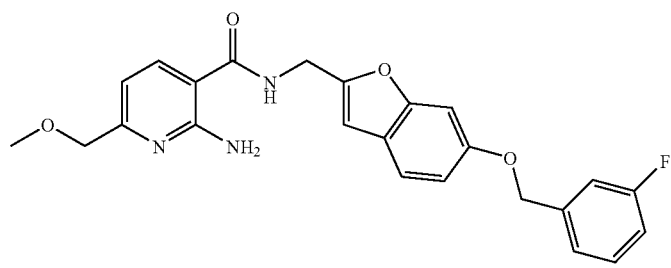
Example 43
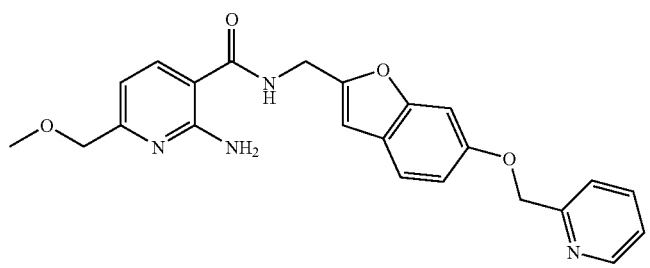
Example 44
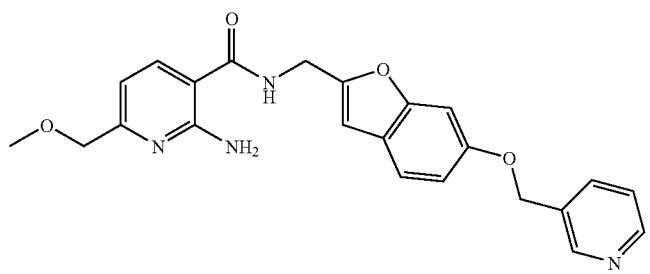
Example 45
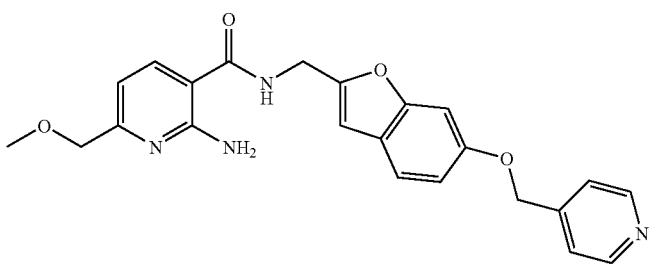
Example 46

TABLE 4-continued
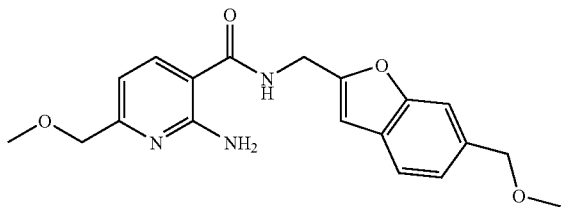
Example 47
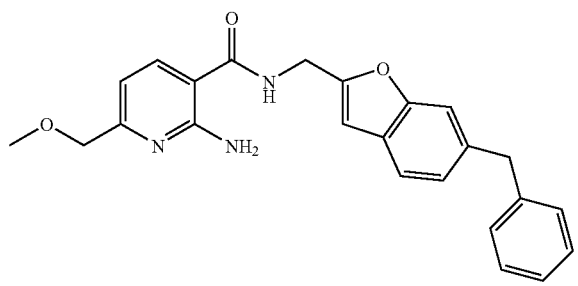
Example 48
TABLE 5
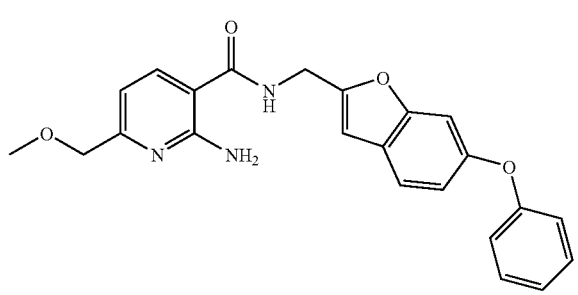
Example 49
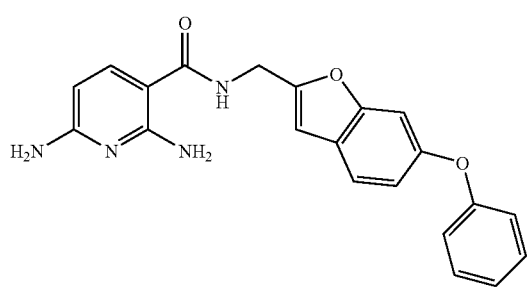
Example 50
TABLE 5-continued
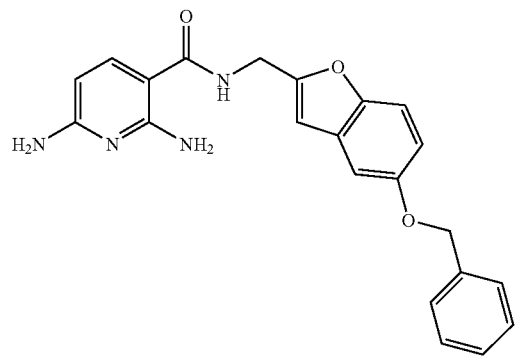
Example 51
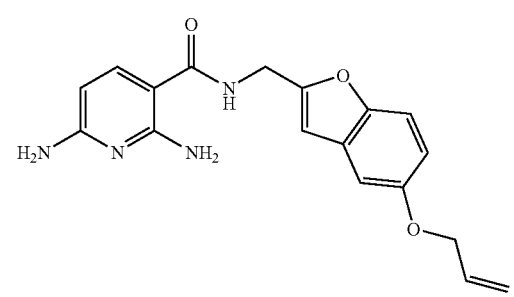
Example 52

TABLE 5-continued
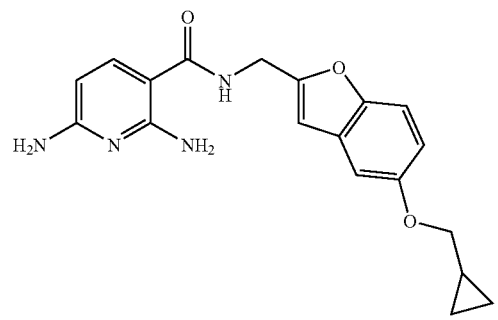
Example 53
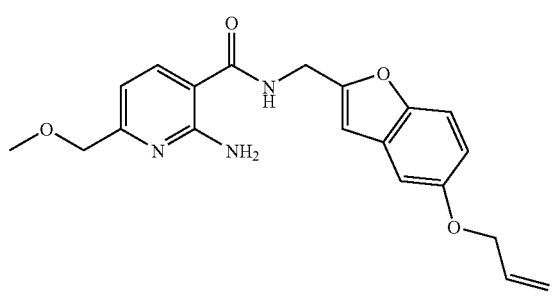
Example 54
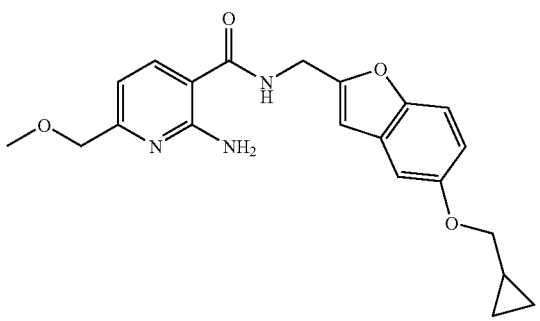
Example 55
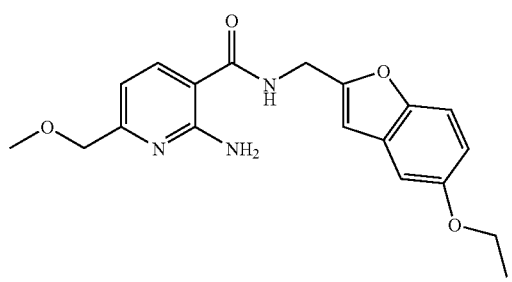
Example 56
TABLE 5-continued
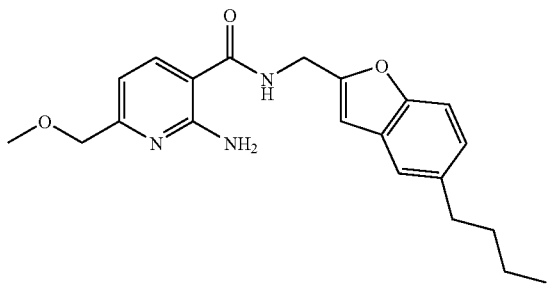
Example 57
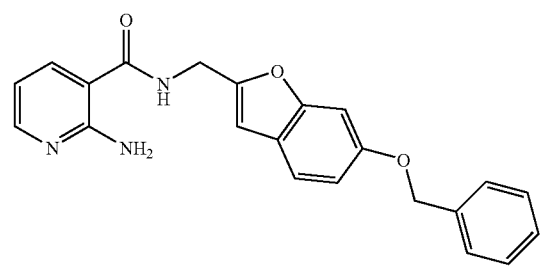
Example 58
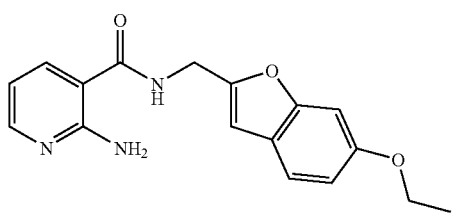
Example 59
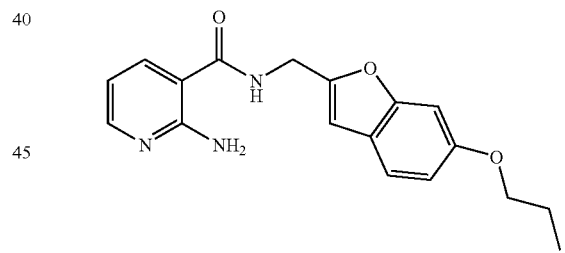
Example 60
TABLE 6
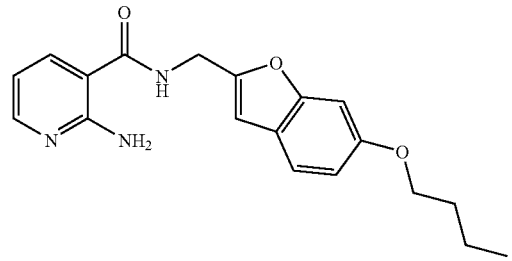
Example 61

TABLE 6-continued
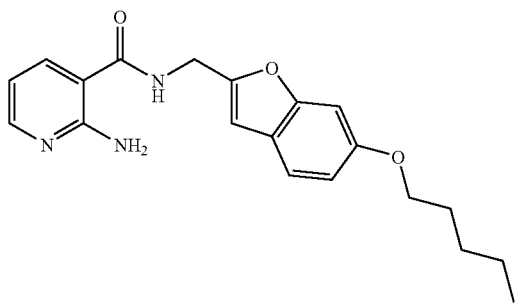
Example 62
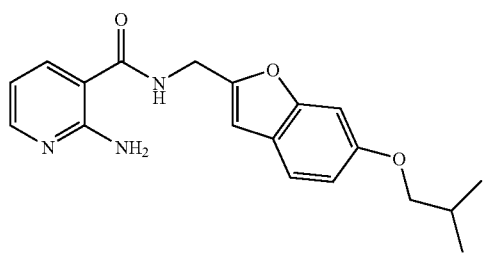
Example 63
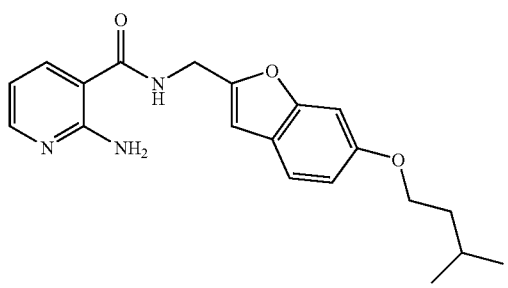
Example 64
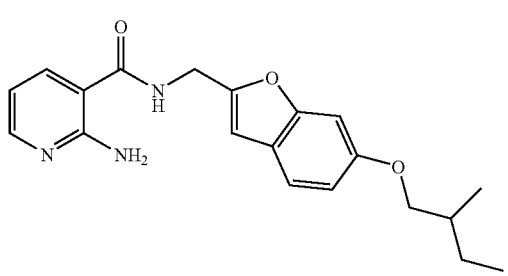
Example 65
TABLE 6-continued
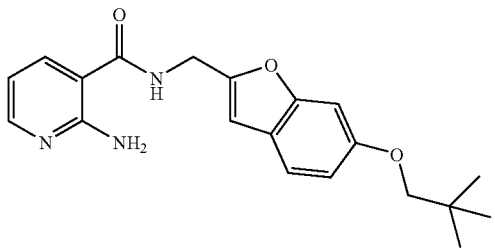
Example 66
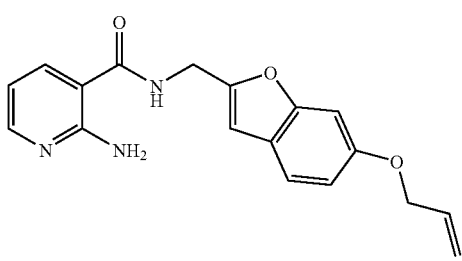
Example 67
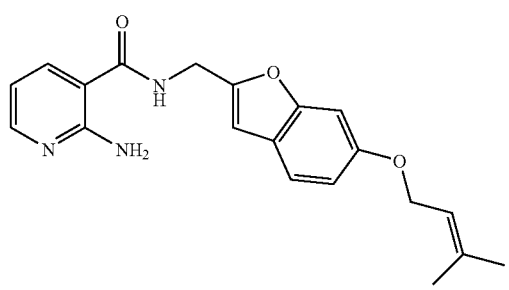
Example 68
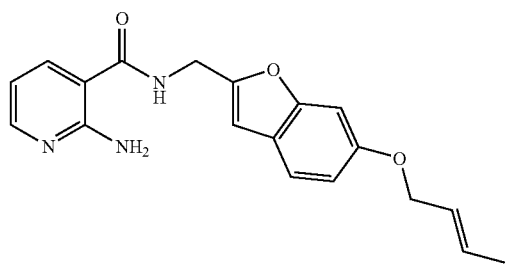
Example 69
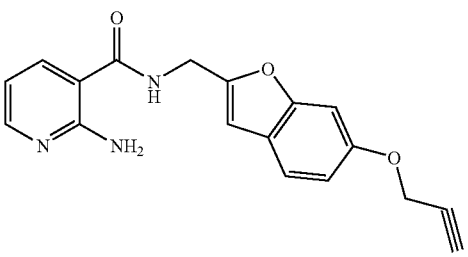
Example 70

TABLE 6-continued
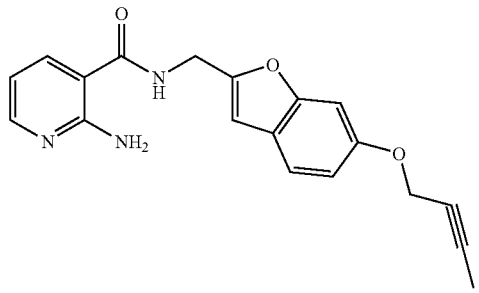
Example 71
TABLE 6-continued
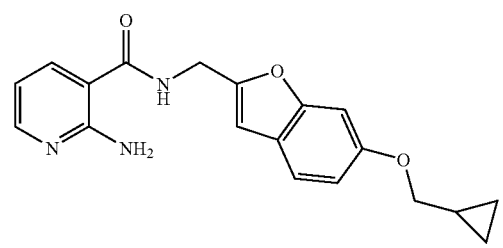
Example 72
TABLE 7
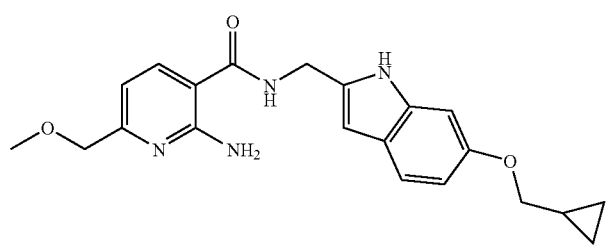
Example 73
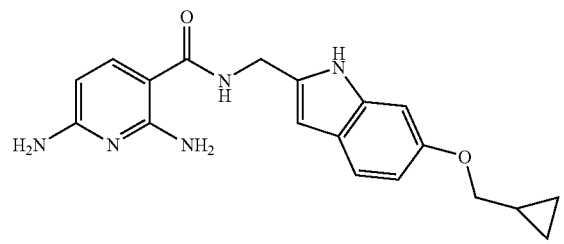
Example 74
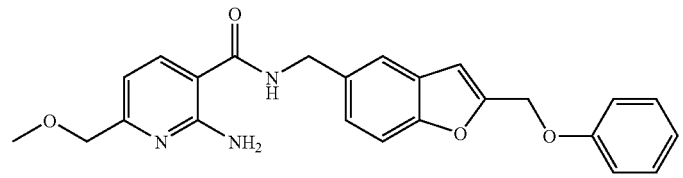
Example 75
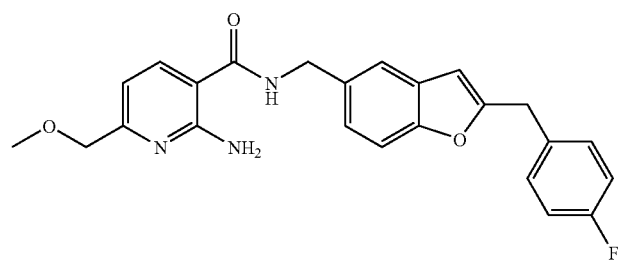
Example 76

TABLE 7-continued
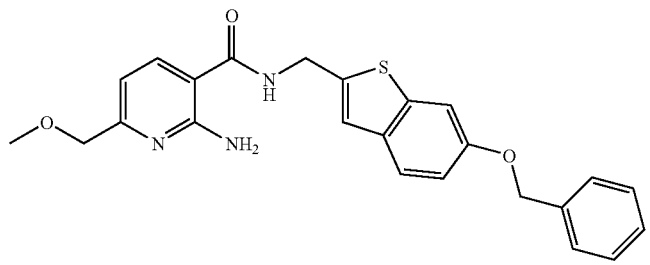
Example 77
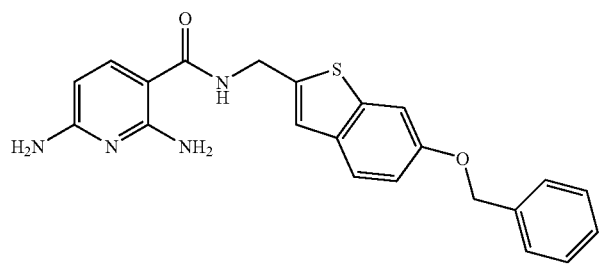
Example 78
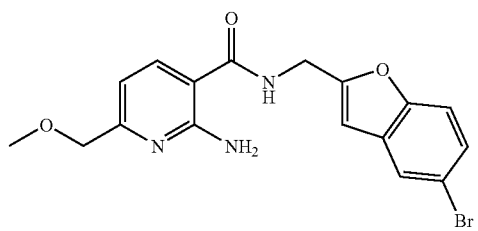
Example 79
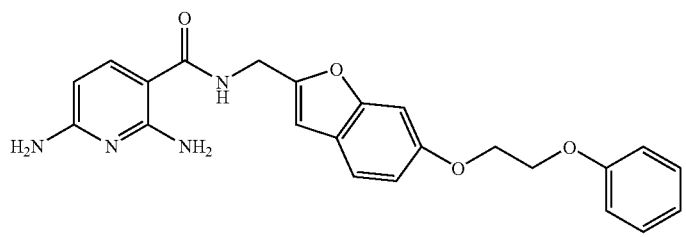
Example 80
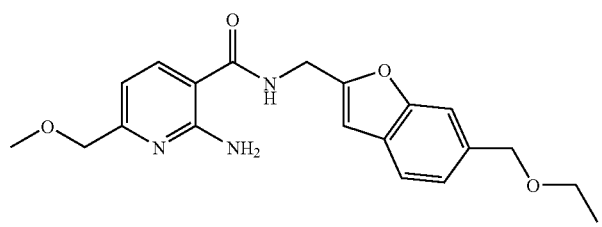
Example 81

TABLE 8
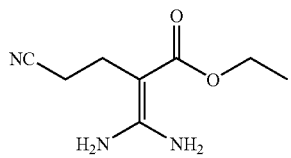
Production Example 1-1-1
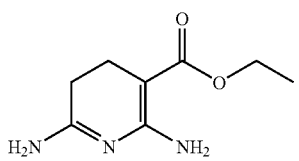
Production Example 1-1-2
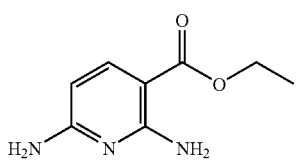
Production Example 1-1-3
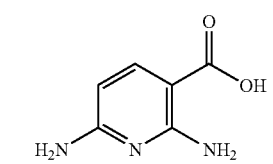
Production Example 1-1-4
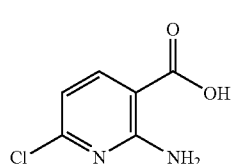
Production Example 4-1-1
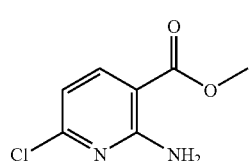
Production Example 4-1-2
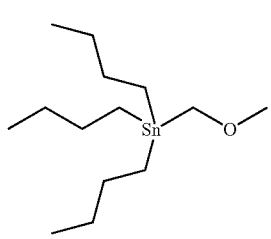
Production Example 4-1-3
TABLE 8-continued
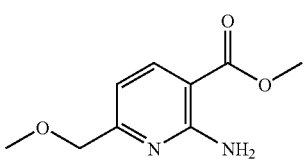
Production Example 4-1-4
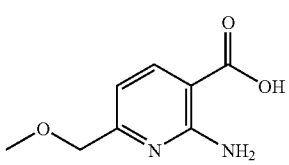
Production Example 4-1-5
TABLE 9
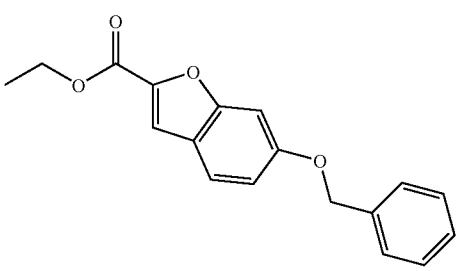
Production Example 1-2-1
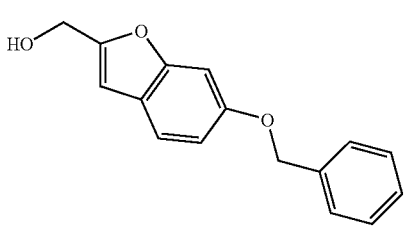
Production Example 1-2-2
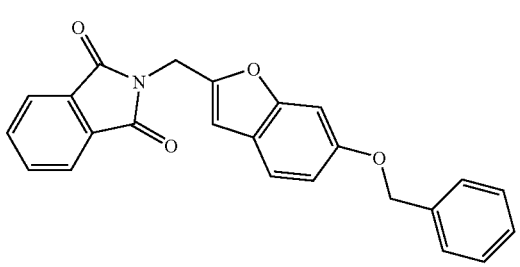
Production Example 1-2-3

TABLE 9-continued
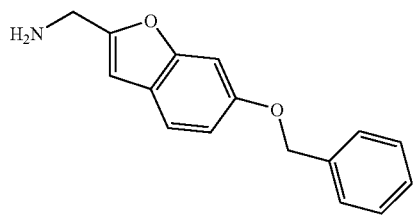
Production Example 1-2-4
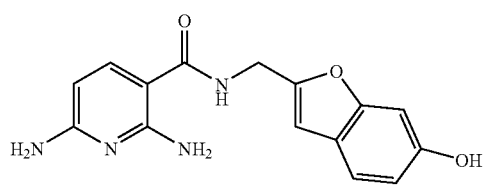
Production Example 2-1
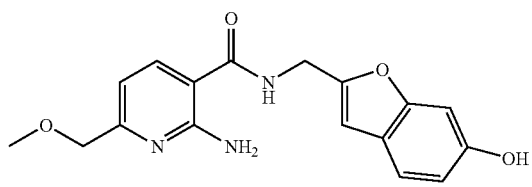
Production Example 5-1
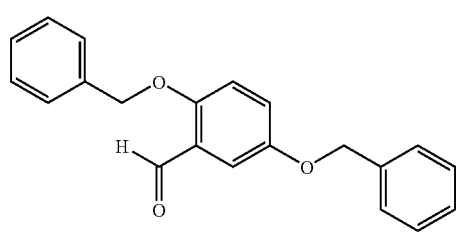
Production Example 7-1-1
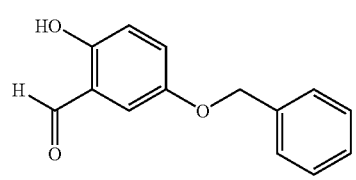
Production Example 7-1-2
TABLE 9-continued
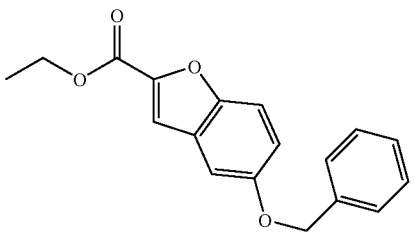
Production Example 7-1-3
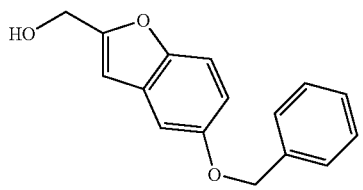
Production Example 7-1-4
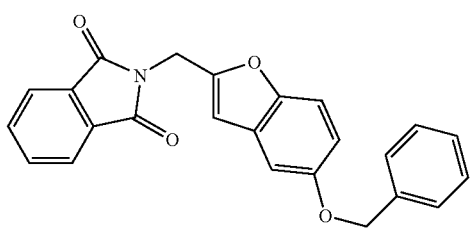
Production Example 7-1-5
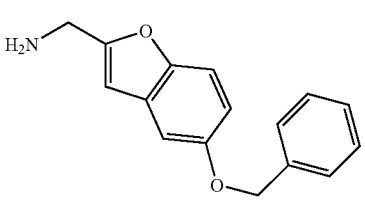
Production Example 7-1-6

TABLE 10
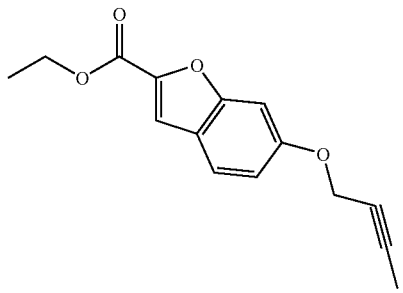
Production Example 8-1-1
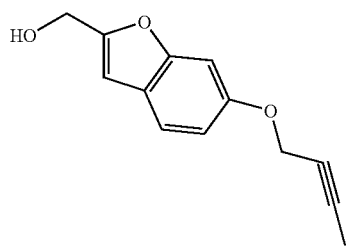
Production Example 8-1-2
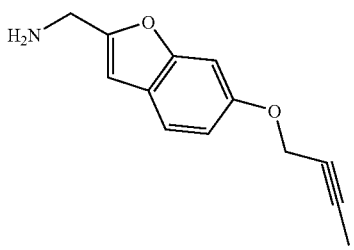
Production Example 8-1-3
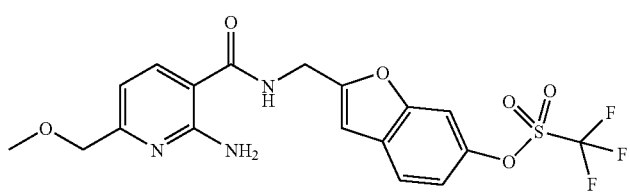
Production Example 47-1
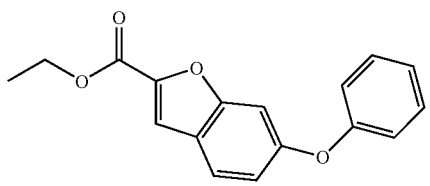
Production Example 49-1-1
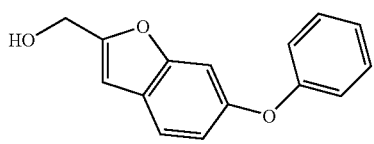
Production Example 49-1-2

TABLE 10-continued
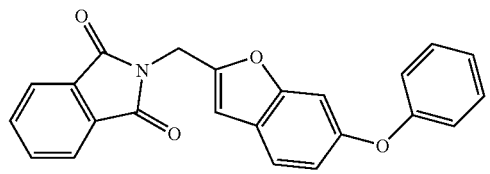
Production Example 49-1-3
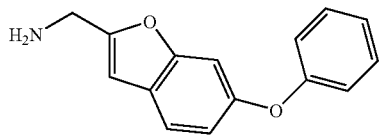
Production Example 49-1-4
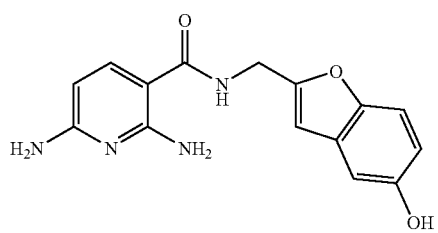
Production Example 52-1
TABLE 11
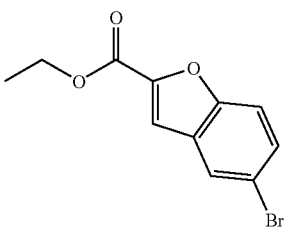
Production Example 56-1-1
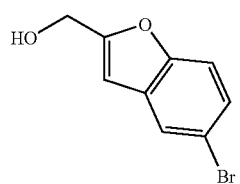
Production Example 56-1-2
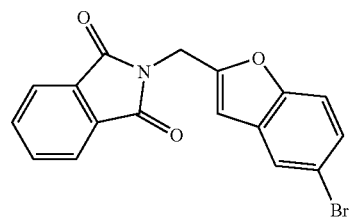
Production Example 56-1-3
TABLE 11-continued
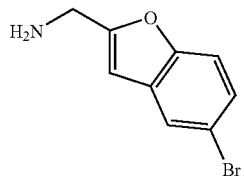
Production Example 56-1-4
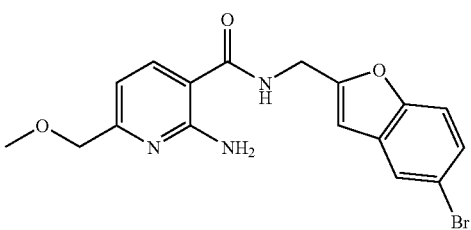
Production Example 56-1-5
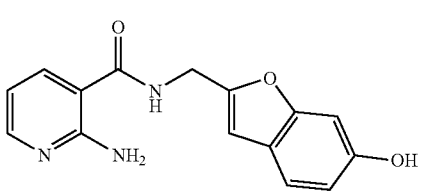
Production Example 59-1

TABLE 11-continued
Production Example 73-1-1
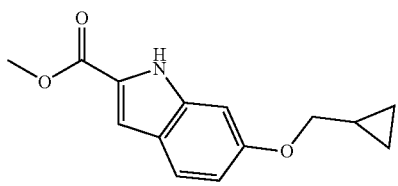
Production Example 73-1-2
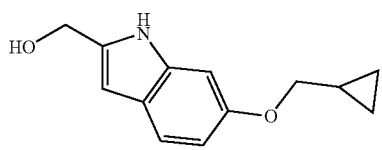
Production Example 73-1-3
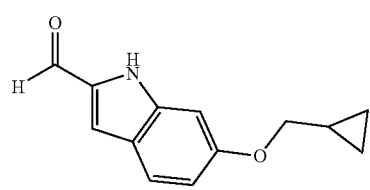
Production Example 73-1-4
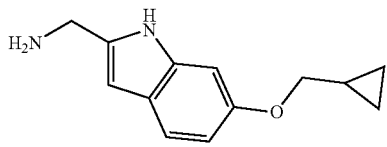
Production Example 73-1-5
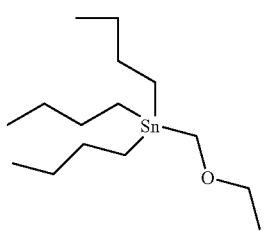
Production Example 81-1
TABLE 12
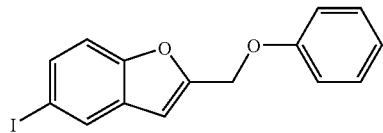
Production Example 75-1-1
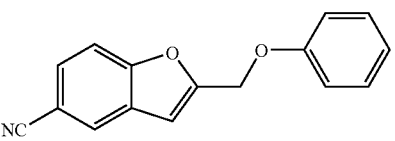
Production Example 75-1-2
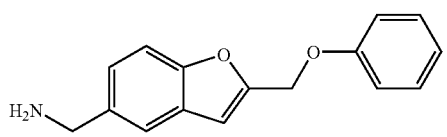
Production Example 75-1-3
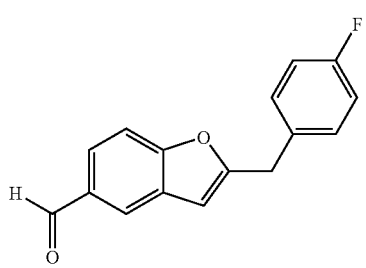
Production Example 76-1-1
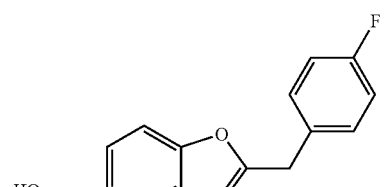
Production Example 76-1-2
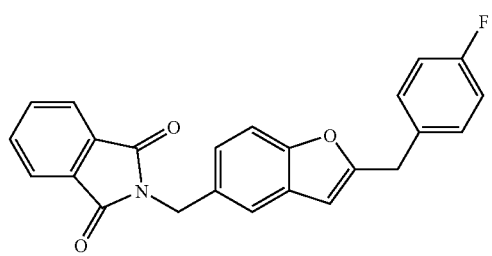
Production Example 76-1-3

TABLE 12-continued

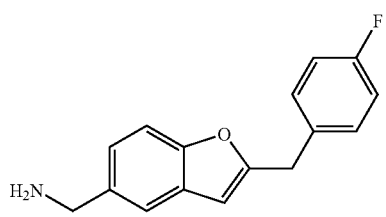

Production Example 76-1-4

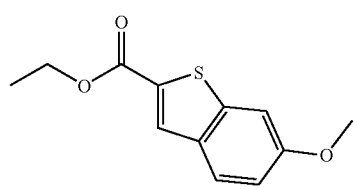

Production Example 77-1-1

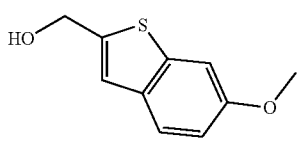

Production Example 77-1-2

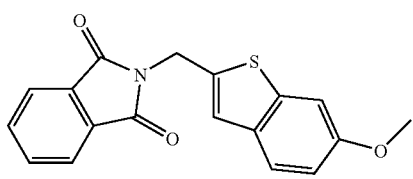

Production Example 77-1-3

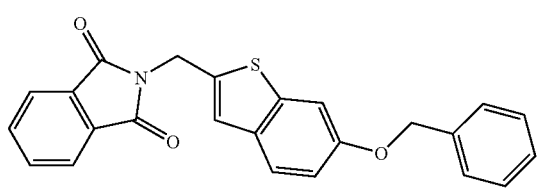

Production Example 77-1-4

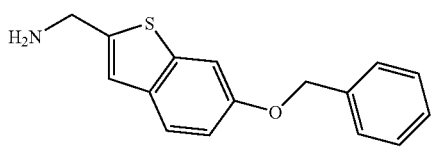

Production Example 77-1-5

Pyridine derivatives (I) or salts, or hydrates thereof according to the present invention demonstrate superior inhibitory activity on the GPI-anchored protein transport process, anti-Candida activity and anti-Aspergillus activity, and are also superior in terms of physical properties, safety and metabolic stability, making then extremely useful as a preventive or therapeutic agents for fungal infections.

Pharmacological Test Example

The antifungal activity of compound (1) of the present invention was assessed by measuring: 1) anti-*Candida* activity and anti-*Aspergillus* activity, and 2) activity in the experimental systemic candidal infection model in mice, in order to demonstrate the usefulness of compounds (1) according to the present invention.

1. Anti-*Candida* Activity and Anti-*Aspergillus* Activity (1) Preparation of Fungal Suspensions For the *C. albicans* E81022 strain, a fungal suspension from a standing culture 48 hours at 30° C. in a Sabouraud dextrose liquid culture medium (SDB) was diluted 10000-fold with 1.3-times concentrated RPMI1640 medium to prepare a fungal suspension containing 1 to $2 \times 10^4$ cells/ml. For the *A. fumigatus* Tsukuba strain, −80° C. stored strain was diluted 1000-fold with 1.3-times concentrated RPMI1640 medium to prepare a fungal suspension containing 2 to $3 \times 10^3$ cells/ml.

(2) Preparation of Drug Dilution Plates

Using a U-shaped bottomed 96-well plates, 8 samples/plate (A to H) of sample dilution solutions were prepared. On the first row was dispensed 240 µl of sterile distilled water, and on the $2^{nd}$ to $12^{th}$ row were dispersed 125 µL of 4% dimethylsulfoxide solution. Weighed sample was dissolved in dimethylsulfoxide to prepare a 5 mg/ml solution followed by adding 10 µL of the solutions to the first row of the prepared plates and preparing 12-step serial 2-fold dilutions (125 µL of solution+125 µL of 4% dimethylsulfoxide solution) on the plates. This sample dilution solution was dispensed in the amount of 25 µL to a flat-bottom 96-well plates for MIC measurement MIC to prepare a sample dilution plate.

(3) Inoculation of Fungal Suspension and Culture

The fungal suspension prepared in (1) was used in the amount of 75 µL/well to inoculate the flat-bottomed 96-well plates containing 25 µL/well of the test compound prepared in (2), and a standing culture was carried out aerobically for 48 hours at 35° C.

(4) MIC Measurement

The minimum concentration that clearly inhibited fungal growth as compared with the control by visual inspection was defined as the minimum growth inhibitory concentration (MIC).

The following representative compounds prepared in the examples were measured for the anti-Candida activity and anti-Aspergillus activity by the measurement method described in 1. As a result, as shown in Tables 13 and 14, it was found that the compounds according to the present invention clearly had anti-Candida activity and anti-Aspergillus activity.

TABLE 13

| Example No. | Anti-*Candida* activity (µg/ml) |
|---|---|
| 1 | 0.39 |
| 2 | 1.56 |
| 3 | 1.56 |
| 4 | 0.78 |
| 5 | 0.78 |
| 6 | 0.78 |
| 7 | 0.39 |

TABLE 13-continued

| Example No. | Anti-*Candida* activity (μg/ml) |
|---|---|
| 8 | 1.56 |
| 12 | 0.78 |
| 13 | 0.39 |
| 14 | 1.56 |
| 16 | 3.13 |
| 17 | 0.78 |
| 22 | 0.39 |
| 23 | 1.56 |
| 24 | 6.25 |
| 25 | 0.78 |
| 29 | 1.56 |
| 33 | 12.5 |
| 37 | 0.2 |
| 38 | 0.39 |
| 39 | 1.56 |
| 40 | 3.13 |
| 41 | 3.13 |
| 42 | 1.56 |
| 43 | 0.78 |
| 44 | 0.78 |
| 45 | 12.5 |
| 46 | 0.39 |
| 47 | 0.78 |
| 49 | 0.39 |
| 51 | 0.2 |
| 52 | 1.56 |
| 53 | 6.25 |
| 54 | 1.56 |
| 57 | 6.25 |
| 58 | 0.1 |
| 59 | 0.78 |
| 65 | 1.56 |
| 69 | 0.39 |
| 70 | 0.78 |
| 72 | 0.78 |
| 77 | 0.39 |
| 78 | 0.39 |
| 80 | 3.13 |

TABLE 14

| Example No. | Anti-*Aspergillus* activity (μg/ml) |
|---|---|
| 1 | 1.56 |
| 2 | 3.13 |
| 3 | 0.78 |
| 4 | 3.13 |
| 5 | 0.78 |
| 6 | 1.56 |
| 7 | 1.56 |
| 12 | 1.56 |
| 13 | 1.56 |
| 16 | 6.25 |
| 22 | 1.56 |
| 24 | 3.13 |
| 29 | 6.25 |
| 38 | 0.78 |
| 39 | 1.56 |
| 40 | 3.13 |
| 42 | 3.13 |
| 43 | 6.25 |
| 44 | 6.25 |
| 45 | 12.5 |
| 47 | 1.56 |
| 49 | 6.25 |
| 51 | 0.78 |
| 52 | 0.78 |
| 53 | 6.25 |
| 54 | 0.39 |
| 57 | 1.56 |
| 58 | 1.56 |
| 59 | 3.13 |
| 65 | 3.13 |
| 69 | 0.39 |

TABLE 14-continued

| Example No. | Anti-*Aspergillus* activity (μg/ml) |
|---|---|
| 70 | 1.56 |
| 72 | 1.56 |
| 73 | 25 |
| 77 | 3.13 |
| 78 | 1.56 |
| 79 | 12.5 |
| 81 | 6.25 |

2. Experimental Systemic *Candida* Infection Model in Mice (1) Preparation of Fungal Inoculant A standing culture of *C. albicans* E81022 strain was static cultured for 48 hours at 30° C. in Sabouraud's dextrose agar (SDA), and the recovered fungal cells were suspended in sterilized physiological saline. By counting the fungal number on cytometry plate, the suspension was diluted to $2 \times 10^7$ cells/mL with sterilized saline to serve fungal inoculant.

(2) Infection

The fungal inoculum was used in the amounts of 0.2 mL to inoculate 4.5 to 5.5 week-old femal ICR mice in the tail vein ($4 \times 10^6$ cells/mouse).

(3) Treatment

From 0.5 to 1 hour after fungal inoculation, 0.2 mL of agent solution (dissolved or suspended in sterilized saline containing 6.5% dimethylsulfoxide and 3.5% Tween 80) was administered into the stomach using a peroral probe, three times every 4 hours. The agent concentration was set at 10 mg/kg and the number of animals in one group was 5 animals.

(4) Determination of Results

The protective effect was determined by observing life/death until 14 days after infection and calculating the mean survival days.

As a result, as shown in Table 15, mice administered with the compound according to the present invention survived for a long time as compared to the non-administered group, clearly demonstrating that the compounds according to the present invention demonstrate anti-Candida activity in vivo as well.

TABLE 15

| Example Nos | Mean Survival Days |
|---|---|
| 1 | 9.6 |
| 2 | 8.6 |
| 3 | 8.6 |
| 4 | 10.2 |
| 5 | 12.8 |
| 6 | 11.4 |
| 7 | 8.8 |
| 9 | 9.6 |
| Non-administered group | 2.4 to 4.0 |

INDUSTRIAL APPLICABILITY

According to the present invention, pyridine derivatives (I), or salts or hydrates thereof according to the present invention, 1) inhibit expression of cell wall surface layer protein, inhibit cell wall assembly and inhibit the adherence of fungi to cells to prevent pathogens from demonstrating pathogenicity, thereby demonstrating effects against the onset, progression and prolongation of infections; and 2) are superior in terms of physical properties, safety and metabolic stability, and are extremely useful as preventives or therapeutics for fungal infections.

We claim:
1. A compound represented by the following formula (I), or a salt thereof:

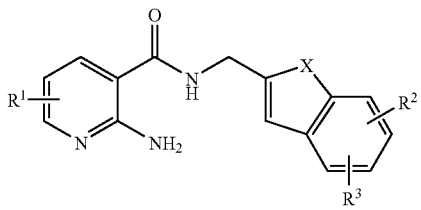

wherein X represents an oxygen atom,
$R^1$ represents a hydrogen atom, a halogen atom, a cyano group, an amino group or a group selected from substituent group a; and
$R^2$ and $R^3$ independently represent a hydrogen atom, a halogen atom, a hydroxyl group or a group selected from substituent group c, except for a case in which $R^2$ and $R^3$ are both hydrogen atoms:

substituent group a:

a $C_{1-6}$ alkyl group, a $C_{2-6}$ alkenyl group, a $C_{2-6}$ alkynyl group, a $C_{3-8}$ cycloalkyl group, a $C_{3-8}$ cycloalkyl $C_{1-6}$ alkyl group, a $C_{1-6}$ alkoxy group, a $C_{2-6}$ alkenyloxy group, a $C_{2-6}$ alkynyloxy group, a $C_{3-8}$ cycloalkoxy group, a $C_{3-8}$ cycloalkyl $C_{1-6}$ alkoxy group, a $C_{1-6}$ alkylthio group, a $C_{3-8}$ cycloalkyl $C_{1-6}$ alkylthio group, a mono-$C_{1-6}$ alkylamino group, a mono-$C_{2-6}$ alkenylamino group, a mono-$C_{2-6}$ alkynylamino group, a mono-$C_{3-8}$ cycloalkylamino group, a mono-$C_{3-8}$ cycloalkyl $C_{1-6}$ alkylamino group, a di-$C_{1-6}$ alkylamino group, a $C_{1-6}$ alkylcarbonyl group and a $C_{1-6}$ alkoxy $C_{1-6}$ alkyl group, and each group described in substituent group a may have 1 to 3 groups selected from the following substituent group b:

substituent group b:

a halogen atom, a hydroxyl group, a mercapto group, a cyano group, a $C_{1-6}$ alkyl group, a $C_{6-10}$ aryl group, a $C_{1-6}$ alkoxy group and an aminosulfonyl group, substituent group c:

a $C_{1-6}$ alkyl group, a $C_{2-6}$ alkenyl group, a $C_{2-6}$ alkynyl group, a $C_{3-8}$ cycloalkyl $C_{1-6}$ alkyl group, a $C_{6-10}$ aryl $C_{1-6}$ alkyl group, a $C_{1-6}$ alkoxy group, a $C_{2-6}$ alkenyloxy group, a $C_{2-6}$ alkynyloxy group, a $C_{5-10}$ aryloxy group, a $C_{3-8}$ cycloalkyl $C_{1-6}$ alkoxy group, a $C_{6-10}$ aryl $C_{1-6}$ alkoxy group, a $C_{6-10}$ aryloxy $C_{1-6}$ alkoxy group, a $C_{1-6}$ alkoxy $C_{1-6}$ alkoxy group, a mono-$C_{6-10}$ arylamino group, a mono-$C_{6-10}$ aryl $C_{1-6}$ alkylamino group, a $C_{6-10}$ aryloxy $C_{1-6}$ alkyl group, and a $C_{1-6}$ alkoxy $C_{1-6}$ alkyl group, and each group described in substituent group c may have 1 to 3 groups selected from the group consisting of a halogen atom, a $C_{1-6}$ alkyl group and a $C_{1-6}$ alkoxy group.

2. The compound, or the salt thereof according to claim 1, wherein $R^1$ represents a hydrogen atom, an amino group or a $C_{1-6}$ alkoxy $C_{1-6}$ alkyl group.

3. The compound, or the salt thereof according to claim 1, wherein $R^1$ represents a hydrogen atom, an amino group or a methoxymethyl group.

4. The compound, or the salt thereof according to claim 1, wherein $R^2$ and $R^3$ independently represents a hydrogen atom, a halogen atom or a group selected from substituent group c-1:

substituent group c-1:

a $C_{1-6}$ alkyl group, a $C_{6-10}$ aryl $C_{1-6}$ alkyl group, a $C_{1-6}$ alkoxy group, a $C_{2-6}$ alkenyloxy group, a $C_{2-6}$ alkynyloxy group, a $C_{6-10}$ aryloxy group, a $C_{3-8}$ cycloalkyl $C_{1-6}$ alkoxy group, a $C_{6-10}$ aryl $C_{1-6}$ alkoxy group, a $C_{6-10}$ aryloxy $C_{1-6}$ alkoxy group, a $C_{1-6}$ alkoxy $C_{1-6}$ alkoxy group and a $C_{1-6}$ alkoxy $C_{1-6}$ alkyl group, and each group described in substituent group c-1 may have 1 to 3 groups selected from the group consisting of a halogen atom, a $C_{1-6}$ alkyl group and a $C_{1-6}$ alkoxy group.

5. The compound, or the salt thereof according to claim 1, wherein $R^2$ and $R^3$ independently represents a hydrogen atom, a halogen atom or a group selected from substituent group c-2:

substituent group c-2:

a butyl group, a benzyl group, a methoxy group, an ethoxy group, a propoxy group, a butoxy group, a pentyloxy group, an isobutoxy group, a 4-methylbutoxy group, a 2-methylbutoxy group, a 2,2-dimethylpropoxy group, an allyloxy group, a 3-methyl-but-2-enyloxy group, a but-2-enyloxy group, a prop-2-ynyloxy group, a but-2-ynyloxy group, a phenoxy group, a cyclopropylmethoxy group, a phenoxyethoxy group, a benzyloxy group, a 2-fluoro-benzyloxy group, a 3-fluoro-benzyloxy group, a 4-fluoro-benzyloxy group, a 2-chloro-benzyloxy group, a methoxyethoxy group, an ethoxyethoxy group, a methoxymethyl group and an ethoxymethyl group.

6. The compound, or the salt thereof according to claim 4, wherein only one of $R^2$ and $R^3$ is a hydrogen atom.

7. The compound, or the salt thereof according to claim 1, wherein a bonding position of $R^1$ is a position represented by the partial structure of the following formula (II):

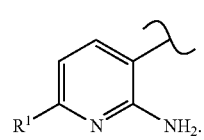

8. The compound, or the salt thereof according to claim 1, wherein bonding positions of $R^2$ and $R^3$ are the positions represented by the partial structure of the following formula (III):

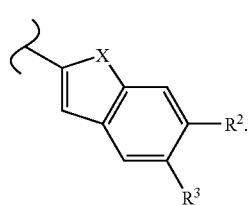

9. A compound selected from the group consisting of the following compounds, or a salt thereof:

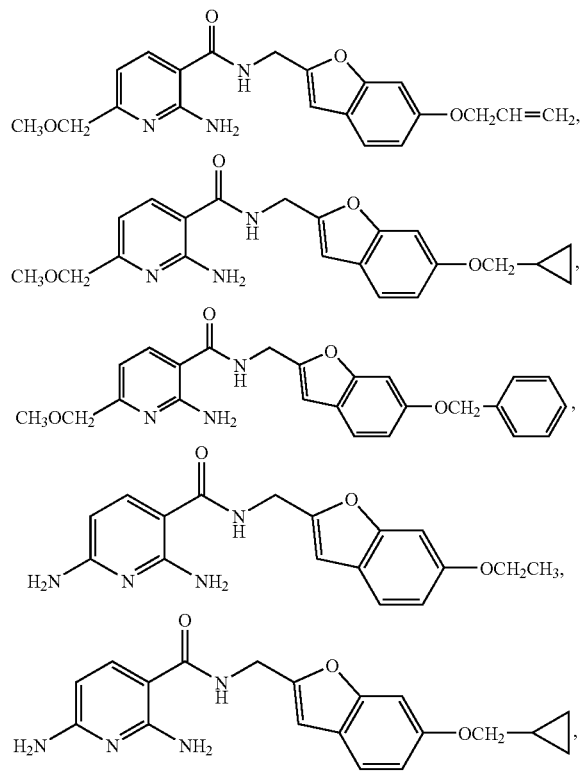
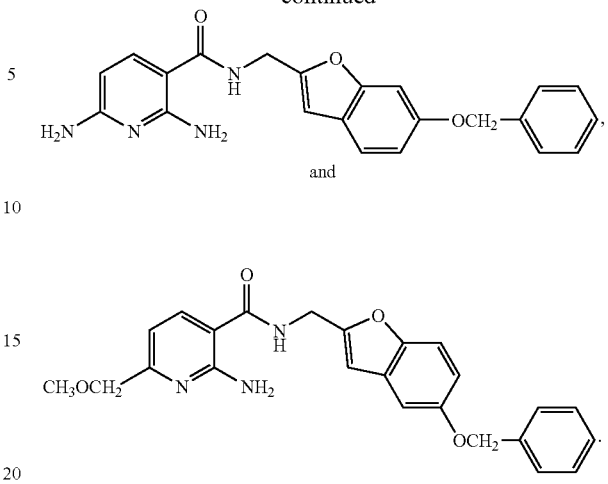
10. A pharmaceutical composition comprising the compound, or the salt thereof according to claim 1; and a pharmaceutically acceptable carrier.
11. A method for treating a fungal infection by administering a pharmacologically effective amount of the compound, or the salt thereof according to claim 1.
* * * * *